US009096587B2

(12) United States Patent
Holsworth et al.

(10) Patent No.: US 9,096,587 B2
(45) Date of Patent: Aug. 4, 2015

(54) TRIAZOLE DERIVATIVES AS WNT SIGNALING PATHWAY INHIBITORS

(75) Inventors: Daniel Holsworth, San Diego, CA (US); Jo Waaler, Oslo (NO); Ondrej Machon, Prague (CZ); Stefan Krauss, Eidsvoll verk (NO); Andrey Edward Voronkov, Oslo (NO)

(73) Assignee: OSLO UNIVERSITY HOSPITAL HF (NO)

( * ) Notice: Subject to any disclaimer, the term of this patent is extended or adjusted under 35 U.S.C. 154(b) by 0 days.

(21) Appl. No.: 13/992,879

(22) PCT Filed: Dec. 8, 2011

(86) PCT No.: PCT/GB2011/052441
§ 371 (c)(1),
(2), (4) Date: Oct. 21, 2013

(87) PCT Pub. No.: WO2012/076898
PCT Pub. Date: Jun. 14, 2012

(65) Prior Publication Data
US 2014/0031374 A1    Jan. 30, 2014

Related U.S. Application Data

(60) Provisional application No. 61/420,942, filed on Dec. 8, 2010.

(51) Int. Cl.
*C07D 401/12* (2006.01)
*C07D 413/14* (2006.01)
*A61K 31/5377* (2006.01)

(52) U.S. Cl.
CPC ............ *C07D 413/14* (2013.01); *C07D 401/12* (2013.01)

(58) Field of Classification Search
CPC . C07D 401/12; C07D 413/14; A61K 31/5377
USPC ............... 514/256, 340, 333; 546/256, 272.4, 546/269.4; 544/333; 435/377
See application file for complete search history.

(56) References Cited

U.S. PATENT DOCUMENTS

| 6,080,772 | A | 6/2000 | Tang et al. |
| 2005/0272779 | A1 | 12/2005 | Edwards et al. |
| 2007/0203194 | A1* | 8/2007 | Zelle et al. ............ 514/338 |
| 2008/0287452 | A1 | 11/2008 | Bursavich et al. |
| 2008/0287482 | A1 | 11/2008 | Gregory et al. |
| 2009/0131336 | A1 | 5/2009 | Cho et al. |
| 2012/0208828 | A1 | 8/2012 | Holsworth |

FOREIGN PATENT DOCUMENTS

| JP | 09316440 | * 12/1997 |
| WO | 2004014881 A2 | 2/2004 |
| WO | 2005004818 A2 | 1/2005 |
| WO | 2005080356 A1 | 9/2005 |
| WO | 2006014185 A1 | 2/2006 |
| WO | 2007040982 A1 | 4/2007 |
| WO | 2007139967 A2 | 12/2007 |
| WO | 2008011557 A2 | 1/2008 |
| WO | 2009005269 A2 | 1/2009 |
| WO | 2009030996 A1 | 3/2009 |
| WO | 2009051556 A1 | 4/2009 |
| WO | 2009054785 A1 | 4/2009 |
| WO | 2009054794 A1 | 4/2009 |
| WO | 2010139966 A1 | 12/2010 |

OTHER PUBLICATIONS

Wolff, Manfred E. "Burger's Medicinal Chemistry, 5ed, Part I", John Wiley & Sons, 1995, pp. 975-977.*
Banker, G.S., "Modern Pharmaceutics, 3ed.", Marcel Dekker, New York, 1996, pp. 451 and 596.*
Dorwald; "Side Reactions in Organic Synthesis: A Guide to Successful Synthesis Design" 2005 Wiley-VCH Verlag GmbH & Co. KGaA, Wienheim, Chapter 1.*
Chemical Abstracts STN record for registry No. 355810-06-9; Sep. 11, 2001.*
Chemical Abstracts STN record for registry No. 1022878-85-8; May 27, 2008.*
Matiichuk; Russian Journal of Organic Chemistry, 2010, vol. 46, No. 10, pp. 1550-1557.*
Hirayama, et al.; "Identification of Novel Chemical Inhibitors for Ubiquitin C-Terminal Hydrolase-L3 by Virtual Screening"; Bioorganic & Medicinal Chemistry; 15; pp. 6810-6818; (2007).
Horig et al.; "From Bench to Clinic and Back: Perspective on the 1st IQPC Translational Research Conference"; Journal of Translational Medicine; 2(44); pp. 1-8; (2004).
International Search Report; Interntional Application No. PCT/GB2010/001118; International Filing Date Jun. 7, 2010; Date of Mailing Jul. 30, 2010; 5 pages.
International Search Report and Written Opinion; International Application No. PCT/GB2011/052441; International Filing Date Dec. 8, 2011; Date of Mailing Mar. 5, 2012.
Schafer et al.; "Failure is an Option: Learning From Unsuccessful Proof-of-Concept Trials"; Drug Discovery Today; 13(21/22); pp. 913-916; (2008).
U.S. Appl. No. 13/376,202, filed Apr. 4, 2012; NonFinal Office Action; Mailed May 29, 2013; 30 pages.
U.S. Appl. No. 13/376,202, filed Apr. 4, 2012; Final Office Action; Mailed Jan. 13, 2014; 10 pages.
International Preliminary Report on Patentability; International Application No. PCT/GB2011/052441; International Filing Date Dec. 8, 2011; Date of Mailing Jun. 20, 2013; 8 pages.

* cited by examiner

*Primary Examiner* — John Mabry
*Assistant Examiner* — Daniel Carcanague
(74) *Attorney, Agent, or Firm* — Cantor Colburn LLP

(57) ABSTRACT

The present invention relates to compounds of formula (I), to processes for their preparation, to pharmaceutical formulations containing such compounds and to their use in therapy: Such compounds find particular use in the treatment and/or prevention of conditions or diseases which are affected by over-activation of signaling in the Wnt pathway and increased presence of nuclear β-catenin. For example, these may be used in preventing and/or retarding proliferation of tumor cells and metastasis, for example carcinomas such as colon carcinomas.

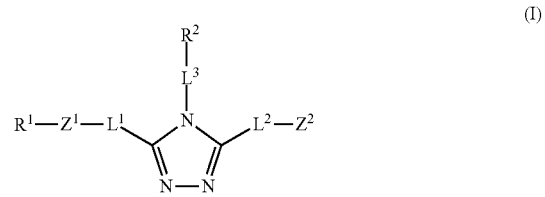

(I)

11 Claims, 7 Drawing Sheets

A

B

A

B

A

B

TRIAZOLE DERIVATIVES AS WNT SIGNALING PATHWAY INHIBITORS

CROSS-REFERENCE TO RELATED APPLICATIONS

This application is a 371 of PCT/GB2011/052441 filed Dec. 8, 2011, which claims the benefit of priority to U.S. provisional application No. 61/420,942, filed on, Dec. 8, 2010 under the provisions of 35 U.S.C. 119 and the International Convention for the protection of Industrial Property, which are incorporated herein by reference.

The present invention relates to compounds, to pharmaceutical formulations containing such compounds and to their use in therapy, in particular as Wnt signaling pathway inhibitors for reducing the proliferation of tumor cells and metastasis. The invention further relates to processes for the preparation of such compounds and to intermediates formed during these processes.

The Wnt family of glycoproteins control a variety of developmental processes including cell fate specification, proliferation, polarity and migration. Consequently, the Wnt pathway is instrumental in ensuring proper tissue development in embryos and tissue maintenance in adults. There are at least three signaling pathways involved in the Wnt signal transduction process. The canonical (or β-catenin dependent) Wnt pathway was discovered first and has been studied most. In the absence of a Wnt signal, the transcriptional activator β-catenin is a phosphorylated intracellular multi-protein complex which is subsequently degraded. Within this complex the AXIN and adenomatous polyposis coli (APC) proteins form a scaffold that facilitates β-catenin phosphorylation by casein-kinase1α (CK1α) and glycogen synthase kinase 3β (GSK-3β). Phosphorylated β-catenin is subsequently ubiquitinylated, resulting in its degradation in the proteasome. When Wnt signaling is inactive and therefore levels of free β-catenin are low, DNA-binding T-cell factor/lymphoid enhancer factor (TCF/LEF) proteins interact with transcriptional repressors to block Wnt target gene expression in the nucleus. Binding of Wnt molecules to FZD-LRP receptor complexes at the membrane leads to a cascade of events that lead to the inactivation of the β-catenin destruction complex. This allows β-catenin to accumulate and enter the nucleus where it interacts with members of the Tcf/Lef family and converts the Tcf proteins into potent transcriptional activators by recruiting co-activator proteins ensuring efficient activation of Wnt target genes.

Canonical Wnt signaling is over-activated in a variety of tumors where it plays a central role in cell growth and tumor progression (Barker et al., Nat. Rev. Drug. Discov. 5: 997-1014, 2006; Grigoryan et al., Genes Dev. 22: 2308-2341, 2008; and Shitashige et al., Cancer Sci. 99: 631-637, 2008). About 90% of sporadic colon cancers show aberrant Wnt signaling (Liu et al., Nat. Genet. 26: 146-147, 2000; and Morin et al., Science 275: 1787-1790, 1997), while all pancreatic adenocarcinomas exhibit alterations in Wnt/Notch signaling (Jones et al., Science 321: 1801-1806, 2008).

Wnt activating mutations are present in a variety of cancers including gastric cancer, hepatocellular carcinoma, Wilms tumor of the kidney, medulloblastoma, melanoma, non-small cell lung cancer, ovarian endometriod cancer, anaplastic thyroid cancer, pancreas adenocarcinoma, and prostate cancer (Barker et al. supra). Mutations in the adenomatous polyposis coli gene (APC), β-catenin, or Axin genes lead to accumulation of nuclear β-catenin and such mutations are frequently associated with colon cancer (Morin et al. supra). Furthermore, alterations in extracellular proteins which silence Wnt signaling including secreted frizzled related proteins (SFRPs) (Suzuki et al., Nat. Genet 36: 417-422, 2004), Dickkopf (Dkk) (Aguilera et al., Oncogene 25: 4116-4121, 2006) and members of the Wnt inhibitor factor (WIF) family (Mazieres et al., Cancer Res. 64: 4717-4720, 2004) can also lead to abnormal pathway activity (Polakis, Curr. Opin. Genet. Dev. 17: 45-51, 2007).

Blocking canonical Wnt activity in colorectal and other Wnt deregulated cancers has been shown to cause cell cycle arrest in G1 and this is a crucial step in inhibiting tumor cell growth (van de Wetering et al., Cell 111: 241-250, 2002; and Sukhdeo et al., Proc. Natl. Acad. Sci. USA 104: 7516-7521, 2007). In recent years, several classes of small-molecules have been shown to act as Wnt inhibitors. These drugs exert their inhibitory effects at various levels of the Wnt signaling pathway. Small molecules, interfering with nuclear TCF/β-catenin binding and with the cyclic AMP response element-binding protein (CBP), have been identified and described (Emami et al., Proc. Natl. Acad. Sci. USA 101: 12682-12687, 2004; and Lepourcelet M et al., Cancer Cell 5: 91-102, 2004). Topo IIα and PARP-1 (Shitashige et al., Cancer Sci. 99: 631-637, 2008) or TBP, BRG1, BCL9, pygopus and Hyrax (Barker et al. supra) have been proposed to be potential targets for inhibiting canonical Wnt signaling. Recently, two groups of chemical substances (IWR-1 and XAV939) have been identified which stabilize the destruction complex (Chen et al., Nat. Chem. Biol. 5: 100-107, 2009; and Huang et al., Nature: 461: 614-620, 2009). By blocking the PARP domain of Tankyrase, XAV939 and IWR-1 are thought to alter the PARsylation and ubiquitination of AXIN2 that results in its increased stability and in inhibition of canonical Wnt signaling. Since elevated levels of β-catenin in the nucleus are a common feature of abnormal canonical Wnt signaling, down-regulation of canonical Wnt activity by reducing the presence of β-catenin represents a potential therapeutic strategy.

We have now found a selected class of compounds which exhibit an activity in blocking canonical Wnt signaling, and in particular which are capable of reducing levels of activated nuclear β-catenin. To the extent that these are able to affect the stability of activated β-catenin downstream of APC and GSK-3β, these are considered to offer broader potential than other compounds known to act further upstream in the canonical Wnt signaling pathway. Such compounds are suitable for inhibiting the proliferation of tumor cells in general and, in particular, those associated with colorectal cancers, breast cancer, non-small cell lung cancer, prostate cancer and pancreatic adenocarcinoma.

The invention provides compounds of general formula I:

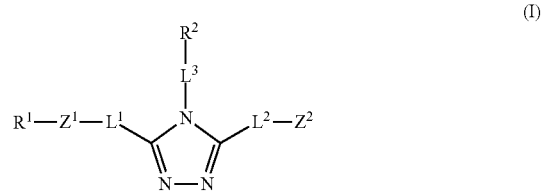

(wherein $Z^1$ represents an unsaturated, 5- to 7-membered heterocyclic ring, or a group of the formula —$(CH_2)_x$—CO—NH—NH—CO—$(CH_2)_y$— wherein x and y independently denote an integer from 0 to 2;

$Z^2$ represents an aryl or heteroaryl group optionally substituted by one or more (e.g. 1, 2, 3 or 4) groups $R_a$;

where each $R_a$ may be identical or different and may be selected from halogen (i.e. F, Cl, Br, I), $C_{1-6}$ alkyl (preferably $C_{1-3}$ alkyl), $C_{2-4}$ alkenyl, $C_{2-4}$ alkynyl, $C_{1-4}$ haloalkyl (e.g. $CF_3$), —CN, —$NO_2$, —OR, —SR, —C(O)R, —C(O)OR, —OC(O)R, —OC(O)$NR_2$, —C(O)$NR_2$, —$NR_2$, —NR—C(O)R, —NR—C(O)OR, —S(O)R, —S(O)$_2$R, —S(O)OR or —S(O)$_2NR_2$ group (where each R is independently H, $C_{1-6}$ alkyl, $C_{1-6}$ haloalkyl, $C_{2-6}$ alkenyl or $C_{2-6}$ alkynyl);

$R^1$ represents an aryl or heteroaryl group optionally substituted by one or more (e.g. 1, 2, 3 or 4) groups $R_b$;

where each $R_b$ may be identical or different and may be selected from halogen (i.e. F, Cl, Br, I), $C_{1-6}$ alkyl (preferably $C_{1-3}$ alkyl) optionally interrupted by one or more —O—, —S— or —NR— groups (preferably by one or two —O— atoms), $C_{2-4}$ alkenyl, $C_{2-4}$ alkynyl, $C_{1-4}$ haloalkyl (e.g. $CF_3$), —CN, —$NO_2$, —OR, —SR, —C(O)R, —C(O)OR, —OC(O)R, —OC(O)$NR_2$, —C(O)$NR_2$, —$NR_2$, —NR—C(O)R, —NR—C(O)OR, —S(O)R, —S(O)$_2$R, —S(O)OR or —S(O)$_2NR_2$ group (where each R is independently H, $C_{1-6}$ alkyl, $C_{1-6}$ haloalkyl, $C_{2-6}$ alkenyl or $C_{2-6}$ alkynyl);

$R^2$ represents an aryl or heteroaryl group optionally substituted by one or more (e.g. 1, 2, 3 or 4) groups $R_c$;

where each $R_c$ may be identical or different and may be selected from halogen (i.e. F, Cl, Br, I), $C_{1-6}$ alkyl (preferably $C_{1-3}$ alkyl), $C_{2-4}$ alkenyl, $C_{2-4}$ alkynyl, $C_{1-4}$ haloalkyl (e.g. $CF_3$), —CN, —$NO_2$, —OR, —SR, —C(O)R, —C(O)OR, —OC(O)R, —OC(O)$NR_2$, —$NR_2$, —NR—C(O)R, —NR—C(O)OR, —S(O)R, —S(O)$_2$R, —S(O)OR or —S(O)$_2NR_2$ group (where each R is independently H, $C_{1-6}$ alkyl, $C_{1-6}$ haloalkyl, $C_{2-6}$ alkenyl or $C_{2-6}$ alkynyl);

$L^1$ represents a $C_{1-4}$ alkylene group optionally substituted by one or more (e.g. 1 or 2) groups $R_d$, wherein one or more (preferably one or two) methylene groups are each replaced by a group selected from —$CR_e$=$CR_f$—, —C≡C— and —C=C=C—; and wherein one or more (preferably one to three) methylene groups may each additionally be replaced by a group $Y^1$; where each $Y^1$ is independently selected from —O—, —S—, —NH—, —NR'''—, —NR'''—C(O)—, —C(O)—NR'''—, —C(O)—, —S(O$_2$)—, —S(O)— and —CR'''=N— (where each R''' is independently hydrogen or $C_{1-6}$ alkyl);

where each $R_d$ may be identical or different and may be selected from $C_{1-6}$ alkyl (preferably $C_{1-3}$ alkyl), hydroxy, $C_{1-6}$ alkoxy (e.g. $C_{1-3}$ alkoxy) and halogen (i.e. F, Cl, Br and I, preferably F); and where $R_e$ and $R_f$ are independently selected from H, $C_{1-3}$ alkyl, halogen (e.g. F or Cl), $C_{1-3}$ haloalkyl (e.g. —$CF_3$), —CN, —$NO_2$, —OR, —SR, —C(O)R, —C(O)OR, —OC(O)R, —$OPO_3R$, —$OSO_2R$ and —$OSiR_4$ (where each R is independently H, $C_{1-6}$ alkyl or $C_{1-6}$ haloalkyl);

$L^2$ represents a bond or an optionally substituted $C_{1-6}$ alkylene group; and $L^3$ represents a bond or an optionally substituted $C_{1-6}$ alkylene group)

the isomers (e.g. stereoisomers), pharmaceutically acceptable salts, and prodrugs thereof.

In any of the embodiments of the invention herein described, it is envisaged that in the definition of the linker $L^1$ all methylene groups may be replaced by a group —$CR_e$=$CR_f$—, —C≡C— or —C=C=C—). Suitable linkers, $L^1$, therefore include groups which contain no methylene moiety (i.e. where all such groups have been replaced by a group —$CR_e$=$CR_f$—, —C≡C— or —C=C=C—).

In formula I, $L^3$ is preferably a direct bond or a —$CH_2$— group.

Preferred compounds in accordance with the invention are those of general formula II:
(wherein

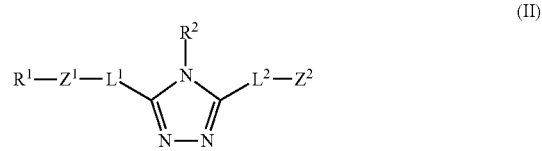

(II)

$Z^1$ represents an unsaturated, 5- to 7-membered heterocyclic ring, or a group of the formula —$(CH_2)_x$—CO—NH—NH—CO—$(CH_2)_y$— wherein x and y independently denote an integer from 0 to 2;

$Z^2$ represents an aryl or heteroaryl group optionally substituted by one or more (e.g. 1, 2, 3 or 4) groups $R_a$;

where each $R_a$ may be identical or different and may be selected from halogen (i.e. F, Cl, Br, I), $C_{1-6}$ alkyl (preferably $C_{1-3}$ alkyl), $C_{2-4}$ alkenyl, $C_{2-4}$ alkynyl, $C_{1-4}$ haloalkyl (e.g. $CF_3$), —CN, —$NO_2$, —OR, —SR, —C(O)R, —C(O)OR, —OC(O)R, —OC(O)$NR_2$, —$NR_2$, —NR—C(O)R, —NR—C(O)OR, —S(O)R, —S(O)$_2$R, —S(O)OR or —S(O)$_2NR_2$ group (where each R is independently H, $C_{1-6}$ alkyl, $C_{1-6}$ haloalkyl, $C_{2-6}$ alkenyl or $C_{2-6}$ alkynyl);

$R^1$ represents an aryl or heteroaryl group optionally substituted by one or more (e.g. 1, 2, 3 or 4) groups $R_b$;

where each $R_b$ may be identical or different and may be selected from halogen (i.e. F, Cl, Br, I), $C_{1-6}$ alkyl (preferably $C_{1-3}$ alkyl), $C_{2-4}$ alkenyl, $C_{2-4}$ alkynyl, $C_{1-4}$ haloalkyl (e.g. $CF_3$), —CN, —$NO_2$, —OR, —SR, —C(O)R, —C(O)OR, —OC(O)R, —OC(O)$NR_2$, —$NR_2$, —NR—C(O)R, —NR—C(O)OR, —S(O)R, —S(O)$_2$R or —S(O)OR group (where each R is independently H, $C_{1-6}$ alkyl, $C_{1-6}$ haloalkyl, $C_{2-6}$ alkenyl or $C_{2-6}$ alkynyl);

$R^2$ represents an aryl or heteroaryl group (preferably an aryl group) optionally substituted by one or more (e.g. 1, 2, 3 or 4) groups $R_c$;

where each $R_c$ may be identical or different and may be selected from halogen (i.e. F, Cl, Br, I), $C_{1-6}$ alkyl (preferably $C_{1-3}$ alkyl), $C_{2-4}$ alkenyl, $C_{2-4}$ alkynyl, $C_{1-4}$ haloalkyl (e.g. $CF_3$), —CN, —$NO_2$, —OR, —SR, —C(O)R, —C(O)OR, —OC(O)R, —OC(O)$NR_2$, —$NR_2$, —NR—C(O)R, —NR—C(O)OR, —S(O)R, —S(O)$_2$R, —S(O)OR or —S(O)$_2NR_2$ group (where each R is independently H, $C_{1-6}$ alkyl, $C_{1-6}$ haloalkyl, $C_{2-6}$ alkenyl or $C_{2-6}$ alkynyl);

$L^1$ represents a $C_{1-4}$ alkylene group optionally substituted by one or more (e.g. 1 or 2) groups $R_d$, wherein one or more (preferably one or two) methylene groups are each replaced by a group selected from —$CR_e$=$CR_f$—, —C≡C— and —C=C=C—; and wherein one or more (preferably one to three) methylene groups may each additionally be replaced by a group $Y^1$; where each $Y^1$ is independently selected from —O—, —S—, —NH—, —NR'''—, —NR'''—C(O)—, —C(O)—NR'''—, —C(O)—, —S(O$_2$)—, —S(O)— and —CR'''=N— (where each R''' is independently hydrogen or $C_{1-6}$ alkyl);

where each $R_d$ may be identical or different and may be selected from $C_{1-6}$ alkyl (preferably $C_{1-3}$ alkyl), hydroxy, $C_{1-6}$ alkoxy (e.g. $C_{1-3}$ alkoxy) and halogen (i.e. F, Cl, Br and I, preferably F); and where $R_e$ and $R_f$ are independently selected from H, $C_{1-3}$ alkyl, halogen (e.g. F or Cl), $C_{1-3}$ haloalkyl (e.g. —CF$_3$), —CN, —NO$_2$, —OR, —SR, —C(O)R, —C(O)OR, —OC(O)R, —OPO$_3$R, —OSO$_2$R and —OSiR$_4$ (where each R is independently H, $C_{1-6}$ alkyl or $C_{1-6}$ haloalkyl);

$L^2$ represents a bond or an optionally substituted $C_{1-6}$ alkylene group, preferably a bond)

the isomers (e.g. stereoisomers), pharmaceutically acceptable salts, and prodrugs thereof.

In the compounds herein described, preferred linkers $L^1$ comprise a $C_{1-4}$ alkylene group (preferably a $C_{1-2}$ alkylene) optionally substituted by one or more (e.g. 1 or 2) groups $R_d$, wherein one or more (preferably one or two) methylene groups are each replaced by a group —CR$_e$=CR$_f$— or by a group —C≡C—;

where each $R_d$ may be identical or different and may be selected from $C_{1-6}$ alkyl (preferably $C_{1-3}$ alkyl), hydroxy, $C_{1-6}$ alkoxy (e.g. $C_{1-3}$ alkoxy) and halogen (i.e. F, Cl, Br and I, preferably F); and where $R_e$ and $R_f$ are independently selected from H, $C_{1-3}$ alkyl, halogen (e.g. F or Cl) and —CN.

In the compounds of formula I and II, where $Z^1$ is a group of the formula —(CH$_2$)$_x$—CO—NH—NH—CO—(CH$_2$)$_y$—, it is preferred that x and y are both zero.

Particularly preferred compounds in accordance with the invention are those of formula I or II wherein:

$Z^1$ represents a 5-membered heterocyclic ring containing two or three heteroatoms selected from N, O and S;

$Z^2$ represents phenyl, pyridyl, pyrimidinyl or oxadiazolyl optionally substituted by one or more (e.g. 1, 2, 3 or 4) groups $R_a$;

where each $R_a$ may be identical or different and may be selected from halogen (i.e. F, Cl, Br, I), $C_{1-6}$ alkyl (preferably $C_{1-3}$ alkyl), $C_{2-4}$ alkenyl, $C_{2-4}$ alkynyl, $C_{1-4}$ haloalkyl (e.g. CF$_3$), —CN, —NO$_2$, —OR, —SR, —C(O)R, —C(O)OR, —OC(O)R, —OC(O)NR$_2$, —NR$_2$, —NR—C(O)R, —NR—C(O)OR, —S(O)R, —S(O)$_2$R, —S(O)OR or —S(O)$_2$NR$_2$ group (where each R is independently H, $C_{1-6}$ alkyl, $C_{1-6}$ haloalkyl, $C_{2-6}$ alkenyl or $C_{2-6}$ alkynyl);

$R^1$ represents an aryl or heteroaryl group optionally substituted by one or more (e.g. 1, 2, 3 or 4) groups $R_b$;

where each $R_b$ may be identical or different and may be selected from halogen (i.e. F, Cl, Br, I), $C_{1-6}$ alkyl (preferably $C_{1-3}$ alkyl), $C_{2-4}$ alkenyl, $C_{2-4}$ alkynyl, $C_{1-4}$ haloalkyl (e.g. CF$_3$), —CN, —NO$_2$, —OR, —SR, —C(O)R, —C(O)OR, —OC(O)R, —OC(O)NR$_2$, —NR$_2$, —NR—C(O)R, —NR—C(O)OR, —S(O)R, —S(O)$_2$R or —S(O)OR group (where each R is independently H, $C_{1-6}$ alkyl, $C_{1-6}$ haloalkyl, $C_{2-6}$ alkenyl or $C_{2-6}$ alkynyl);

$R^2$ represents an aryl group optionally substituted by one or more (e.g. 1, 2, 3 or 4) groups $R_c$;

where each $R_c$ may be identical or different and may be selected from halogen (i.e. F, Cl, Br, I), $C_{1-6}$ alkyl (preferably $C_{1-3}$ alkyl), $C_{2-4}$ alkenyl, $C_{2-4}$ alkynyl, $C_{1-4}$ haloalkyl (e.g. CF$_3$), —CN, —NO$_2$, —OR, —SR, —C(O)R, —C(O)OR, —OC(O)R, —OC(O)NR$_2$, —NR$_2$, —NR—C(O)R, —NR—C(O)OR, —S(O)R, —S(O)$_2$R, —S(O)OR or —S(O)$_2$NR$_2$ group (where each R is independently H, $C_{1-6}$ alkyl, $C_{1-6}$ haloalkyl, $C_{2-6}$ alkenyl or $C_{2-6}$ alkynyl);

$L^1$ represents a $C_{1-4}$ alkylene group (preferably a $C_{1-2}$ alkylene) optionally substituted by one or more (e.g. 1 or 2) groups $R_d$, wherein one or two methylene groups (e.g. one methylene group) are each replaced by a group —CR$_e$=CR$_f$— or by a group —C≡C—;

where each $R_d$ may be identical or different and may be selected from $C_{1-6}$ alkyl (preferably $C_{1-3}$ alkyl), hydroxy and $C_{1-6}$ alkoxy (e.g. $C_{1-3}$ alkoxy);

where $R_e$ and $R_f$ are independently selected from H, $C_{1-3}$ alkyl (e.g. methyl), halogen (e.g. F or Cl) and —CN; and $L^2$ represents a bond or an optionally substituted $C_{1-4}$ alkylene group, preferably a bond) the isomers (e.g. stereoisomers), pharmaceutically acceptable salts and prodrugs thereof.

More particularly preferred compounds according to the invention are those of formula I or II wherein:

$Z^1$ represents a 5-membered heterocyclic ring containing two nitrogen atoms and one oxygen atom;

$Z^2$ represents phenyl, pyridyl or pyrimidinyl optionally mono- or di-substituted by a group $R_a$;

where $R_a$ may be selected from halogen (i.e. F, Cl, Br, I), hydroxy, $C_{1-6}$ alkoxy (e.g. $C_{1-3}$ alkoxy) and —S(O)$_2$R (where R is H or $C_{1-3}$ alkyl);

$R^1$ represents an aryl or heteroaryl group optionally monosubstituted by group $R_b$;

where $R_b$ is selected from halogen (i.e. F, Cl, Br, I), $C_{1-6}$ alkyl (preferably $C_{1-3}$ alkyl), $C_{1-6}$ alkoxy (e.g. $C_{1-3}$ alkoxy), hydroxy and —CN;

$R^2$ represents an aryl group optionally mono- or di-substituted by a group $R_c$;

where each $R_c$ may be identical or different and may be selected from halogen (i.e. F, Cl, Br, I), $C_{1-6}$ alkyl (preferably $C_{1-3}$ alkyl) and $C_{1-6}$ alkoxy (e.g. $C_{1-3}$ alkoxy);

$L^1$ represents a $C_{1-4}$ alkylene group (preferably a $C_{1-2}$ alkylene) optionally substituted by one or more (e.g. 1 or 2) groups $R_d$, wherein one or two methylene groups (e.g. one methylene group) are each replaced by a group —CR$_e$=CR$_f$— or by a group —C≡C—;

where each $R_d$ may be identical or different and may be selected from $C_{1-6}$ alkyl (preferably $C_{1-3}$ alkyl), hydroxy and $C_{1-6}$ alkoxy (e.g. $C_{1-3}$ alkoxy);

where $R_e$ and $R_f$ are independently selected from H, $C_{1-3}$ alkyl and halogen (e.g. F or Cl); and $L^2$ represents a bond, or a $C_{1-2}$ alkylene group)

the isomers (e.g. stereoisomers), pharmaceutically acceptable salts and prodrugs thereof.

Examples of group $Z^1$ in formula I and II include the following:

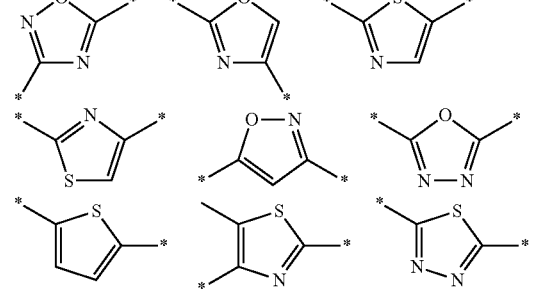

-continued

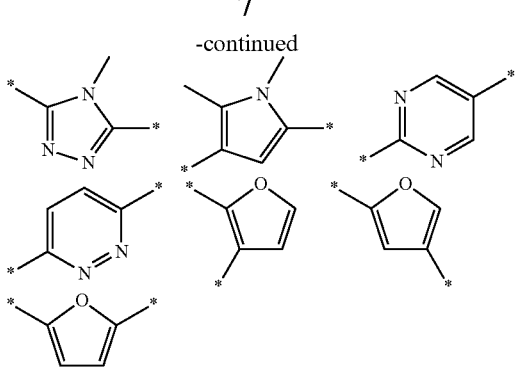

Of these structures, the following are particularly preferred for $Z^1$:

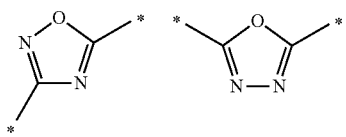

In a yet further preferred aspect the invention thus provides the following compounds of formulae Ia, IIa, Ib and IIb:

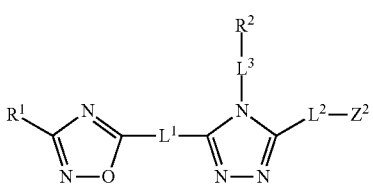
(Ia)

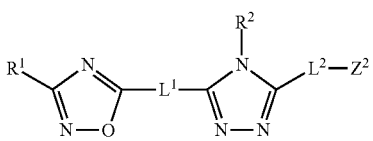
(IIa)

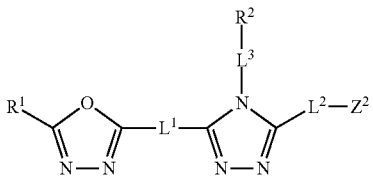
(Ib)

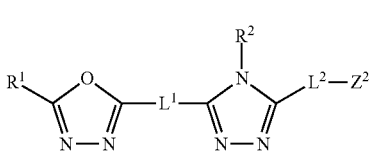
(IIb)

(wherein $Z^2$, $R^1$, $R^2$, $L^1$, $L^2$ and $L^3$ are as hereinbefore defined); the isomers (e.g. stereoisomers), pharmaceutically acceptable salts and prodrugs thereof.

In preferred embodiments, $Z^2$ represents an optionally substituted aryl or heteroaryl group, preferably a phenyl, pyridyl or pyrimidinyl group optionally substituted by one or two (preferably one) groups $R_a$ in which each $R_a$ is independently halogen (preferably Cl or F), hydroxy, $C_{1-6}$ alkoxy (preferably $C_{1-3}$ alkoxy, e.g. methoxy) or —S(O)$_2$R (where R is H or $C_{1-3}$ alkyl). Particularly preferably, $Z^2$ represents an option- ally substituted phenyl or pyridyl group, e.g. optionally substituted pyridyl. When substituted, the substituents on the ring may independently be selected from the group consisting of hydroxy, methoxy, ethoxy, chloro, fluoro and methylsulphonyl. Preferred substituents are ethoxy, chloro, fluoro and methylsulphonyl. One or more of such groups may be present on the ring and in any ring position. However, it is preferred that one or two such groups will be present. Where two substituents are present these will generally be identical.

Examples of group $Z^2$ include the following:

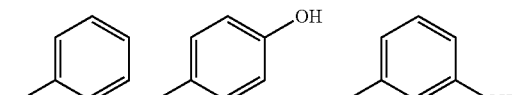

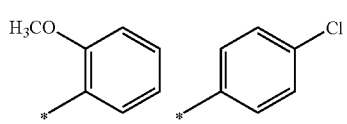

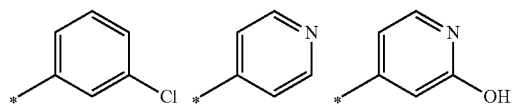

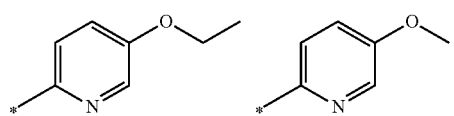

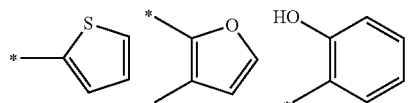

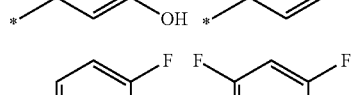

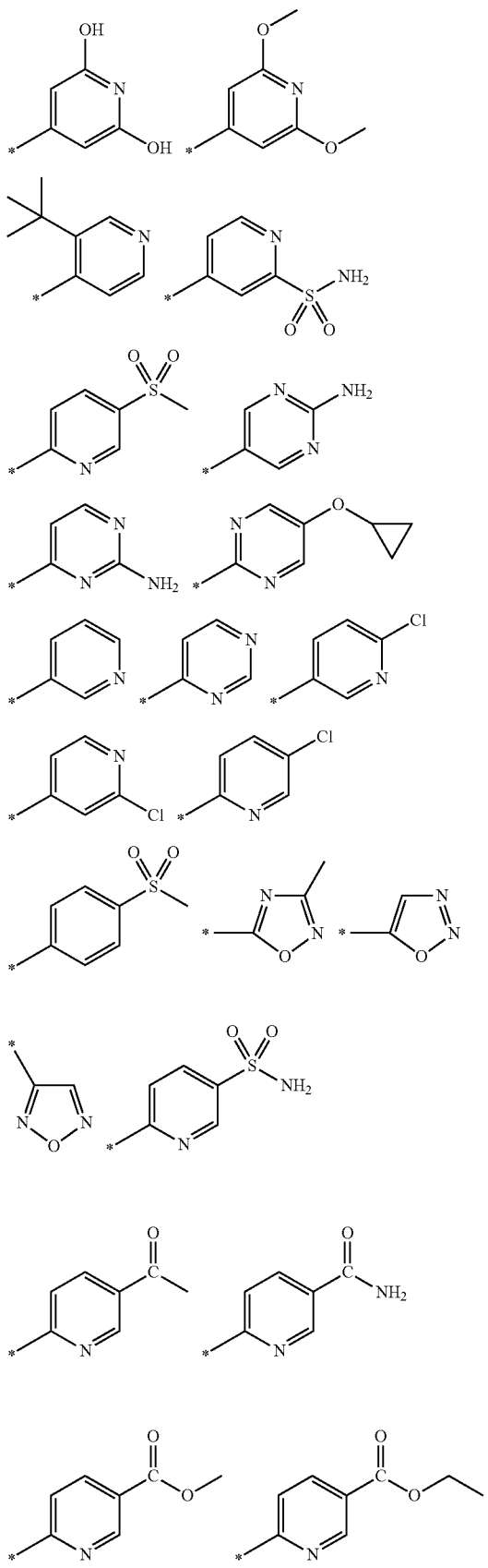

Particularly preferred groups $Z^2$ include the following:

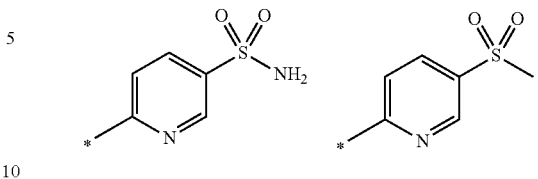

In preferred embodiments, $R^1$ represents phenyl or pyridyl optionally substituted by one or two (preferably one) groups $R_b$ in which each $R_b$ is independently halogen (e.g. F, Cl or Br), hydroxy, $C_{1-6}$ alkyl (preferably $C_{1-3}$ alkyl, e.g. methyl), $C_{1-6}$ alkoxy (preferably $C_{1-3}$ alkoxy, e.g. methoxy) or cyano. Particularly preferably, $R^1$ represents a substituted (e.g. mono-substituted) pyridyl ring. Preferred substituents include hydroxy, methoxy and cyano groups, especially methoxy.

Examples of group $R^1$ include the following:

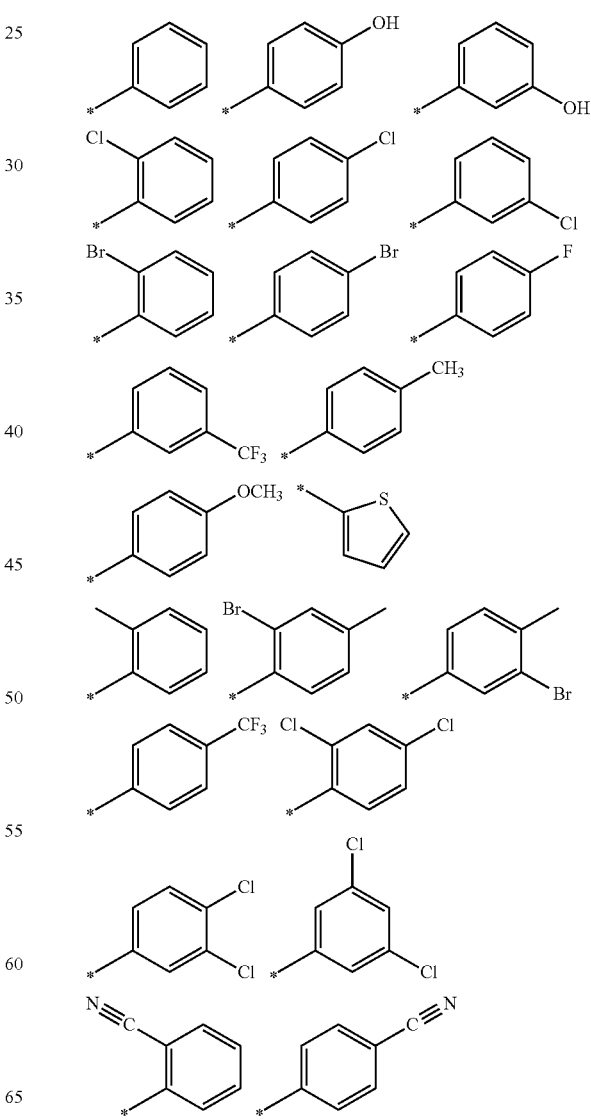

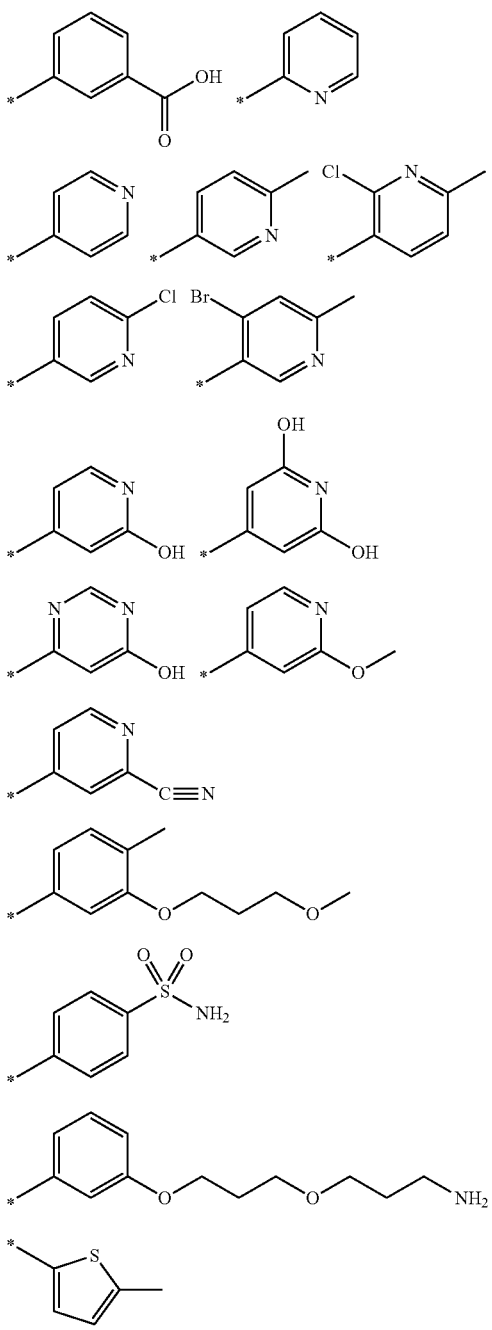

Particularly preferred groups R¹ include the following:

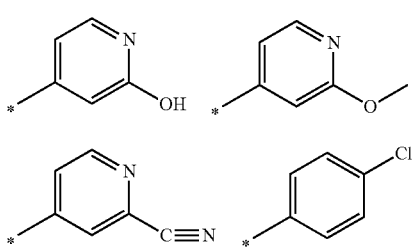

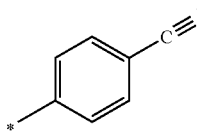

In preferred embodiments, R² represents phenyl or pyridyl optionally substituted by one or two groups R, in which each $R_c$ is independently halogen (e.g. F or Cl) or $C_{1-6}$ alkoxy (preferably $C_{1-3}$ alkoxy, e.g. methoxy or ethoxy).

Particularly preferably, R² is optionally substituted phenyl. When substituted, the ring substituents on the phenyl group may independently be selected from the group consisting of $C_{1-3}$ alkyl (e.g. methyl or ethyl), methoxy, ethoxy, chloro and fluoro. One or more of such groups may be present on the ring and in any ring position. However, it is preferred that one or two such groups will be present. Particularly preferably, the phenyl ring will be substituted by a single chloro group either in the ortho or para-position, e.g. in the ortho-position.

Examples of group R² include the following:

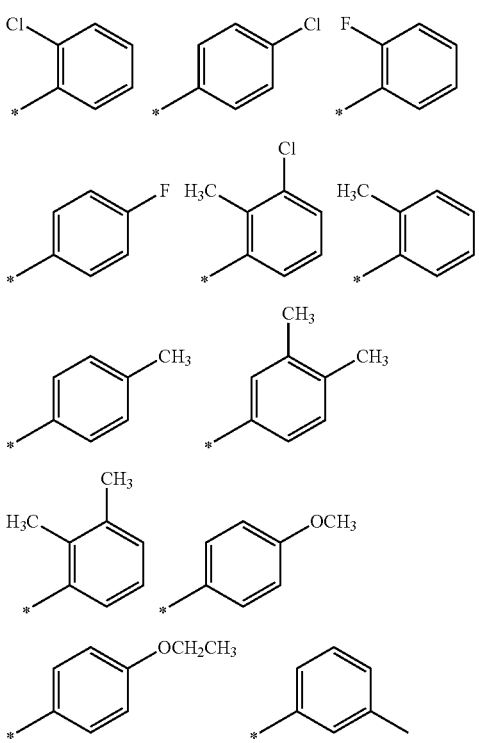

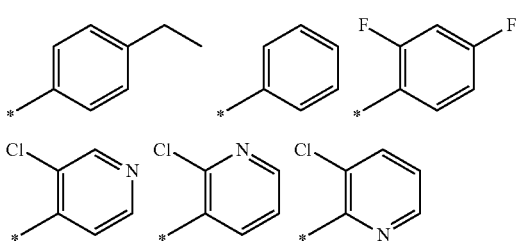

Particularly preferably, $R^2$ is a group:

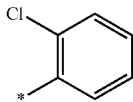 [SMILES: *c1ccccc1Cl]

In preferred embodiments, $L^1$ is a $C_1$ alkylene linker in which the single methylene group is either replaced by a group —$CR_e$=$CR_f$— (where $R_e$ and $R_f$ are as hereinbefore defined), by a group —C≡C— or by a group —C=C=C—.

Particularly preferred as linker groups $L^1$ are groups of the formula —$CR_e$=$CR_f$— in which $R_e$ and $R_f$ are independently selected from H and $C_{1-3}$ alkyl. Such groups may be either cis or trans, although preferably they will be in the trans configuration.

Particularly preferably, $R_e$ and $R_f$ in the linker group $L^1$ are identical and are either both H or both methyl. A preferred linker group $L^1$ is —CH=CH—.

Examples of $L^1$ include the following:

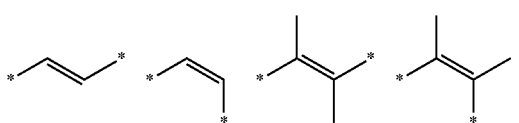

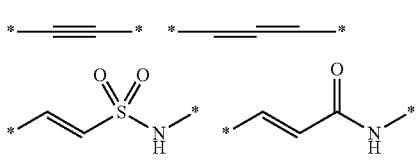

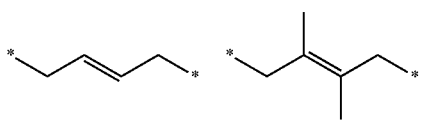

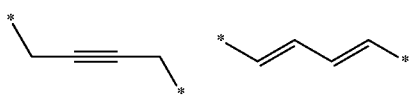

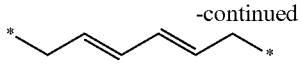

In preferred embodiments $L^2$ is a bond or a $C_{1-2}$ alkylene group (e.g. methylene). Preferably $L^2$ is a bond.

In preferred embodiments, $L^3$ is a bond.

Particularly preferred compounds according to the invention are the following compounds of formulae IIc and IId:

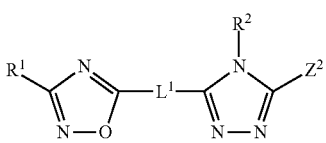
(IIc)

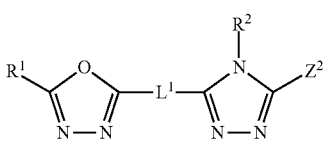
(IId)

(wherein $Z^2$ is an optionally substituted pyridyl, phenyl or pyrimidinyl ring, preferably a phenyl ring substituted by one or two (preferably by one) halo atoms (e.g. Cl or F) or by one methylsulphonyl group, or a pyridyl ring optionally substituted by a halo atom (e.g. Cl), by an alkoxy group (e.g. ethoxy) or by a methylsulphonyl group;

$R^1$ is a substituted phenyl or pyridyl ring, preferably a phenyl or pyridyl ring substituted by a halo atom (e.g. Cl), a $C_{1-6}$ alkoxy (e.g. methoxy) group, a hydroxy or cyano group;

$R^2$ is an optionally substituted phenyl ring, preferably a phenyl ring substituted by one halo atom (e.g. Cl);

$L^1$ is cis or trans —CH=CH—, preferably trans —CH=CH—)

the isomers (e.g. stereoisomers), pharmaceutically acceptable salts and prodrugs thereof.

The following are examples of particularly preferred compounds in accordance with the invention:

| Compound No. | Structre |
| --- | --- |
| (1) | |

-continued

| Compound No. | Structre |
| --- | --- |
| (2) | |
| (3) | |
| (4) | |
| (5) | |
| (6) | |

-continued
| Compound No. | Structre |
|---|---|
| (7) | 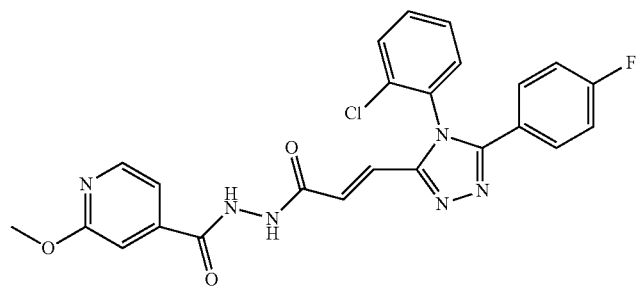 [SMILES: COc1cc(C(=O)NNC(=O)/C=C/c2nnc(-c3ccc(F)cc3)n2-c2ccccc2Cl)ccn1] |
| (8) | 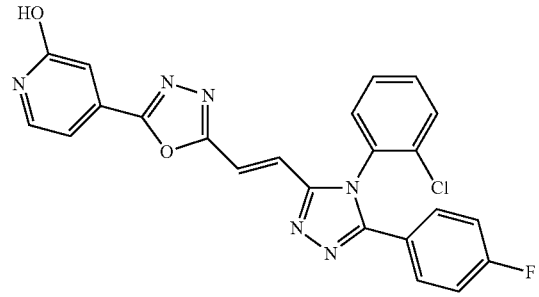 [SMILES: Oc1cc(-c2nnc(/C=C/c3nnc(-c4ccc(F)cc4)n3-c3ccccc3Cl)o2)ccn1] |
| (9) | 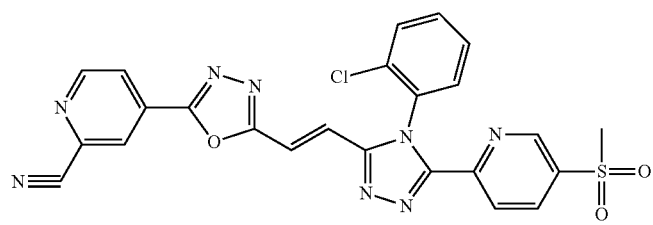 [SMILES: CS(=O)(=O)c1ccc(-c2nnc(/C=C/c3nnc(-c4ccnc(C#N)c4)o3)n2-c2ccccc2Cl)nc1] |
| (10) | 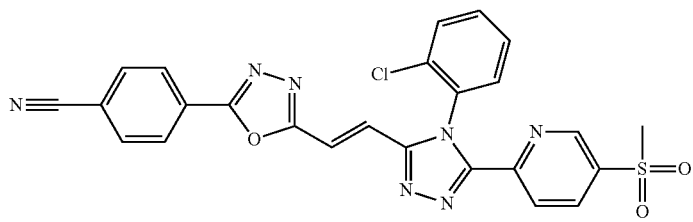 [SMILES: CS(=O)(=O)c1ccc(-c2nnc(/C=C/c3nnc(-c4ccc(C#N)cc4)o3)n2-c2ccccc2Cl)nc1] |
| (11) | 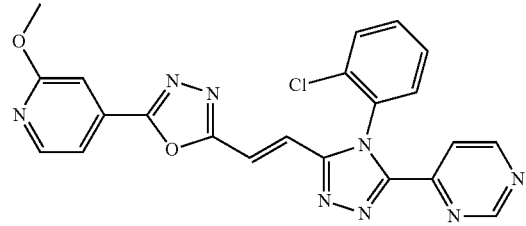 [SMILES: COc1cc(-c2nnc(/C=C/c3nnc(-c4ccncn4)n3-c3ccccc3Cl)o2)ccn1] |
| (12) | 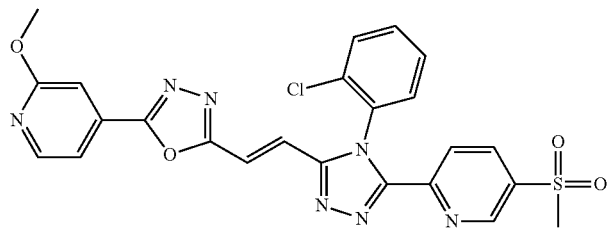 [SMILES: COc1cc(-c2nnc(/C=C/c3nnc(-c4ccc(S(C)(=O)=O)cn4)n3-c3ccccc3Cl)o2)ccn1] |

| Compound No. | Structre |
|---|---|
| (13) | 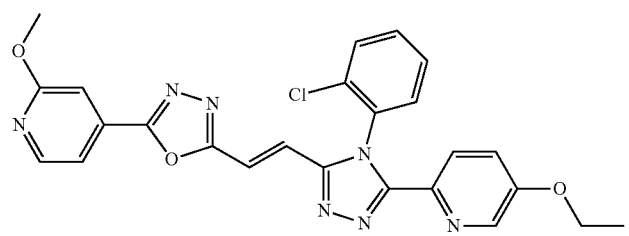 [SMILES: CCOc1ccc(-c2nnc(/C=C/c3nnc(-c4ccnc(OC)c4)o3)n2-c2ccccc2Cl)nc1] |
| (14) | 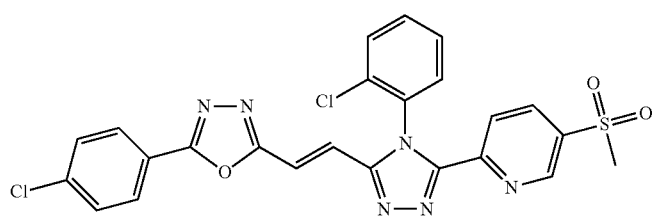 [SMILES: CS(=O)(=O)c1ccc(-c2nnc(/C=C/c3nnc(-c4ccc(Cl)cc4)o3)n2-c2ccccc2Cl)nc1] |
| (15) | 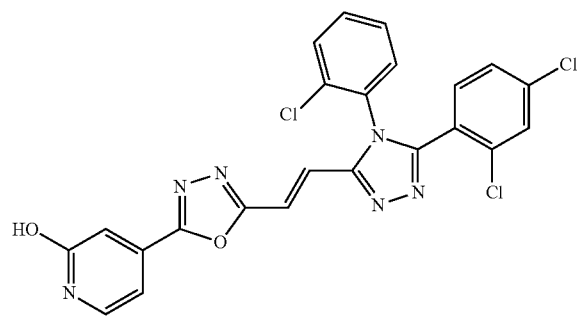 [SMILES: Oc1cc(-c2nnc(/C=C/c3nnc(-c4ccc(Cl)cc4Cl)n3-c3ccccc3Cl)o2)ccn1] |
| (16) | 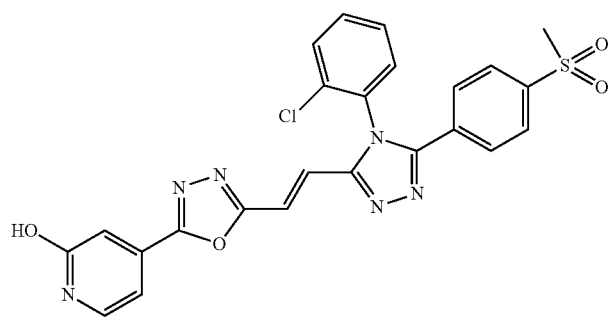 [SMILES: CS(=O)(=O)c1ccc(-c2nnc(/C=C/c3nnc(-c4ccnc(O)c4)o3)n2-c2ccccc2Cl)cc1] |
| (17) | 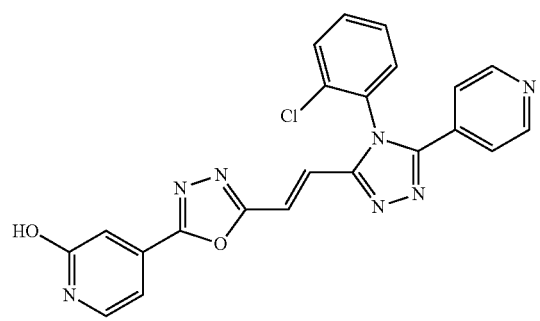 [SMILES: Oc1cc(-c2nnc(/C=C/c3nnc(-c4ccncc4)n3-c3ccccc3Cl)o2)ccn1] |

| Compound No. | Structre |
|---|---|
| (18) | 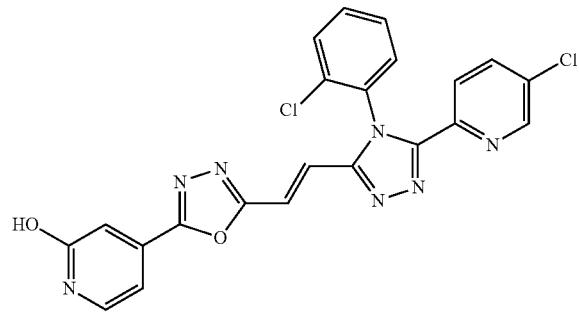 [SMILES: Oc1cc(-c2nnc(/C=C/c3nnc(-c4ccc(Cl)cn4)n3-c3ccccc3Cl)o2)ccn1] |
| (19) | 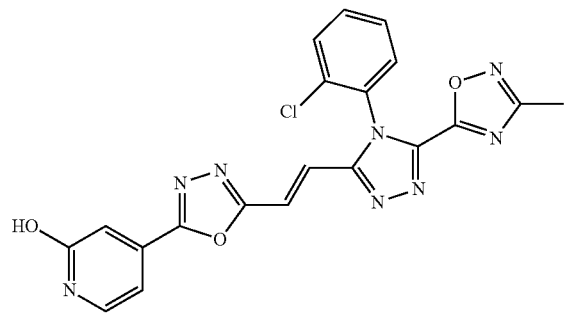 [SMILES: Cc1noc(-c2nnc(/C=C/c3nnc(-c4ccnc(O)c4)o3)n2-c2ccccc2Cl)n1] |
| (20) | 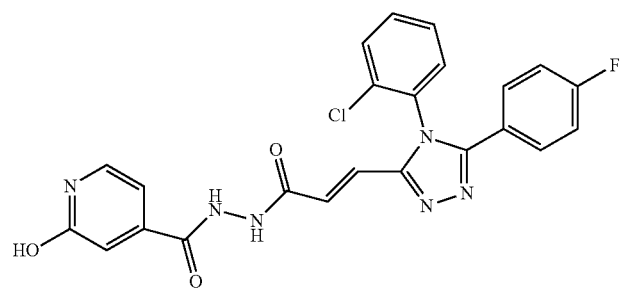 [SMILES: O=C(/C=C/c1nnc(-c2ccc(F)cc2)n1-c1ccccc1Cl)NNC(=O)c1ccnc(O)c1] |
| (21) | 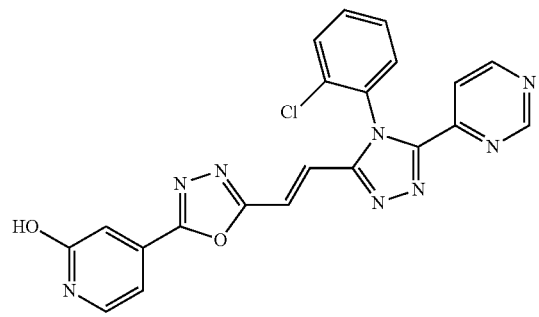 [SMILES: Oc1cc(-c2nnc(/C=C/c3nnc(-c4ccncn4)n3-c3ccccc3Cl)o2)ccn1] |

| Compound No. | Structre |
|---|---|
| (22) | 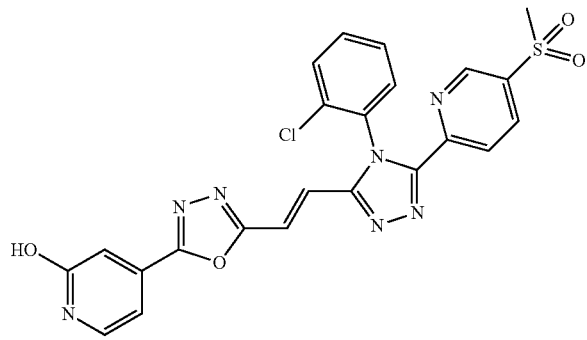 [SMILES: CS(=O)(=O)c1ccc(-c2nnc(/C=C/c3nnc(-c4ccnc(O)c4)o3)n2-c2ccccc2Cl)nc1] |
| (23) | 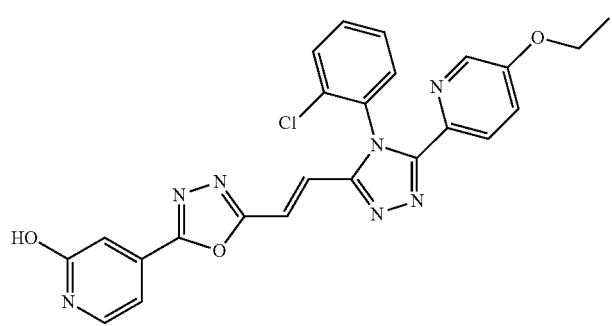 [SMILES: CCOc1ccc(-c2nnc(/C=C/c3nnc(-c4ccnc(O)c4)o3)n2-c2ccccc2Cl)nc1] |
| (24) | 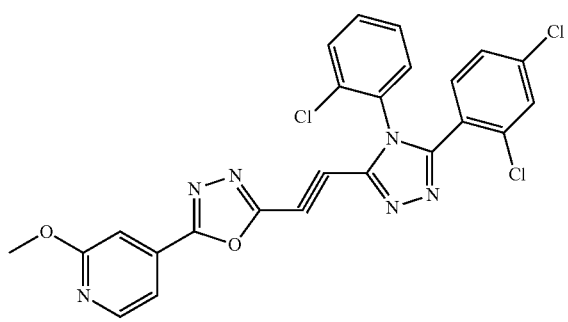 [SMILES: COc1cc(-c2nnc(C#Cc3nnc(-c4ccc(Cl)cc4Cl)n3-c3ccccc3Cl)o2)ccn1] |
| (25) | 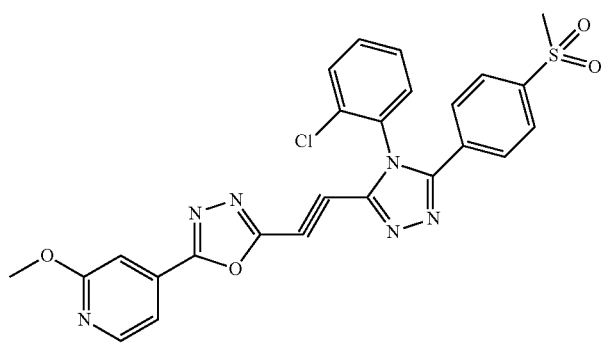 [SMILES: COc1cc(-c2nnc(C#Cc3nnc(-c4ccc(S(C)(=O)=O)cc4)n3-c3ccccc3Cl)o2)ccn1] |

| Compound No. | Structre |
|---|---|
| (26) | 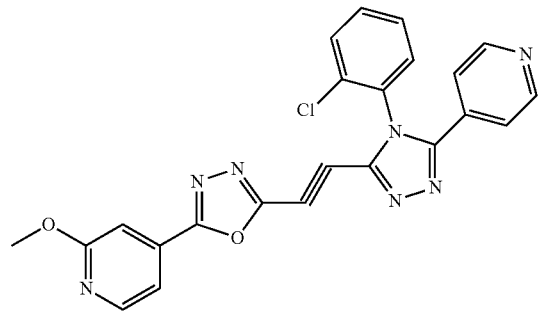 [SMILES: COc1cc(-c2nnc(C#Cc3nnc(-c4ccncc4)n3-c3ccccc3Cl)o2)ccn1] |
| (27) | 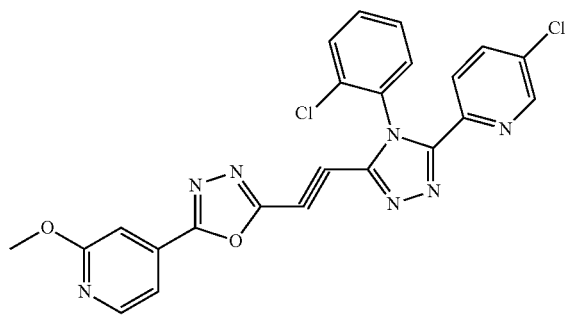 [SMILES: COc1cc(-c2nnc(C#Cc3nnc(-c4ccc(Cl)cn4)n3-c3ccccc3Cl)o2)ccn1] |
| (28) | 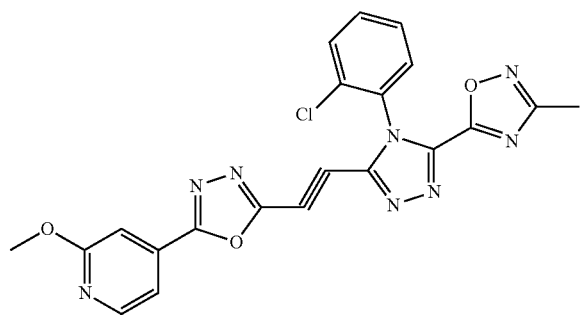 |
| (29) | 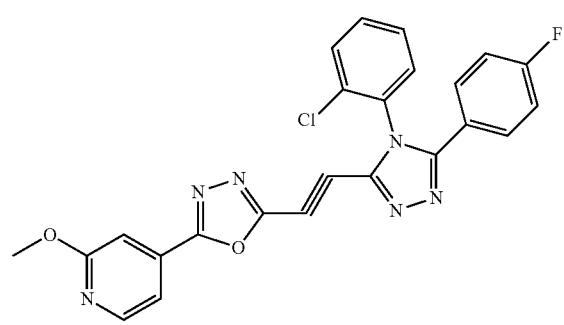 [SMILES: COc1cc(-c2nnc(C#Cc3nnc(-c4ccc(F)cc4)n3-c3ccccc3Cl)o2)ccn1] |

| Compound No. | Structre |
|---|---|
| (30) | 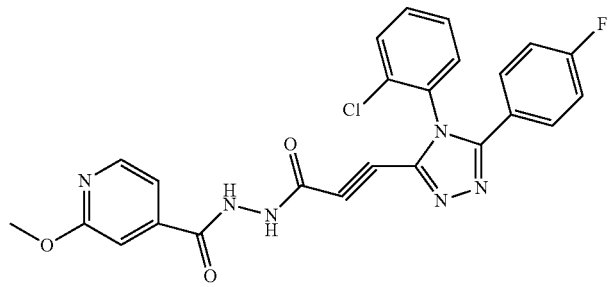 [SMILES: COc1cc(C(=O)NNC(=O)C#Cc2nnc(-c3ccc(F)cc3)n2-c2ccccc2Cl)ccn1] |
| (31) | 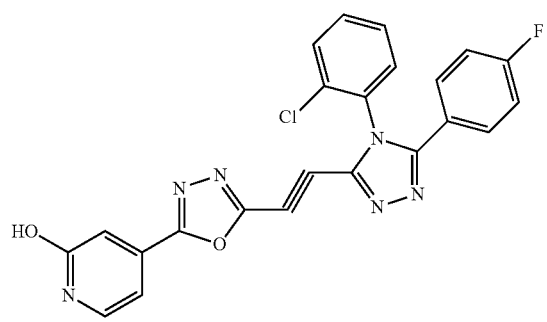 [SMILES: Oc1cc(-c2nnc(C#Cc3nnc(-c4ccc(F)cc4)n3-c3ccccc3Cl)o2)ccn1] |
| (32) | 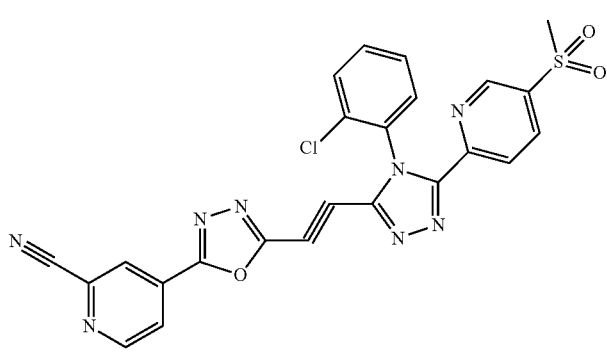 [SMILES: CS(=O)(=O)c1ccc(-c2nnc(C#Cc3nnc(-c4ccnc(C#N)c4)o3)n2-c2ccccc2Cl)nc1] |
| (33) | 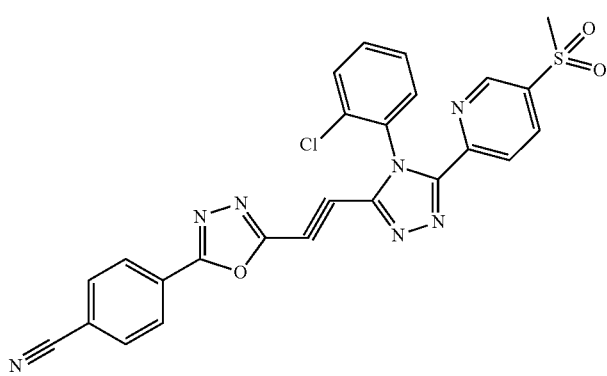 [SMILES: CS(=O)(=O)c1ccc(-c2nnc(C#Cc3nnc(-c4ccc(C#N)cc4)o3)n2-c2ccccc2Cl)nc1] |

| Compound No. | Structre |
|---|---|
| (34) | 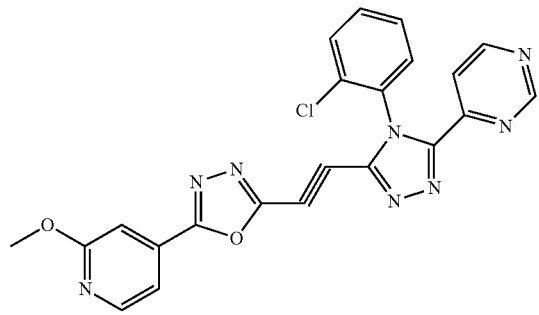 [SMILES: COc1cc(-c2nnc(C#Cc3nnc(-c4ccncn4)n3-c3ccccc3Cl)o2)ccn1] |
| (35) | 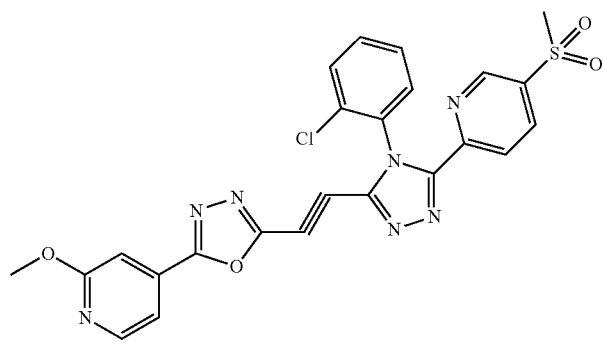 [SMILES: COc1cc(-c2nnc(C#Cc3nnc(-c4ccc(S(C)(=O)=O)cn4)n3-c3ccccc3Cl)o2)ccn1] |
| (36) | 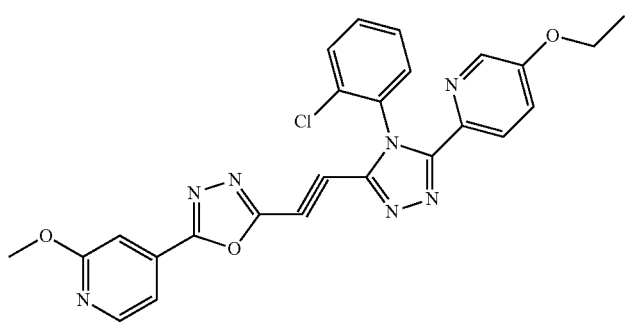 [SMILES: CCOc1ccc(-c2nnc(C#Cc3nnc(-c4ccnc(OC)c4)o3)n2-c2ccccc2Cl)nc1] |
| (37) | 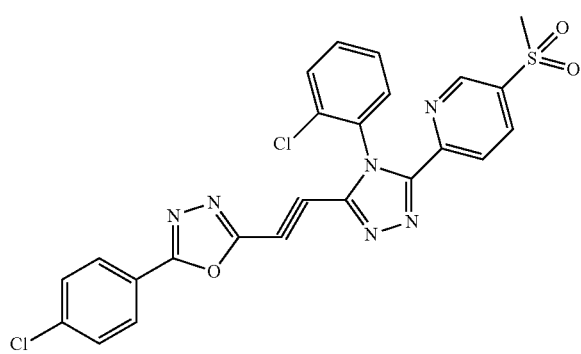 [SMILES: CS(=O)(=O)c1ccc(-c2nnc(C#Cc3nnc(-c4ccc(Cl)cc4)o3)n2-c2ccccc2Cl)nc1] |

| Compound No. | Structre |
|---|---|
| (38) | 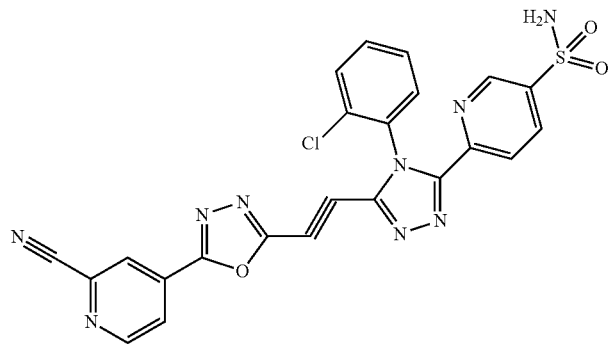 [SMILES: N#Cc1cc(-c2nnc(C#Cc3nnc(-c4ccc(S(N)(=O)=O)cn4)n3-c3ccccc3Cl)o2)ccn1] |
| (39) | 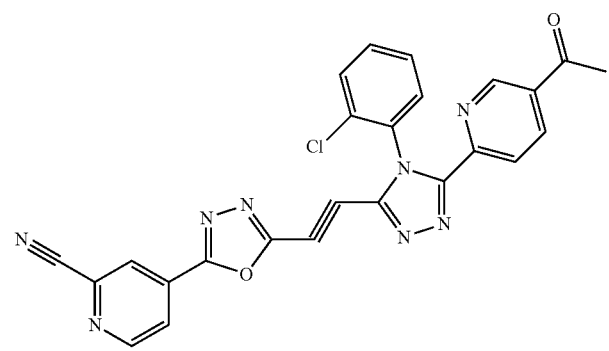 [SMILES: CC(=O)c1ccc(-c2nnc(C#Cc3nnc(-c4ccnc(C#N)c4)o3)n2-c2ccccc2Cl)nc1] |
| (40) | 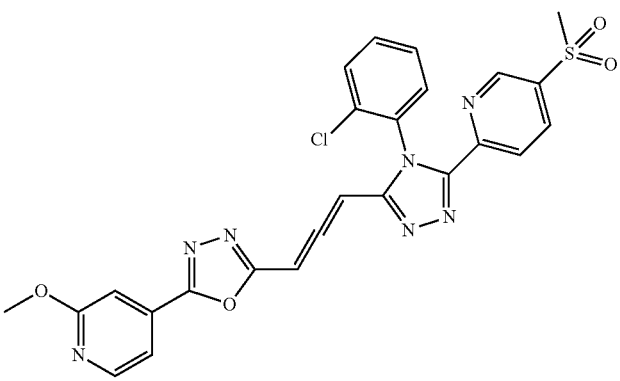 [SMILES: COc1cc(-c2nnc(C=C=Cc3nnc(-c4ccc(S(C)(=O)=O)cn4)n3-c3ccccc3Cl)o2)ccn1] |
| (41) | 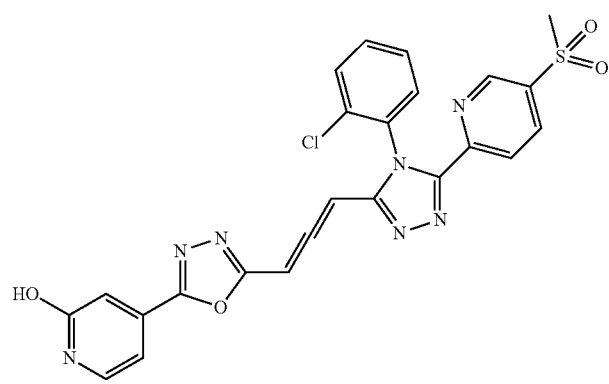 [SMILES: CS(=O)(=O)c1ccc(-c2nnc(C=C=Cc3nnc(-c4ccnc(O)c4)o3)n2-c2ccccc2Cl)nc1] |

| Compound No. | Structre |
|---|---|
| (42) | 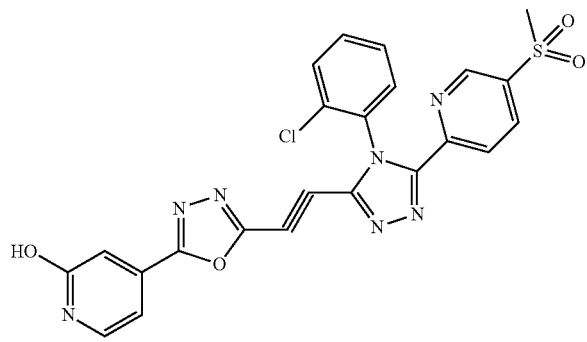 [SMILES: CS(=O)(=O)c1ccc(-c2nnc(C#Cc3nnc(-c4ccnc(O)c4)o3)n2-c2ccccc2Cl)nc1] |
| (43) | 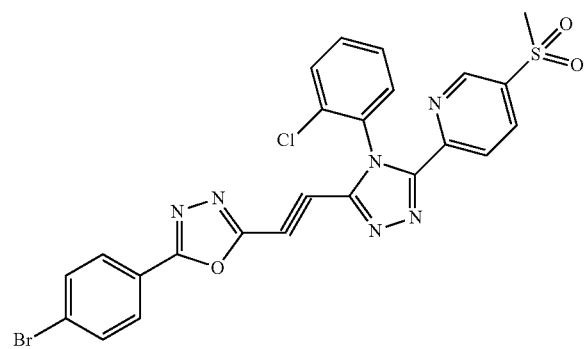 |
| (44) | 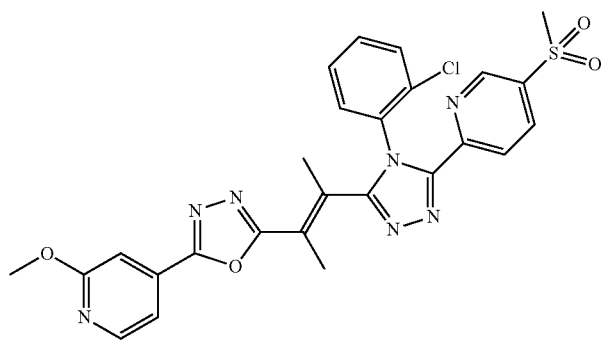 [SMILES: COc1cc(-c2nnc(/C(C)=C(\C)c3nnc(-c4ccc(S(C)(=O)=O)cn4)n3-c3ccccc3Cl)o2)ccn1] |
| (45) | 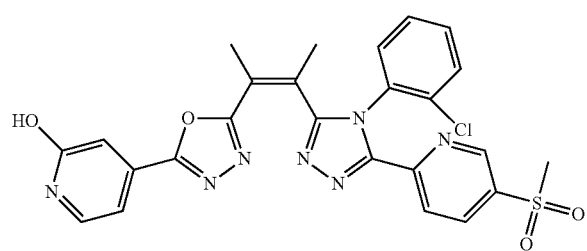 [SMILES: C/C(=C(\C)c1nnc(-c2ccc(S(C)(=O)=O)cn2)n1-c1ccccc1Cl)c1nnc(-c2ccnc(O)c2)o1] |

| Compound No. | Structre |
|---|---|
| (46) | |
| (47) | |
| (48) | |
| (49) | |

| Compound No. | Structre |
|---|---|
| (50) | 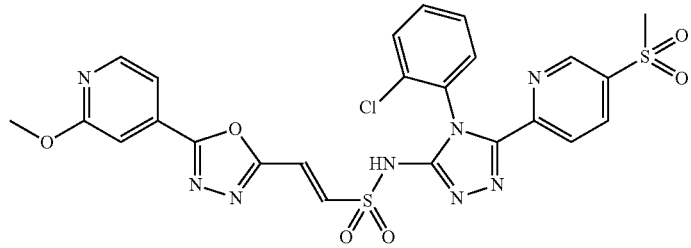 [SMILES: COc1cc(-c2nnc(/C=C/S(=O)(=O)Nc3nnc(-c4ccc(S(C)(=O)=O)cn4)n3-c3ccccc3Cl)o2)ccn1] |
| (51) | 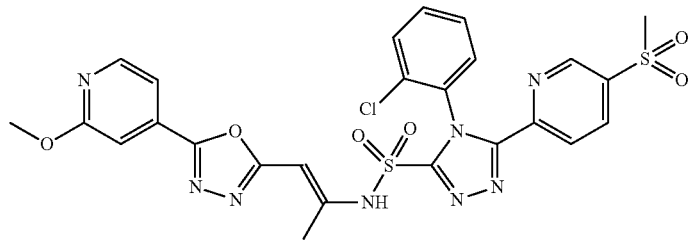 [SMILES: COc1cc(-c2nnc(/C=C(\C)NS(=O)(=O)c3nnc(-c4ccc(S(C)(=O)=O)cn4)n3-c3ccccc3Cl)o2)ccn1] |
| (52) | 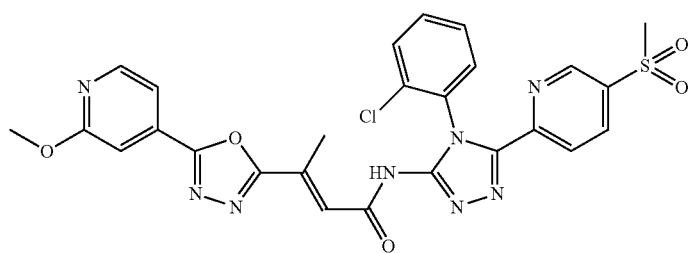 [SMILES: COc1cc(-c2nnc(/C(C)=C/C(=O)Nc3nnc(-c4ccc(S(C)(=O)=O)cn4)n3-c3ccccc3Cl)o2)ccn1] |
| (53) | 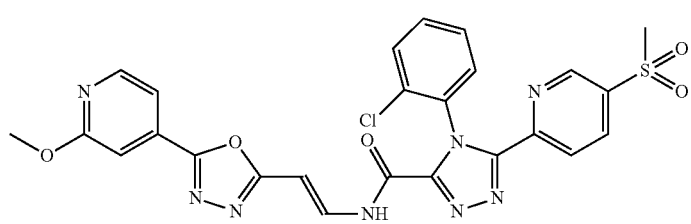 [SMILES: COc1cc(-c2nnc(/C=C/NC(=O)c3nnc(-c4ccc(S(C)(=O)=O)cn4)n3-c3ccccc3Cl)o2)ccn1] |
| (54) | 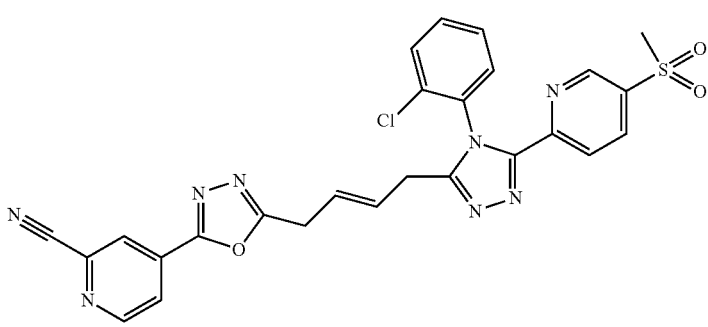 [SMILES: CS(=O)(=O)c1ccc(-c2nnc(C/C=C/Cc3nnc(-c4ccnc(C#N)c4)o3)n2-c2ccccc2Cl)nc1] |

| Compound No. | Structre |
|---|---|
| (55) | 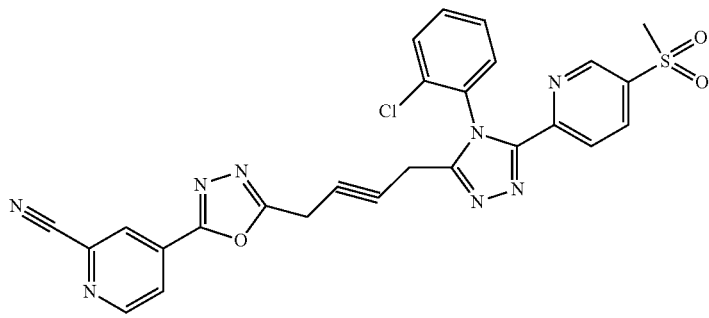 [SMILES: CS(=O)(=O)c1ccc(-c2nnc(CC#CCc3nnc(-c4ccnc(C#N)c4)o3)n2-c2ccccc2Cl)nc1] |
| (56) | 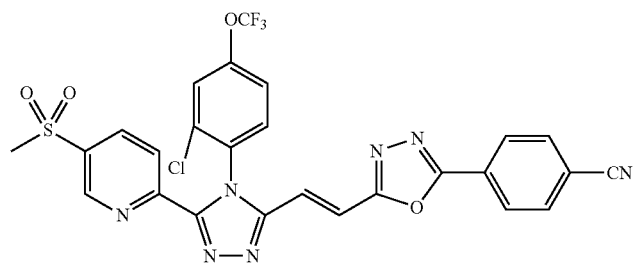 [SMILES: CS(=O)(=O)c1ccc(-c2nnc(/C=C/c3nnc(-c4ccc(C#N)cc4)o3)n2-c2ccc(OC(F)(F)F)cc2Cl)nc1] |
| (57) | 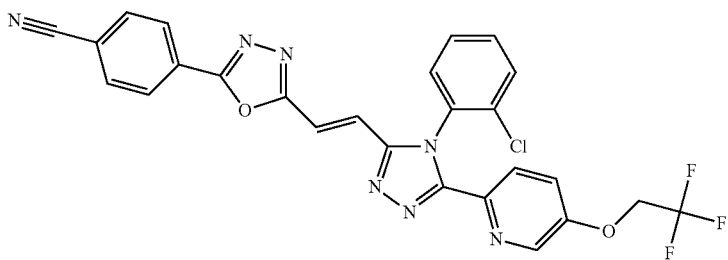 [SMILES: N#Cc1ccc(-c2nnc(/C=C/c3nnc(-c4ccc(OCC(F)(F)F)cn4)n3-c3ccccc3Cl)o2)cc1] |
| (58) | 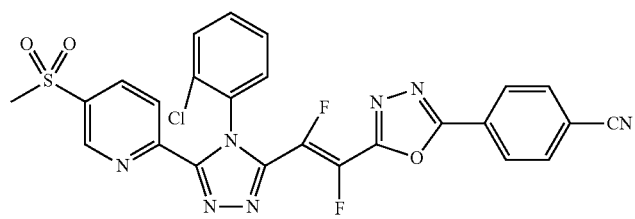 [SMILES: CS(=O)(=O)c1ccc(-c2nnc(/C(F)=C(\F)c3nnc(-c4ccc(C#N)cc4)o3)n2-c2ccccc2Cl)nc1] |

Particularly preferred compounds in accordance with the invention are Compound Nos. (1), (2), (3), (4), (5), (6), (7), (8), (10), (11), (12), (14), (33), (56), (57) and (58), their isomers, pharmaceutically acceptable salts thereof and prodrugs. More particularly preferred compounds in accordance with the invention are Compound Nos. (2), (3), (4), (8), (10), (11), (12), (14) and (57), their isomers, pharmaceutically acceptable salts and prodrugs.

In one embodiment the following compounds per se are excluded from the scope of the invention:

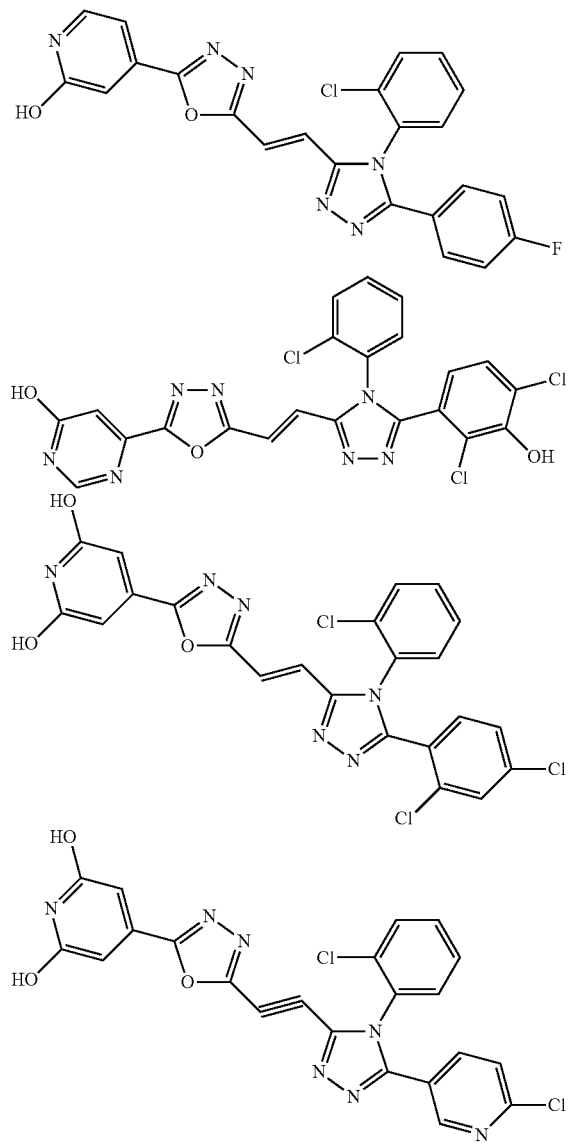

Unless otherwise stated, all substituents are independent of one another.

In the case where a subscript is the integer 0 (i.e. zero), it is intended that the group to which the subscript refers is absent, i.e. there is a direct bond between the groups either side of that particular group.

Unless otherwise stated, any reference herein to a "bond" is intended to refer to a saturated bond.

In the case where an asterisk (*) is present in any of the structural formulae of any of the substituents provided herein, this is to be understood as indicating the point of attachment of that substituent to the remainder of the molecule. Where any of these formulae include two asterisks (denoting two points of attachment), either one of these may be linked to a desired point of attachment on the remainder of the molecule. The orientation of such structures specifically presented herein is not intended to imply that these must be linked in the orientation which is given.

Unless otherwise stated, the term "halo" or "halogen atom" may be fluoro, chloro, bromo, or iodo. Preferably, this is fluoro or chloro.

As used herein, the term "alkyl" refers to a saturated hydrocarbon group and is intended to cover both straight-chained and branched alkyl groups. Examples of such groups include methyl, ethyl, n-propyl, iso-propyl, n-butyl, iso-butyl, sec-butyl, tert-butyl, n-pentyl, iso-pentyl, neo-pentyl, n-hexyl, etc. An alkyl group preferably contains from 1-6 carbon atoms, e.g. 1-4 carbon atoms. Unless otherwise stated, any alkyl group mentioned herein may optionally be substituted by one or more groups, which may be identical or different, for example hydroxy, alkoxy, acyloxy, amino or halogen atoms (e.g. F, Cl or Br).

As used herein, the term "alkenyl" refers to an alkyl group having one or more carbon-carbon double bonds and includes both straight-chained and branched alkenyl groups. The term "$C_{2-6}$ alkenyl" refers to an alkenyl group having from 2 to 6 carbon atoms and one or more (e.g. one or two) double bonds. Examples of such groups include vinyl, allyl, propenyl, iso-propenyl, butenyl, iso-butenyl, crotyl, pentenyl and hexenyl. Unless otherwise stated, any alkenyl group mentioned herein may optionally be substituted by one or more groups, which may be identical or different, for example hydroxy, alkoxy, acyloxy, amino or halogen atoms (e.g. F, Cl or Br).

As used herein, the term "alkynyl" refers to an alkyl group having one or more carbon-carbon triple bonds and includes both straight-chained and branched alkynyl groups. Unless otherwise stated, any alkynyl group mentioned herein may optionally be substituted by one or more groups, which may be identical or different, for example hydroxy, alkoxy, acyloxy, amino or halogen atoms (e.g. F, Cl or Br).

As used herein, the term "haloalkyl" refers to an alkyl group having one or more halo substituents. Examples of such groups include —$CH_2F$, —$CHF_2$, —$CF_3$, —$CCl_3$, —$CHCl_2$, —$CH_2CF_3$, etc.

As used herein, the term "alkylene" refers to a linking alkyl group and is intended to cover any straight-chained or branched alkylene group. Examples of such groups include methylene, ethylene, ethane-1,1-diyl, propylene, propane-2,2-diyl, 1-methylethylene, butylene, 1-methylpropylene, 1,1-dimethylethylene, 1,2-dimethylethylene, etc.

As used herein, the term "unsaturated heterocyclic ring" is intended to cover any 5-, 6- or 7-membered, mono-, di or tri-unsaturated heterocyclic ring which contains at least one heteroatom selected from nitrogen, oxygen and sulphur. The heterocyclic ring structure may be linked to the remainder of the molecule through a carbon atom or, if present, through a nitrogen atom. For example, it may be linked through two carbon atoms, through two nitrogen atoms, or through one carbon and one nitrogen atom. Preferably it will be linked to the remainder of the molecule through two carbon atoms. Unless otherwise stated, any heterocyclic ring mentioned herein may optionally be substituted by one or more groups, which may be identical or different, for example hydroxy, $C_{1-6}$ alkyl, $C_{1-6}$ alkoxy, amino, cyano, nitro or halogen atoms (e.g. F, Cl or Br). A heterocyclic ring may further contain one or more carbonyl or thiocarbonyl functionalities such that this includes oxo and thio-systems.

Illustrative examples of "unsaturated heterocyclic rings" are the heterocycles pyrrole, 2H-pyrrole, furan, pyrroline, thiophene, pyrazole, imidazole, oxazole, isoxazole, pyrazoline, imidazoline, thiazole, isothiazole, thiadiazole, pyridine, 2H-pyran, 4H-pyran, pyridazine, pyrimidine, pyrazine, 1,3-dioxine, 1,4-dioxine and triazole. Of these, thiazole, thiadiazole, pyrimidine, pyridazine, pyrazole, thiophene and triazole are particularly preferred.

As used herein, the term "aryl" is intended to cover aromatic ring systems. Such ring systems may be monocyclic or polycyclic (e.g. bicyclic) and contain at least one unsaturated aromatic ring. Where these contain polycyclic rings, these may be fused. Preferably such systems contain from 6-20 carbon atoms, e.g. either 6 or 10 carbon atoms. Examples of such groups include phenyl, 1-napthyl and 2-napthyl. A preferred aryl group is phenyl. Unless stated otherwise, any "aryl" group may be substituted by one or more substituents, which may be identical or different, for example $C_{1-4}$ alkyl groups, hydroxy, methoxy, trifluoromethoxy and halo groups.

As used herein, the term "heteroaryl" is intended to cover heterocyclic aromatic groups. Such groups may be monocyclic or bicyclic and contain at least one unsaturated heteroaromatic ring system. Where these are monocyclic, these comprise 5- or 6-membered rings which contain at least one heteroatom selected from nitrogen, oxygen and sulphur and contain sufficient conjugated bonds to form an aromatic system. Where these are bicyclic, these may contain from 9-11 ring atoms. Examples of heteroaryl groups include thiophene, thienyl, pyridyl, thiazolyl, furyl, pyrrolyl, triazolyl, imidazolyl, oxadiazolyl, oxazolyl, pyrazolyl, imidazolonyl, oxazolonyl, thiazolonyl, tetrazolyl, thiadiazolyl, benzimidazolyl, benzooxazolyl, benzofuryl, indolyl, isoindolyl, pyridonyl, pyridazinyl, pyrimidinyl, imidazopyridyl, oxazopyridyl, thiazolopyridyl, imidazopyridazinyl, oxazolopyridazinyl, thiazolopyridazinyl and purinyl. Unless stated otherwise, any "heteroaryl" may be substituted by one or more substituents, which may be identical or different, for example $C_{1-4}$ alkyl groups, hydroxy, methoxy, trifluoromethoxy and halo groups.

The term "prodrug" is intended to encompass any compound which under physiological conditions is converted into any of the compounds herein described, i.e. a compound of formula I, II, Ia, IIa, Ib, IIb, IIc or IId. Suitable prodrugs include compounds which are hydrolysed under physiological conditions to the desired molecule.

The compounds according to the invention may be prepared from readily available starting materials using synthetic methods known in the art. Preferably, the compounds are obtained in accordance with the following methods which form part of the invention:

(a) reacting a compound of general formula III:

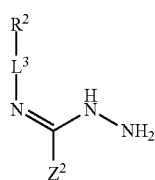

(III)

(wherein $Z^2$, $R^2$ and $L^3$ are as hereinbefore defined)

with a compound of general formula IV:

(IV)

(wherein $R^1$, $Z^1$ and $L^1$ are as hereinbefore defined and L denotes a leaving group such as a halogen atom, e.g. Cl).

The reaction is conveniently carried out in a solvent or mixture of solvents, such as for example a polar solvent such as acetonitirile, acetone, DMF, DMSO or dioxane, in the presence of a dehydrating agent such as phosphoryl chloride, expediently at temperatures up to 150° C., preferably at temperatures between −20 and 80° C.

(b) reacting a compound of general formula III:

(III)

(wherein $Z^2$, $R^2$ and $L^3$ are as hereinbefore defined) with a compound of general formula V:

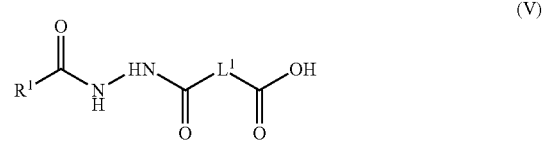

(V)

(wherein $R^1$ and $L^1$ are as hereinbefore defined).

The reaction is conveniently carried out in a solvent or mixture of solvents, such as for example a polar solvent such as acetonitirile, acetone, DMF, DMSO or dioxane, in the presence of a dehydrating agent such as phosphoryl chloride, expediently at temperatures up to 150° C., preferably at temperatures between −20 and 80° C.

(c) if desired, resolving a compound thus obtained into the stereoisomers thereof; and/or (d) converting a compound thus obtained into a salt thereof, particularly a pharmaceutically acceptable salt thereof.

The compounds used as starting materials are either known from the literature or may be commercially available. Alternatively, these may be obtained by methods known from the literature.

The invention includes all optical isomers and stereoisomers of the compounds herein disclosed. In particular, the invention extends to the enantiomers of any of the compounds having a chiral centre in the group $L^1$.

The compounds of general formulae I, II, Ia, IIa, Ib, IIb, IIc or IId may be resolved into their enantiomers and/or diastereomers. For example, where these contain only one chiral centre, these may be provided in the form of a racemate or may be provided as pure enantiomers, i.e. in the R- or S-form. Any of the compounds which occur as racemates may be separated into their enantiomers by methods known in the art, such as column separation on chiral phases or by recrystallisation from an optically active solvent. Those compounds with at least two asymmetric carbon atoms may be resolved into their diastereomers on the basis of their physical-chemical differences using methods known per se, e.g. by chromatography and/or fractional crystallisation, and where these compounds are obtained in racemic form, they may subsequently be resolved into the enantiomers.

The invention further includes certain structural isomers of the compounds herein disclosed. In particular, the invention extends to tautomers of any of the compounds. As will be appreciated, certain compounds according to the invention may exist in tautomeric forms, i.e. in forms which readily interconvert by way of a chemical reaction which may involve the migration of a proton accompanied by a switch of a single bond and adjacent double bond. In cases where one of the groups $R_e$ and $R_f$ is hydroxyl the compounds of the invention may, in particular, undergo keto-enol tautomerism. Dependent on the conditions, the compounds may predominantly exist either in the keto or enol form and the invention is not intended to be limited to the particular form shown in any of the structural formulae given herein.

The compounds according to the invention may be converted into a salt thereof, particularly into a pharmaceutically acceptable salt thereof with an inorganic or organic acid or base. Acids which may be used for this purpose include hydrochloric acid, hydrobromic acid, sulphuric acid, sulphonic acid, methanesulphonic acid, phosphoric acid, fumaric acid, succinic acid, lactic acid, citric acid, tartaric acid, maleic acid, acetic acid, trifluoroacetic acid and ascorbic acid. Bases which may be suitable for this purpose include alkali and alkaline earth metal hydroxides, e.g. sodium hydroxide, potassium hydroxide or cesium hydroxide, ammonia and organic amines such as diethylamine, triethylamine, ethanolamine, diethanolamine, cyclohexylamine and dicyclohexylamine. Procedures for salt formation are conventional in the art.

In a further aspect there is provided pharmaceutical formulations comprising a compound of formula I, II, Ia, IIa, Ib, IIb, IIc or IId as herein defined, or a pharmaceutically acceptable salt thereof, together with one or more pharmaceutically acceptable carriers or excipients.

The compounds according to the invention and their pharmaceutically acceptable salts have valuable pharmacological properties, particularly an inhibitory effect on β-catenin. In view of their ability to inhibit signaling in the Wnt pathway, and in particular to reduce the levels of nuclear β-catenin, the compounds according to the invention and their pharmaceutically acceptable salts are suitable for the treatment and/or prevention of any condition or disease which may be affected by over-activation of signaling in the Wnt pathway, in particular those conditions or diseases which involve activation of β-catenin.

The term "Wnt signaling pathway" is used to refer to the chain of events normally mediated by Wnt, LRP (LDL-receptor related protein), Frizzled and β-catenin, among others, and resulting in changes in gene expression and other phenotypic changes typical of Wnt activity.

The Wnt pathway plays a central role in the pathology of a variety of cancers. The compounds of the invention are thus particularly suitable for preventing and/or retarding proliferation and metastasis of tumor cells, in particular carcinomas such as adenocarcinomas. More specifically, the compounds are effective in treatment and/or prevention of the following cancers: colon cancers (such as colorectal cancer), pancreatic cancer (e.g. pancreas adenocarcinoma), gastric cancer, liver cancers (e.g. hepatocellular and hepatoblastoma carcinomas), Wilms tumor of the kidney, medulloblastoma, skin cancers (e.g. melanoma), non-small cell lung cancer, cervical cancer, ovarian cancers (e.g. ovarian endometrial cancer), bladder cancer, thyroid cancers (e.g. anaplastic thyroid cancer), head and neck cancer, breast cancer, prostate cancer and glioblastoma. Particularly preferably, the compounds herein described may be used in the treatment and/or prevention of breast cancer, non-small cell lung cancer, ovarian, thyroid, colorectal, pancreatic and prostate cancers and glioblastoma. Treatment or prevention of breast, non-small cell lung, pancreatic and colorectal cancers represents a particularly preferred aspect of the invention.

As used herein, the term "proliferation" refers to cells undergoing mitosis. The term "retarding proliferation" indicates that the compounds inhibit proliferation of a cancer cell. In preferred embodiments, "retarding proliferation" indicates that DNA replication is at least 10% less than that observed in untreated cells, more preferably at least 25% less, yet more preferably at least 50% less, e.g. 75%, 90% or 95% less than that observed in untreated cancer cells.

The term "carcinoma" refers to any malignant growth which arises from epithelial cells. Exemplary carcinomas include basal cell carcinoma, squamous cell carcinoma and adenocarcinoma. Adenocarcinomas are malignant tumors originating in the glandular epithelium and include colorectal, pancreatic, breast and prostate cancers.

Viewed from a further aspect the invention thus provides a compound of formula I, II, Ia, IIa, Ib, IIb, IIc or IId, or a pharmaceutically acceptable salt thereof, for use in therapy.

Unless otherwise specified, the term "therapy" as used herein is intended to include both treatment and prevention.

In a still further aspect the invention provides a compound of formula I, II, Ia, IIa, Ib, IIb, IIc or IId, or a pharmaceutically acceptable salt thereof, for use in the treatment or prevention of colon cancers (such as colorectal cancer), pancreatic cancer, gastric cancer, liver cancers (e.g. hepatocellular and hepatoblastoma carcinomas), Wilms tumor of the kidney, medulloblastoma, skin cancers (e.g. melanoma), non-small cell lung cancer, cervical cancer, ovarian endometrial cancer, bladder cancer, anaplastic thyroid cancer, head and neck cancer, breast cancer, prostate cancer or glioblastoma.

In another aspect the invention provides the use of a compound of formula I, II, Ia, IIa, Ib, IIb, IIc or IId or a pharmaceutically acceptable salt thereof, in the manufacture of a medicament for use in a method of treatment or prevention of colon cancers (such as colorectal cancer), pancreatic cancer, gastric cancer, liver cancers (e.g. hepatocellular and hepatoblastoma carcinomas), Wilms tumor of the kidney, medulloblastoma, skin cancers (e.g. melanoma), non-small cell lung cancer, cervical cancer, ovarian endometrial cancer, bladder cancer, anaplastic thyroid cancer, head and neck cancer, breast cancer, prostate cancer or glioblastoma.

Also provided is a method of treatment of a human or non-human animal body to combat or prevent colon cancers (such as colorectal cancer), pancreatic cancer, gastric cancer, liver cancers (e.g. hepatocellular and hepatoblastoma carcinomas), Wilms tumor of the kidney, medulloblastoma, skin cancers (e.g. melanoma), non-small cell lung cancer, cervical cancer, ovarian endometrial cancer, bladder cancer, anaplastic thyroid cancer, head and neck cancer, breast cancer, prostate cancer or glioblastoma, said method comprising the step of administering to said body an effective amount of a compound of formula I, II, Ia, IIa, Ib, IIb, IIc or IId as herein defined or a pharmaceutically acceptable salt thereof.

Small molecules that selectively target the developmental pathways which control pattern formation during embryogenesis, including Wnt signalling pathways, are considered to be valuable for directing differentiation of pluripotent stem cells toward many desired tissue types (see Wang et al., ACS Chemical Biology, 16 Nov. 2010). As modulators of Wnt signalling, the compounds herein described also have effects on the development of cellular differentiation. The compounds described herein therefore have valuable properties for use in regenerative medicine, for example in protocols for lineage specific in vitro differentiation of progenitor cells. By "progenitor cell" is meant a cell with the capacity to differentiate into another cell type, e.g. a stem cell.

According to this aspect, the present invention provides a method (e.g. an in vitro method) of promoting and/or directing cellular differentiation comprising contacting a progenitor cell with an effective amount of a compound of formula I, II, Ia, IIa, Ib, IIb, IIc or IId as herein defined or a pharmaceutically acceptable salt thereof. In particular, the progenitor cell is contacted with said at least one compound under suitable conditions and for a sufficient time for the progenitor cell to differentiate into a new cell type. In a related aspect, the present invention provides the use of at least one compound as herein defined for promoting and/or directing cellular differentiation of a progenitor cell, especially in vitro.

Preferably, the progenitor cell is a totipotent or a pluripotent cell, especially a stem cell such as an embryonic stem cell. Preferred are mammalian progenitor cells such as mouse, rat and human cells, especially human cells. Such stem cells may be obtained from established cell cultures or may be derived directly from mammalian tissue by methods known in the art, including non tissue-destructive methods.

In a preferred embodiment, the progenitor cell is promoted and/or directed to differentiate into a new cell type which is a myocyte (e.g. a cardiomyocyte), a neuronal cell (e.g. a dopaminergic neuronal cell), an endocrine pancreatic cell or a hepatocyte or a cell type which may further differentiate into a myocyte, a neuronal cell, an endocrine pancreatic cell or a hepatocyte. Especially preferably, the progenitor cell is an embryonic stem cell and the new cell type is a cardiomyocyte, a dopaminergic neuronal cell, an endocrine pancreatic cell or a hepatocyte, especially a cardiomyocyte.

The dosage required to achieve the desired activity of the compounds herein described will depend on the compound which is to be administered, the patient, the nature and severity of the condition, the method and frequency of administration and may be varied or adjusted according to choice. Typically, the dosage may be expected to be in the range from 1 to 100 mg, preferably 1 to 30 mg (when administered intravenously) and from 1 to 1000 mg, preferably from 1 to 200 mg (when administered orally).

The compounds of the invention may be formulated with one or more conventional carriers and/or excipients according to techniques well known in the art. Typically, the compositions will be adapted for oral or parenteral administration, for example by intradermal, subcutaneous, intraperitoneal or intravenous injection. Suitable pharmaceutical forms thus include plain or coated tablets, capsules, suspensions and solutions containing the active component optionally together with one or more conventional inert carriers and/or diluents, such as corn starch, lactose, sucrose, microcrystalline cellulose, magnesium stearate, polyvinylpyrrolidone, citric acid, tartaric acid, water, water/ethanol, water/glycerol, water/sorbitol, water/polyethyleneglycol, propylene glycol, stearylalcohol, carboxymethylcellulose or fatty substances such as hard fat or suitable mixtures of any of the above.

The pharmacological properties of the compounds of the invention can be analysed using standard assays for functional activity. Detailed protocols for testing of the compounds of the invention are provided in the Examples.

The invention will now be described in more detail in the following non-limiting Examples and Figures, in which.

Figure 1:
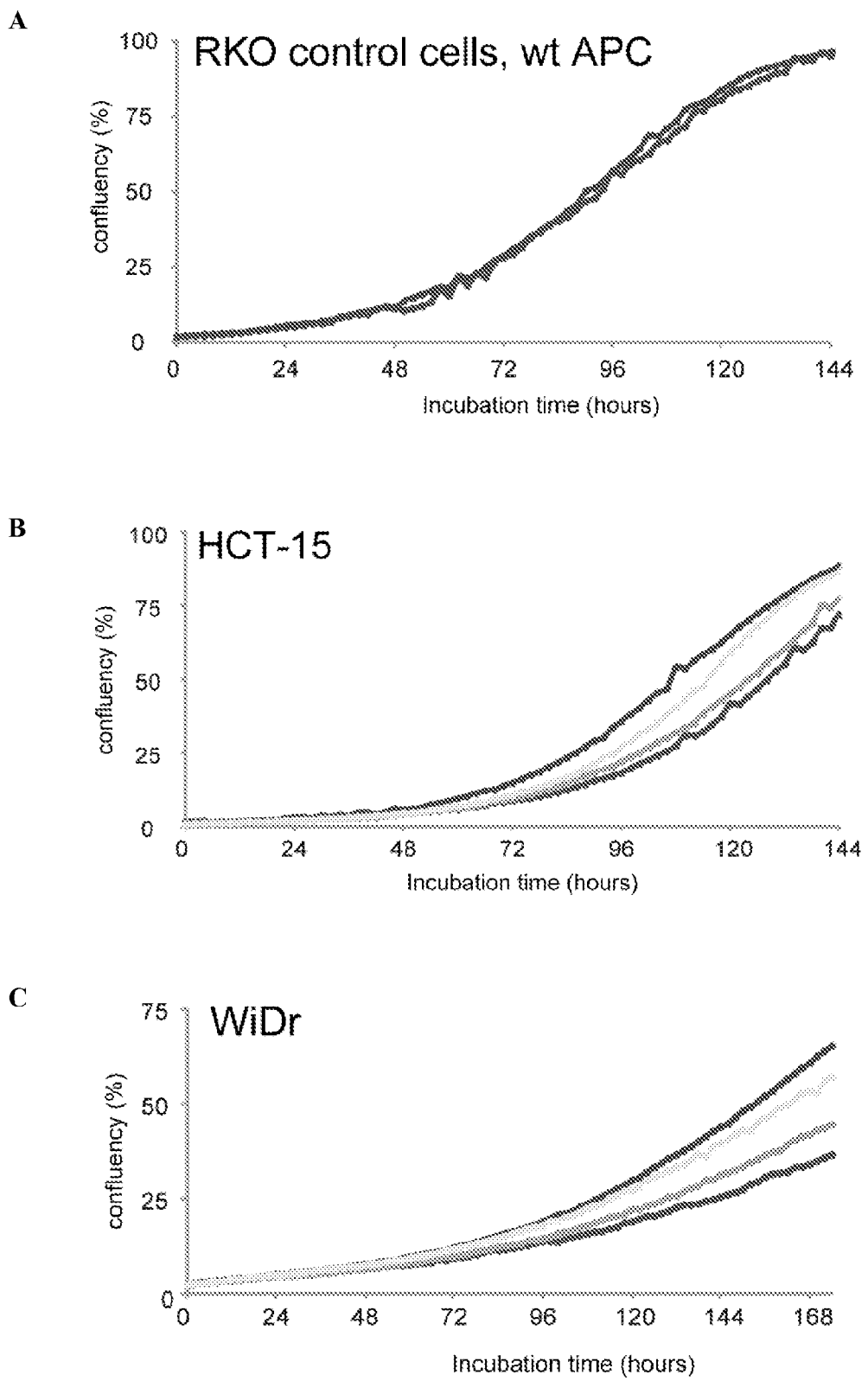
FIG. 1 shows the effect of a compound of the invention on cell growth in RKO, HCT-15, WiDr, HT29, DLD-1, COLO320DM and COL0205 cells (FIGS. 1A to 1G, respectively)
Figure 1:
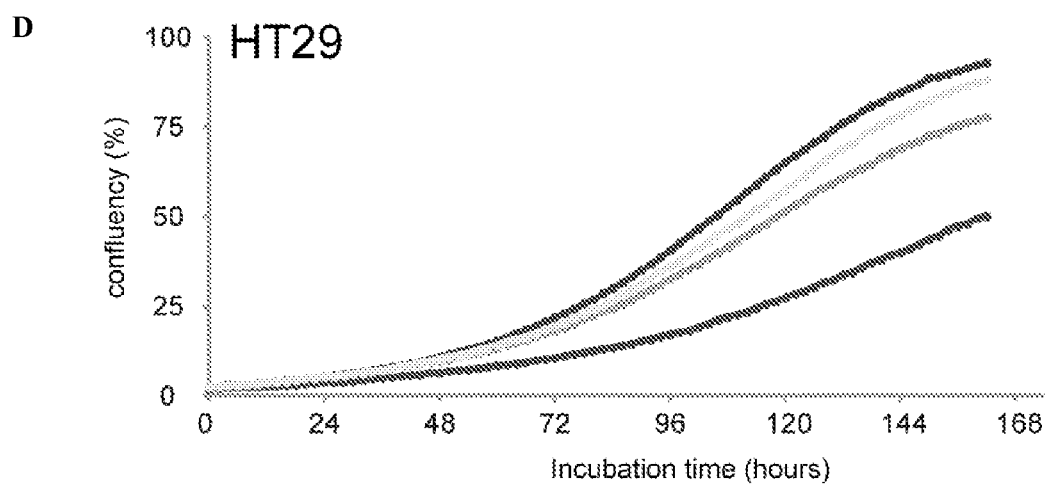
Figure 1:
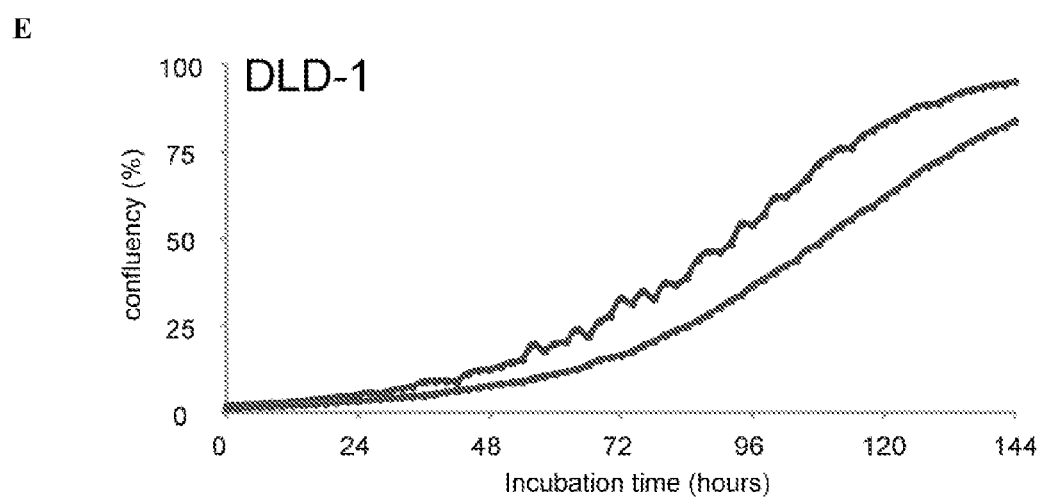
Figure 1:
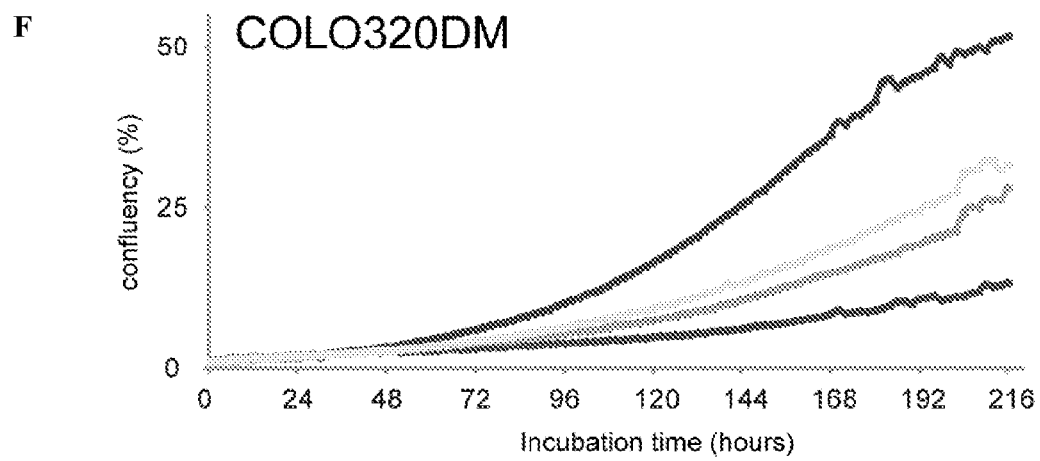
Figure 1:
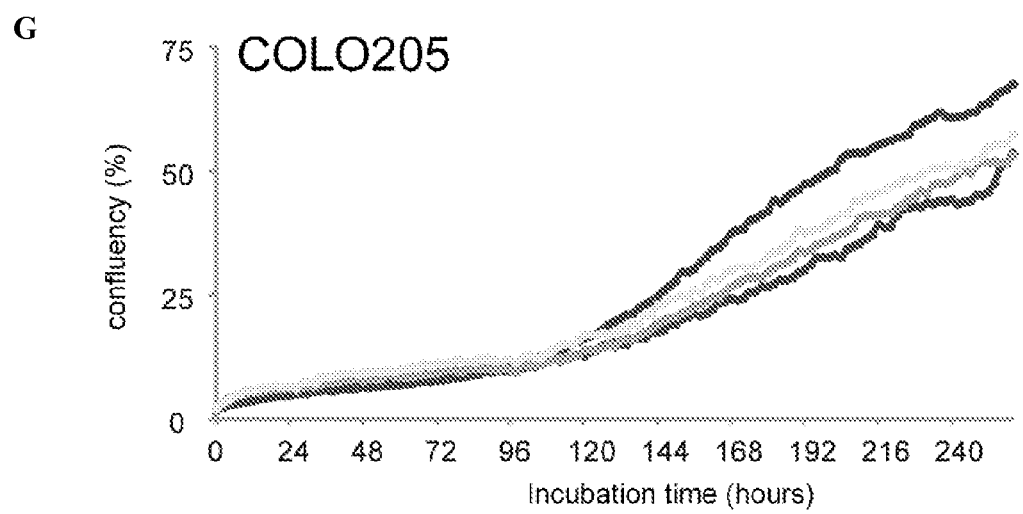

Examples 6 to 9 are examples of formulations in which reference to the "active substance" denotes one or more compounds according to the invention, including the salts thereof.

EXAMPLE 1

Preparation of 4-(5-((E)-2-(5-(2,4-dichlorophenyl)-4-(2-chlorophenyl)-4H-1,2,4-triazol-3-yl)vinyl)-1,3,4-oxadiazol-2-yl)-2-methoxypyridine (Compound (1))

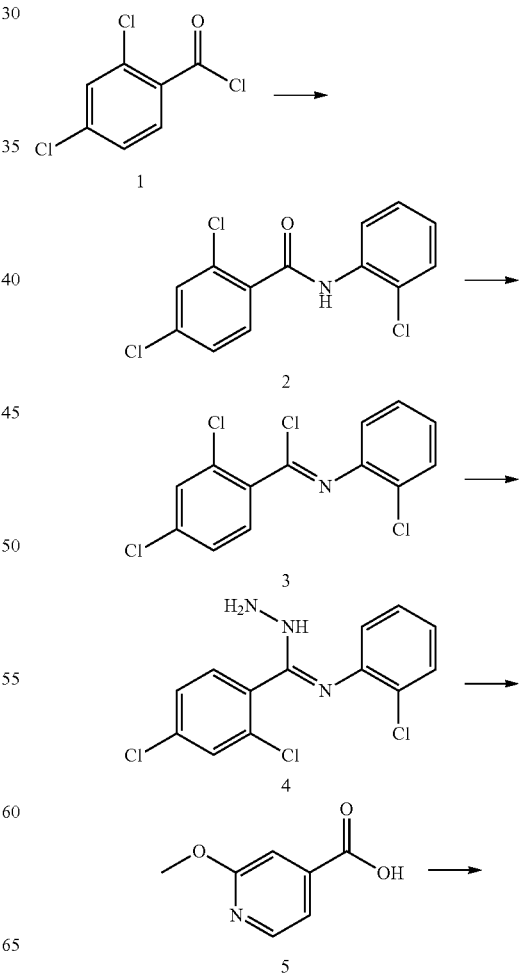

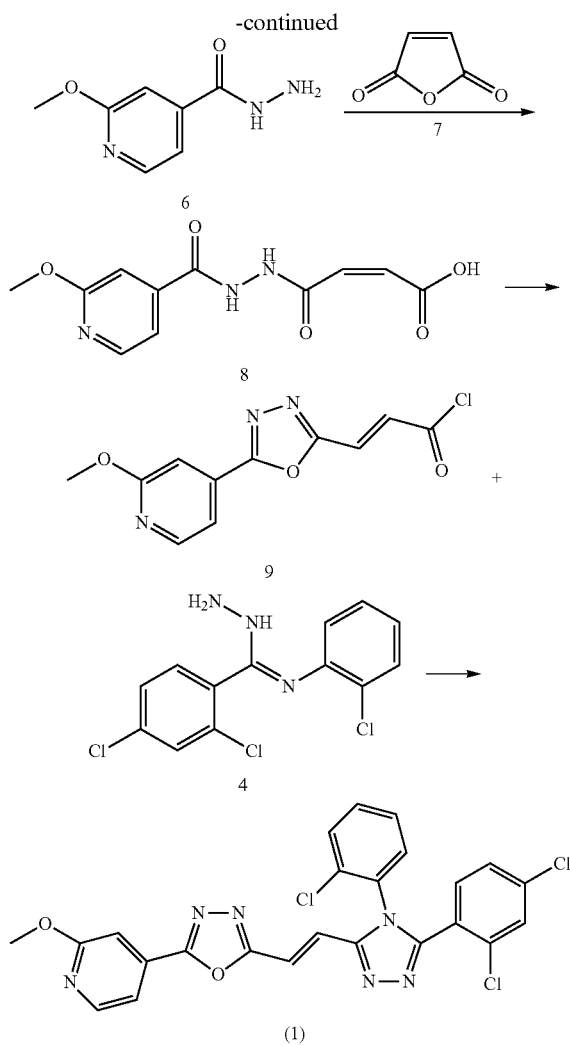

was added (20 mL) followed by hydrazine monohydrate (5.0 mL) and the reaction mixture was further stirred at ambient temperature for 3 hours. After the solvent was removed, the residue was mixed with ether:hexane (1:1, 30 mL), the solid was filtered and further washed with ether:hexane mixture to yield a pure solid as N-amino-2,4-dichloro-N'-(2-chlorophenyl)benzamidine 4. Yield: 4.4 g, 70%.

$^1$H-NMR (300 Hz, CDCl$_3$) δ (ppm): 7.43 (d, 1 H), 7.38-7.22 (m, 3H), 6.98 (dd, 1 H), 6.82 (dd, 1H), 6.41 (d, 1 H).

(c) Preparation of 2-methoxyisonicotinohydrazide 6

To a solution of 2-methoxypyridine-4-carboxylic acid 5 (1.0 g, 6.5 mmol) in CH$_3$OH (30 mL) was added a few drops of SOCl$_2$ at ambient temperature. The mixture was stirred under reflux for 16 hours and concentrated to give the ester. To the solution of the ester in CH$_3$OH was added hydrazine monohydrate (2.0 mL, 37 mmol) at ambient temperature. The reaction mixture was stirred at ambient temperature for 16 hours and concentrated to give 2-methoxyisonicotinohydrazide 6 as a white solid. Yield: 0.87 g, 80%.

$^1$H-NMR (300 MHz, DMSO-d$_6$) δ (ppm): 10.0 (bs, 1H), 8.25 (dd, 1 H), 7.31 (dd, 1 H), 7.13 (s, 1H), 4.66 (bs, 2 H), 3.86 (s, 3 H).

(d) Preparation of (Z)-4-(2-methoxypyridine-4-carboamido)-4-oxobut-2-enoic acid 8

To a solution of 2-methoxyisonicotinohydrazide 6 (0.80 g, 4.89 mmol) in THF (20 mL) was added malenic anhydride 7 (0.47 g, 4.79 mmol). The mixture was stirred at ambient temperature for 16 hours. The solid was filtered and dried under vacuum to afford the pure compound (Z)-4-(2-methoxypyridine-4-carboamido)-4-oxobut-2-enoic acid 8 as a white solid. Yield: 1.02 g, 80%.

$^1$H-NMR (300 MHz, DMSO-d$_6$) δ (ppm): 8.32 (d, 1 H), 7.38 (d, 1 H), 7.22 (s, 1 H), 6.38 (dd, 2H), 3.90 (s, 3 H), 3.40 (bs, 3 H).

(a) Preparation of 2,4-dichloro-N-(2-chlorophenyl)benzamide 2

To a solution of 2-chloroaniline (5.15 g, 40.37 mmol) in dichloromethane (50 mL) was added 2,4-dichlorobenzoyl chloride 1 (8.88 g, 42.39 mmol) and then triethylamine (6.1 mL, 44 mmol). The reaction mixture was stirred overnight at ambient temperature and ethyl acetate (150 mL) was added followed by 1N HCl (50 mL). The organic phase was washed with water and brine, dried, and concentrated under reduced pressure to yield a light yellow solid. 2,4-dichloro-N-(2-chlorophenyl)benzamide 2 was used for the next step without further purification. Yield: 11 g, 90%.

$^1$H-NMR (300 Hz, CDCl$_3$) δ (ppm): 8.52 (dd, 2 H), 7.62 (d, 1 H), 7.52 (s, 1 H), 7.38-7.22 (m, 3H), 7.08 (d, 1 H).

(b) Preparation of N'-(2-chlorophenyl)-4-fluorobenzimidohydrazide 4

A mixture of 2,4-dichloro-N-(2-chlorophenyl)benzamide 2 (6.0 g, 20 mmol) and PCl$_5$ (4.58 g, 22 mmol) in benzene (40 mL) was stirred under reflux for 16 hours. The solvent was removed and further dried under high vacuum. The residue 2-chloro-N-(chloro(2,4-dichlorophenyl)methylene)benzenamine 3 was cooled down by ice water bath. Anhydrous THF (e) Preparation of 4-(5-((E)-2-(5-(2,4-dichlorophenyl)-4-(2-chlorophenyl)-4H-1,2,4-triazol-3-yl)vinyl)-1,3,4-oxadiazol-2-yl)-2-methoxypyridine (Compound (1))

To a suspension of (Z)-4-(2-methoxypyridine-4-carboamido)-4-oxobut-2-enoic acid 8 (0.2 g, 0.75 mmol) in CH$_3$CN was added POCl$_3$ (0.37 g, 2.4 mmol). The mixture was stirred under reflex for 16 hours, cooled to ambient temperature and concentrated under reduced pressure. The residue was dissolved in CH$_3$CN, treated with a solution of N-amino-2,4-dichloro-N'-(2-chlorophenyl)benzamidine 4 (0.38 g, 1.2 mmol) in CH$_3$CN and K$_2$CO$_3$ (0.38 g, 1.2 mmol). The mixture was stirred at ambient temperature for 1 hour, refluxed for 2 hours and filtered. The filtrate was concentrated. The residue was subjected to flash column chromatography (FCC) (50-60% EtOAc/hexanes) to afford the title compound 4-(5-((E)-2-(5-(2,4-dichlorophenyl)-4-(2-chlorophenyl)-4H-1,2,4-triazol-3-yl)vinyl)-1,3,4-oxadiazol-2-yl)-2-methoxypyridine as a white solid. Yield: 0.11 g, 28%.

$^1$H-NMR (300 Hz, CDCl$_3$) δ (ppm): 8.38 (d, 1 H), 7.62-7.18 (m, 11 H), 4.03 (s, 3 H).

MS (M+1) 525.3.

HPLC (Waters 625 LC System): 95%.

EXAMPLE 2

Preparation of 4-(5-((E)-2-(4-(2-chlorophenyl)-5-(4-(methylsulfonyl)phenyl)-4H-1,2,4-triazol-3-yl)vinyl)-1,3,4-oxadiazol-2-yl)-2-methoxypyridine (Compound (2))

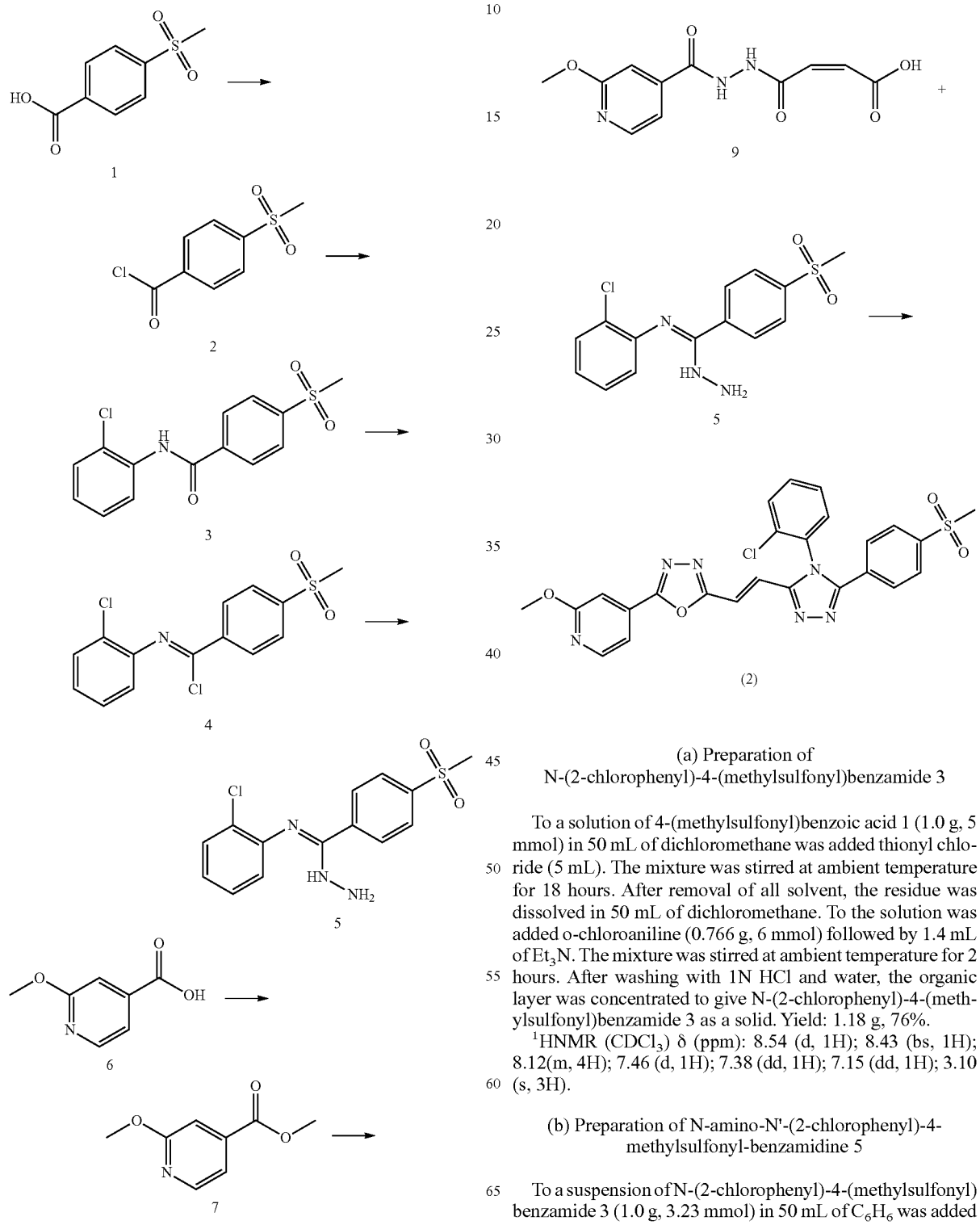

(a) Preparation of N-(2-chlorophenyl)-4-(methylsulfonyl)benzamide 3

To a solution of 4-(methylsulfonyl)benzoic acid 1 (1.0 g, 5 mmol) in 50 mL of dichloromethane was added thionyl chloride (5 mL). The mixture was stirred at ambient temperature for 18 hours. After removal of all solvent, the residue was dissolved in 50 mL of dichloromethane. To the solution was added o-chloroaniline (0.766 g, 6 mmol) followed by 1.4 mL of $Et_3N$. The mixture was stirred at ambient temperature for 2 hours. After washing with 1N HCl and water, the organic layer was concentrated to give N-(2-chlorophenyl)-4-(methylsulfonyl)benzamide 3 as a solid. Yield: 1.18 g, 76%.

$^1$HNMR (CDCl$_3$) δ (ppm): 8.54 (d, 1H); 8.43 (bs, 1H); 8.12(m, 4H); 7.46 (d, 1H); 7.38 (dd, 1H); 7.15 (dd, 1H); 3.10 (s, 3H).

(b) Preparation of N-amino-N'-(2-chlorophenyl)-4-methylsulfonyl-benzamidine 5

To a suspension of N-(2-chlorophenyl)-4-(methylsulfonyl) benzamide 3 (1.0 g, 3.23 mmol) in 50 mL of $C_6H_6$ was added 10 mL of POCl$_3$. The mixture was refluxed for 15 hours. After removal of solvent, the residue was dissolved in 50 mL of THF and 3 mL of H$_2$NNH$_2$.H$_2$O added. The mixture was stirred at ambient temperature for 2 hours. After removal of solvent, the residue was purified by column (2-5% methanol in dichloromethane) to give N-amino-N'-(2-chlorophenyl)-4-methylsulfonyl-benzamidine 5 as a solid. Yield: 0.8 g, 77%.

$^1$HNMR (CDCl$_3$) δ (ppm): 7.90 (d, 2H); 7.75 (d, 2H); 7.40 (d, 1H); 7.05 (dd, 1H); 6.85 (dd, 1H); 6.40 (d, 1H); 5.95 (br, 1H); 5.70 (br, 2H); 3.3.05 (s, 3H).

(c) Preparation of 2-methoxypyridine-4-carbohydrazide 8

To a solution of 2-methoxypyridine-4-carboxylic acid 6 (2.0 g, 13 mmol) in 30 mL of MeOH was added 3 mL of thionyl chloride. The mixture was stirred under reflux for 2 hours. After removal of the solvent, the residue was dissolved in 30 mL of THF and 3 mL of H$_2$NNH$_2$.H$_2$O added. The mixture was heated at reflux for 0.5 hours. After removal of solvent, the residue was purified by column (5-10% of methanol in dichloromethane) to give 2-methoxypyridine-4-carbohydrazide 8 as a solid. Yield: 1.76 g, 81%.

$^1$HNMR (DMSO-d$_6$) δ (ppm): 9.98 (s, 1H); 8.25 (d, 1H); 7.30 (d, 1H); 7.13 (s, 1H); 4.57 (s, 2H); 3.86 (s, 3H).

(d) Preparation of (Z)-4-(2-methoxypyridine-4-carboamido)-4-oxobut-2-enoic acid 9

To a solution of compound 8 (167 mg, 1.0 mmol) in 10 mL of THF was added furan-2,5-dione (110 mg, 1.1 mmol). The mixture was stirred at ambient temperature for 2 hours. After removal of the solvent, the residue was diluted with 10 mL of dichloromethane. The solid was collected by filtration to give (Z)-4-(2-methoxypyridine-4-carboamido)-4-oxobut-2-enoic acid 9 as a solid.

Yield: 190 mg, 71%.

$^1$HNMR (DMSO-d$_6$) δ (ppm): 10.45 (s, 2H); 8.32 (d, 1H); 7.36 (d, 1H); 7.20 (s, 1H); 6.41 (d, 1H); 6.29 (d, 1H); 3.90 (s, 3H).

(e) Preparation of 4-(5-((E)-2-(4-(2-chlorophenyl)-5-(4-(methylsulfonyl)phenyl)-4H-1,2,4-triazol-3-yl)vinyl)-1,3,4-oxadiazol-2-yl)-2-methoxypyridine (Compound (2))

To a suspension of (Z)-4-(2-methoxypyridine-4-carboamido)-4-oxobut-2-enoic acid 9 (180 mg, 0.68 mmol) in 20 mL of PhMe was added 0.2 mL of POCl$_3$. The mixture was stirred at reflux for 2 hours. After removal of solvent, the residue was dissolved in 20 mL of THF and 220 mg (0.68 mmol) of N-amino-N'-(2-chlorophenyl)-4-methylsulfonyl-benzamidine 5 added. The mixture was stirred at ambient temperature for 18 hours. After removal of solvent, the residue was purified by column (0-5% of methanol in dichloromethane) to give 4-(5-((E)-2-(4-(2-chlorophenyl)-5-(4-(methylsulfonyl)phenyl)-4H-1,2,4-triazol-3-yl)vinyl)-1,3,4-oxadiazol-2-yl)-2-methoxypyridine as a solid. Yield: 30 mg, 8.3%.

$^1$HNMR (CDCl$_3$) δ (ppm): 8.32 (d, 1H); 7.90 (d, 2H); 7.80-7.40 (m, 8H); 7.32 (m, 1H); 7.10 (d, 1H); 4.00 (s, 3H); 3.3.05 (s, 3H).

MS (M+1) 535.1.
HPLC (Waters 625 LC System): 96%.

EXAMPLE 3

Preparation of 4-(4-(2-chlorophenyl)-5-((E)-2-(5-(2-methoxypyridin-4-yl)-1,3,4-oxadiazol-2-yl)vinyl)-4H-1,2,4-triazol-3-yl)pyridine (Compound (3))

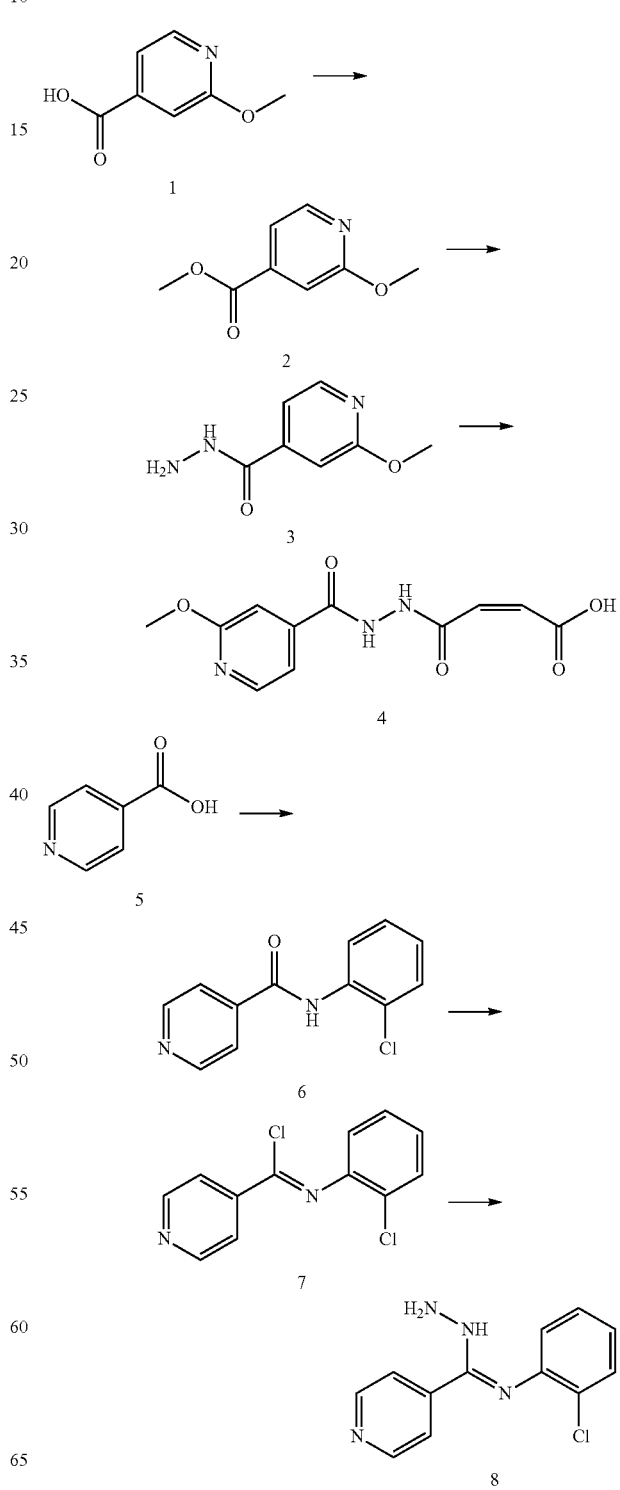

-continued

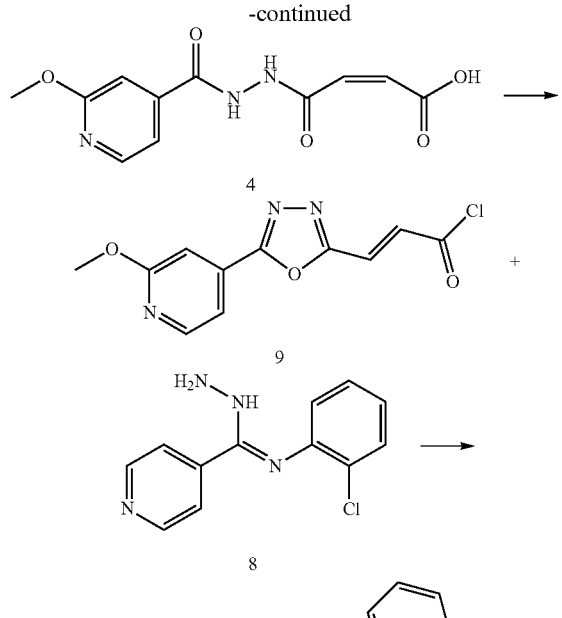

(a) Preparation of 2-methoxypyridine-4-carbohydrazide 3

To a solution of 2-methoxypyridine-4-carboxylic acid 1 (1.0 g, 6.5 mmol) in CH$_3$OH (30 mL) was added a few drops of SOCl$_2$ at ambient temperature. The mixture was stirred under reflux for 16 hours and concentrated to give methyl 2-methoxypyridine-4-carboxylate 2. To the solution of 2-methoxypyridine-4-carboxylate 2 in CH$_3$OH was added hydrazine monohydrate (2.0 mL, 37 mmol) at ambient temperature. The reaction mixture was stirred at ambient temperature for 16 hours and concentrated to give 2-methoxypyridine-4-carbohydrazide 3 as a white solid. Yield: 0.87 g, 80%.

$^1$H-NMR (300 MHZ, DMSO-d$_6$) δ (ppm): 10.0 (bs, 1H), 8.25 (dd, 1 H), 7.31 (dd, 1 H), 7.13 (s, 1H), 4.66 (bs, 2 H), 3.86 (s, 3 H).

(b) Preparation of (Z)-4-(2-methoxypyridine-4-carboamido)-4-oxobut-2-enoic acid 4

To a solution of 2-methoxypyridine-4-carbohydrazide 3 (0.80 g, 4.89 mmol) in THF (20 mL) was added malenic anhydride 7 (0.47 g, 4.79 mmol). The mixture was stirred at ambient temperature for 16 hours. The solid was filtered and dried under vacuum to afford pure compound (Z)-4-(2-methoxypyridine-4-carboamido)-4-oxobut-2-enoic acid 4 as a white solid.

Yield: 1.02 g, 80%.

$^1$H-NMR (300 MHz, DMSO-d$_6$) δ (ppm): 8.32 (d, 1 H), 7.38 (d, 1 H), 7.22 (s, 1 H), 6.38 (dd, 2H), 3.90 (s, 3 H), 3.40 (bs, 3 H).

(c) Preparation of N-(2-chlorophenyl)isonicotinamide 6

A mixture of isonicotinic acid 5 (1.0 g, 8.12 mmol) and SOCl$_2$ (2.4 mL) in DCM (10 mL) was stirred for 2 hours and concentrated. The residue was dissolved in DCM (20 mL). To the solution was added 2-chlorobenzenamine (1.7 g, 8.15 mmol) and then triethylamine (1.4 mL, 10 mmol). The reaction mixture was stirred overnight at ambient temperature and ethyl acetate (50 mL) was added followed by 1N HCl (10 mL). The organic phase was washed with water and brine, dried and concentrated under reduced pressure to yield a light yellow solid. Yield: 1.5 g, 80%. N-(2-chlorophenyl)isonicotinamide 6 was used for the next step without further purification.

$^1$H-NMR (300 Hz, CDCl$_3$) δ (ppm): 8.84 (dd, 2 H), 8.51 (d, 1 H), 8.48 (d, 1 H), 7.75 (dd, 2 H), 7.43 (dd, 1 H), 7.38-7.32 (m, 1 H), 7.16-7.10 (m, 1 H).

(d) Preparation of N-amino-N'-(2-chlorophenyl)pyridine-4-carboxamidine 8

A mixture of N-(2-chlorophenyl)isonicotinamide 6 (1.5 g, 6.45 mmol) and PCl$_5$ (1.6 g, 7.8 mmol) in benzene (40 mL) was stirred under reflux for 16 hours. The solvent was removed and further dried under high vacuum. The residue (Z)-2-chloro-N-(chloro(pyridin-4-yl)methylene)benzenamine 7 was cooled down by ice water bath and anhydrous THF added (20 mL) followed hydrazine monohydrate (1.2 mL). The reaction mixture was further stirred at ambient temperature for 3 hours. After the solvent was removed the residue was mixed with ether:hexane (1:1, 30 mL), the solid was filtered and further washed with ether:hexane mixture to yield a pure solid as N-amino-N'-(2-chlorophenyl)pyridine-4-carboxamidine 8. Yield: 1.1 g, 70%.

$^1$H-NMR (300 Hz, CDCl$_3$) δ 8.55 (dd, 2 H), 7.43 (dd, 2 H), 7.38 (d, 1 H), 7.07-7.01 (m, 1 H), 6.86-6.80 (dd, 1 H), 6.38 (dd, 1 H), 5.66 (bs, 3 H).

(e) Preparation of 4-(5-((E)-2-(5-(2,4-dichlorophenyl)-4-(2-chlorophenyl)-4H-1,2,4-triazol-3-yl)vinyl)-1,3,4-oxadiazol-2-yl)-2-methoxypyridine (Compound (3))

To a suspension of (Z)-4-(2-methoxypyridine-4-carboamido)-4-oxobut-2-enoic acid 4 (0.2 g, 0.75 mmol) in CH$_3$CN was added POCl$_3$ (0.37 g, 2.4 mmol). The mixture was stirred under reflux for 16 hours, cooled to ambient temperature and concentrated under reduced pressure. The residue was dissolved in CH$_3$CN and treated with a solution of N-amino-N'-(2-chlorophenyl)pyridine-4-carboxamidine 8 (0.38 g, 1.5 mmol) in CH$_3$CN and K$_2$CO$_3$ (0.38 g, 1.2 mmol). The mixture was stirred at ambient temperature for 1 hour, refluxed for 2 hours and filtered. The filtrate was concentrated. The residue was subjected to FCC (50-60% EtOAc/hexanes) to afford the title compound 4-(4-(2-chlorophenyl)-5-((E)-2-(5-(2-methoxypyridin-4-yl)-1,3,4-oxadiazol-2-yl)vinyl)-4H-1,2,4-triazol-3-yl)pyridine as a white solid. Yield: 0.11 g, 28%.

$^1$H-NMR (300 Hz, CDCl$_3$) δ (ppm): 8.58 (d, 2 H), 8.32 (d, 1 H), 7.74-7.64 (m, 3 H), 7.60-7.55 (m, 1 H), 7.50-7.43 (m, 2 H), 7.35-7.31 (m, 3 H), 7.09 (d, 1 H), 3.98 (s, 3 H).

MS (M+1) 457.4644.

HPLC (Waters 625 LC System): 96%.

EXAMPLE 4

Preparation of 5-chloro-2-(4-(2-chlorophenyl)-5-((E)-2-(5-(2-methoxypyridin-4-yl)-1,3,4-oxadiazol-2-yl)vinyl)-4H-1,2,4-triazol-3-yl)pyridine (Compound (4))

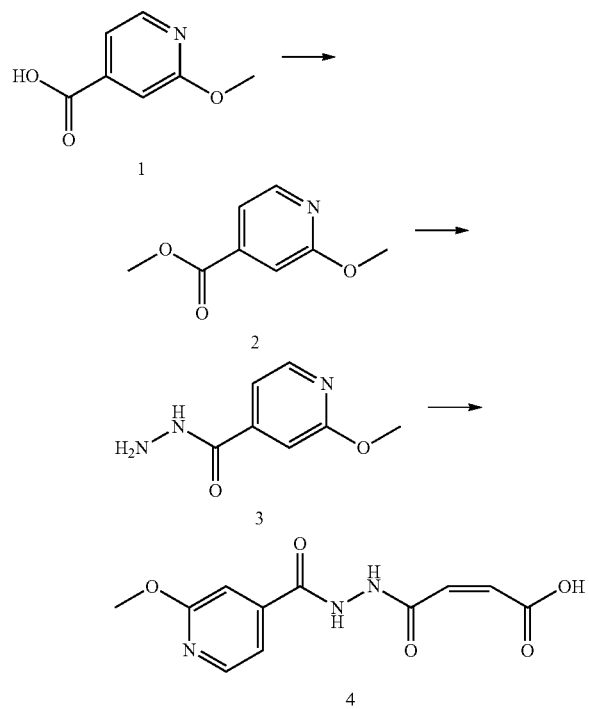

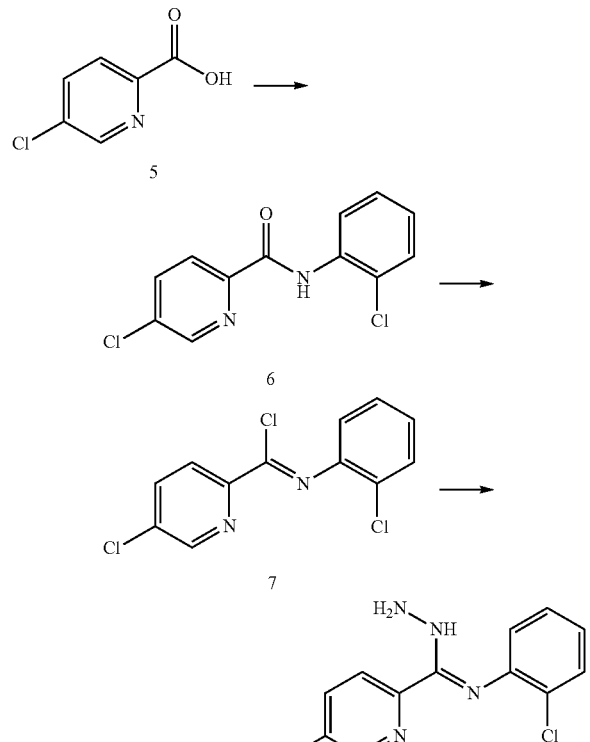

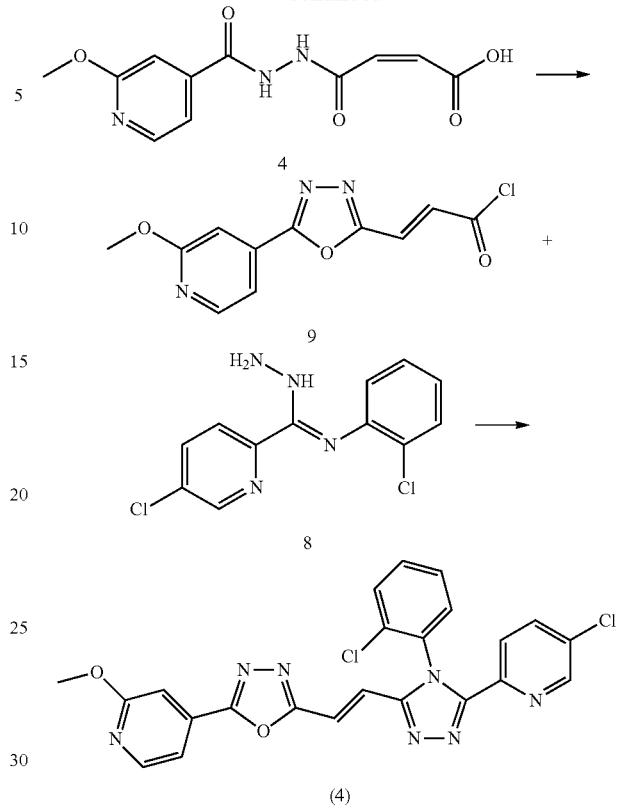

(a) Preparation of 2-methoxypyridine-4-carbohydrazide 3

To a solution of 2-methoxypyridine-4-carboxylic acid 1 (1.0 g, 6.5 mmol) in $CH_3OH$ (30 mL) was added a few drops of $SOCl_2$ at ambient temperature. The mixture was stirred under reflux for 16 hours and concentrated to give methyl 2-methoxypyridine-4-carboxylate 2. To the solution of 2-methoxypyridine-4-carboxylate 2 in $CH_3OH$ was added hydrazine monohydrate (2.0 mL, 37 mmol) at ambient temperature. The reaction mixture was stirred at ambient temperature for 16 hours and concentrated to give 2-methoxypyridine-4-carbohydrazide 3 as a white solid. Yield: 0.87 g, 80%.

$^1$H-NMR (300 MHZ, DMSO-$d_6$) δ (ppm): 10.0 (bs, 1 H), 8.25 (dd, 1 H), 7.31 (dd, 1 H), 7.13 (s, 1H), 4.66 (bs, 2 H), 3.86 (s, 3 H).

(b) Preparation of (Z)-4-(2-methoxypyridine-4-carboamido)-4-oxobut-2-enoic acid 4

To a solution of 2-methoxypyridine-4-carbohydrazide 3 (0.80 g, 4.89 mmol) in THF (20 mL) was added malenic anhydride 7 (0.47 g, 4.79 mmol). The mixture was stirred at ambient temperature for 16 hours. The solid was filtered and dried under vacuum to afford pure compound (Z)-4-(2-methoxypyridine-4-carboamido)-4-oxobut-2-enoic acid 4 as a white solid.

Yield: 1.02 g, 80%.

$^1$H-NMR (300 MHz, DMSO-$d_6$) δ (ppm): 8.32 (d, 1 H), 7.38 (d, 1 H), 7.22 (s, 1 H), 6.38 (dd, 2H), 3.90 (s, 3 H), 3.40 (bs, 3 H).

(b) Preparation of 5-chloro-N-(2-chlorophenyl)pyridine-2-carboxamide 6

A mixture of 5-chloropyridine-2-carboxylic acid 5 (1.0 g, 6.35 mmol) and SOCl$_2$ (2.4 mL) in DCM (10 mL) was stirred for 2 hours and concentrated. The residue was dissolved in DCM (20 mL). To the solution was added 2-chlorobenzenamine (1.0 g, 7.84 mmol) and then triethylamine (2.0 mL, 14.43 mmol). The reaction mixture was stirred overnight at ambient temperature and ethyl acetate (50 mL) was added followed by 1N HCl (10 mL). The organic phase was washed with water and brine, dried and concentrated under reduced pressure to yield a light yellow solid. Yield: 0.8 g, 47%. 5-chloro-N-(2-chlorophenyl)pyridine-2-carboxamide 6 was used for the next step without further purification.

$^1$H-NMR (300 Hz, CDCl$_3$) δ (ppm): 10.5 (bs, 1 H), 8.65-8.60 (m, 2 H), 8.28 (d, 1 H), 7.90 (dd, 1H), 7.44 (dd, 1 H), 7.38-7.30 (m, 1 H), 7.16-7.08 (m, 1 H).

(c) Preparation of N-amino-5-chloro-N'-(2-chlorophenyl)pyridine-2-carboxamidine 8

A mixture of 5-chloro-N-(2-chlorophenyl)pyridine-2-carboxamide 6 (0.8 g, 3.0 mmol) and PCl$_5$ (1 g, 4.8 mmol) in benzene (30 mL) was stirred under reflux for 16 hours. The solvent was removed and further dried under high vacuum. The residue (2Z)-5-chloro-N-(2-chlorophenyl)pyridine-2-carboximidoyl chloride 7 was cooled down by ice water bath and anhydrous THF added (20 mL) followed by hydrazine monohydrate (1.0 mL). The reaction mixture was further stirred at ambient temperature for 3 hours. After the solvent was removed the residue was mixed with ether:hexane (1:1, 30 mL), the solid was filtered and further washed with ether:hexane mixture to yield a pure solid as N-amino-5-chloro-N'-(2-chlorophenyl)pyridine-2-carboxamidine 8. Yield: 0.5 g, 60%.

$^1$H-NMR (300 Hz, CDCl$_3$) δ (ppm): 8.43 (dd, 1 H), 7.98 (d, 1 H), 7.65 (dd, 1 H), 7.41-7.32 (m, 2H), 7.19-7.13 (m, 1 H), 6.90-6.85 (m, 1 H), 6.50 (dd, 1 H), 5.36 (bs, 2 H).

(d) Preparation of 5-chloro-2-(4-(2-chlorophenyl)-5-((E)-2-(5-(2-methoxypyridin-4-yl)-1,3,4-oxadiazol-2-yl)vinyl)-4H-1,2,4-triazol-3-yl)pyridine (Compound (4))

To a suspension of (Z)-4-(2-methoxypyridine-4-carboamido)-4-oxobut-2-enoic acid 4 (0.2 g, 0.75 mmol) in CH$_3$CN was added POCl$_3$ (0.37 g, 2.4 mmol). The mixture was stirred under reflux for 16 hours, cooled to ambient temperature and concentrated under reduced pressure. The residue was dissolved in CH$_3$CN, treated with a solution of N-amino-5-chloro-N'-(2-chlorophenyl)pyridine-2-carboxamidine 8 (0.38 g, 1.2 mmol) in CH$_3$CN and K$_2$CO$_3$ (0.38 g, 1.2 mmol). The mixture was stirred at ambient temperature for 1 hour, refluxed for 2 hours, and filtered. The filtrate was concentrated. The residue was subjected to FCC (50-60% EtOAc/hexanes) to afford the title compound 5-chloro-2-(4-(2-chlorophenyl)-5-((E)-2-(5-(2-methoxypyridin-4-yl)-1,3,4-oxadiazol-2-yl)vinyl)-4H-1,2,4-triazol-3-yl)pyridine as a white solid. Yield: 0.11 g, 28%.

$^1$H-NMR (300 Hz, CDCl$_3$) δ (ppm): 8.33 (dd, 2 H), 8.18 (d, 1 H), 7.78 (dd, 1 H), 7.60-7.39 (m, 6H), 7.31 (dd, 1 H), 7.09 (d, 1 H), 3.98 (s, 3 H).

MS (M+1) 491.4821.

HPLC (Waters 625 LC System): 94%.

EXAMPLE 5

Preparation of 4-(5-((E)-2-(4-(2-chlorophenyl)-5-(3-methyl-1,2,4-oxadiazol-5-yl)-4H-1,2,4-triazol-3-yl)vinyl)-1,3,4-oxadiazol-2-yl)-2-methoxypyridine (Compound (5))

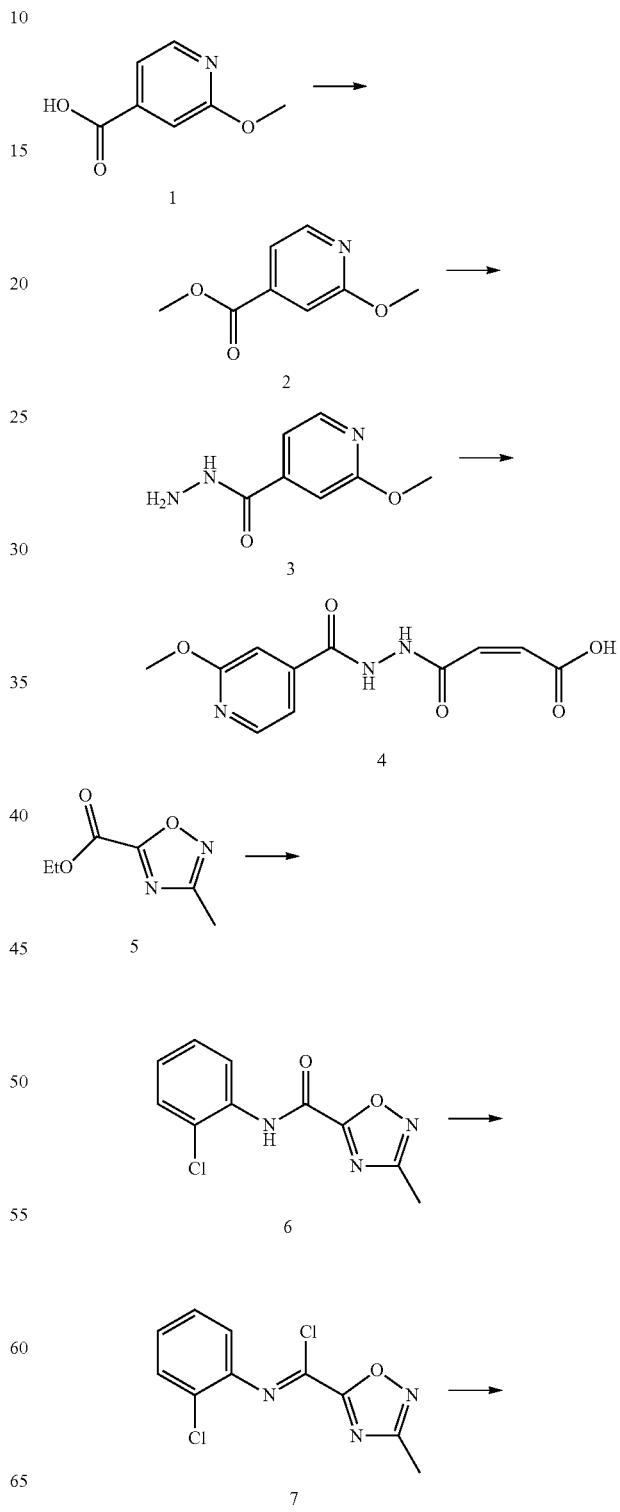

-continued

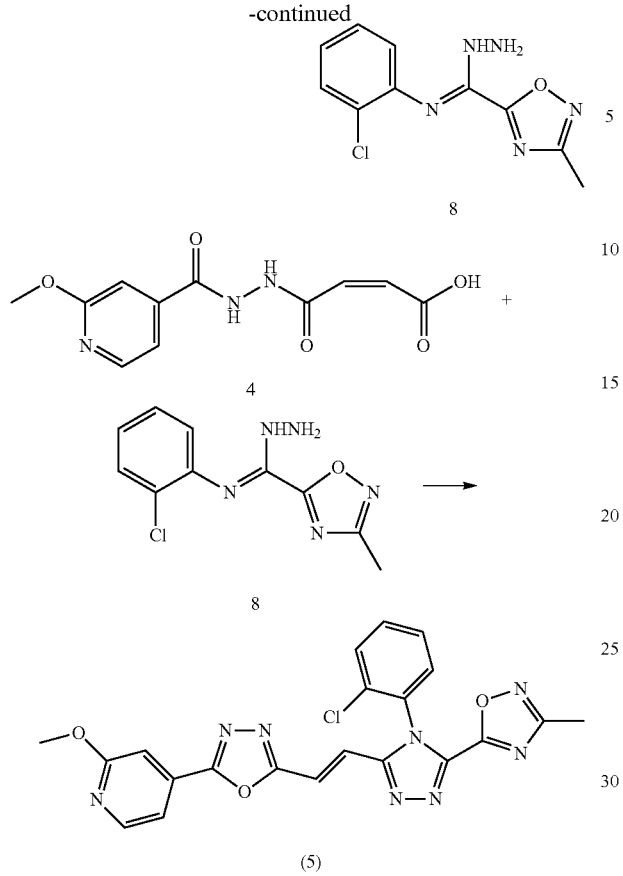

(a) Preparation of 2-methoxypyridine-4-carbohydrazide 3

To a solution of 2-methoxypyridine-4-carboxylic acid 1 (1.0 g, 6.5 mmol) in CH$_3$OH (30 mL) was added a few drops of SOCl$_2$ at ambient temperature. The mixture was stirred under reflux for 16 hours and concentrated to give methyl 2-methoxypyridine-4-carboxylate 2. To the solution of 2-methoxypyridine-4-carboxylate 2 in CH$_3$OH was added hydrazine monohydrate (2.0 mL, 37 mmol) at ambient temperature. The reaction mixture was stirred at ambient temperature for 16 hours and concentrated to give 2-methoxypyridine-4-carbohydrazide 3 as a white solid. Yield: 0.87 g, 80%.

$^1$H-NMR (300 MHZ, DMSO-d$_6$) δ (ppm): 10.0 (bs, 1H), 8.25 (dd, 1 H), 7.31 (dd, 1 H), 7.13 (s, 1H), 4.66 (bs, 2 H), 3.86 (s, 3 H).

(b) Preparation of (Z)-4-(2-methoxypyridine-4-carboamido)-4-oxobut-2-enoic acid 4

To a solution of 2-methoxypyridine-4-carbohydrazide 3 (0.80 g, 4.89 mmol) in THF (20 mL) was added malenic anhydride 7 (0.47 g, 4.79 mmol). The mixture was stirred at ambient temperature for 16 hours. The solid was filtered and dried under vacuum to afford pure compound (Z)-4-(2-methoxypyridine-4-carboamido)-4-oxobut-2-enoic acid 4 as a white solid. Yield: 1.02 g, 80%.

$^1$H-NMR (300 MHz, DMSO-d$_6$) δ (ppm): 8.32 (d, 1 H), 7.38 (d, 1 H), 7.22 (s, 1 H), 6.38 (dd, 2H), 3.90 (s, 3 H), 3.40 (bs, 3 H).

(c) Preparation of N-(2-chlorophenyl)-3-methyl-1,2,4-oxadiazole-5-carboxamide 6

To a mixture of ethyl 3-methyl-1,2,4-oxadiazole-5-carboxylate 5 (1.0 g, 6.4 mmol) and 2-chlorobenzenamine (1.23 g, 9.6 mmol) in toluene (20 mL) was added AlMe$_3$ (2.0 M 4.8 mL, 9.6 mmol) dropwise. The reaction mixture was stirred under reflux overnight, treated with 1N HCl (5 mL) and ethyl acetate (50 mL). The organic phase was dried and concentrated. The residue was purified by column chromatography eluting with hexane:ethyl acetate (1:3) to afford N-(2-chlorophenyl)-3-methyl-1,2,4-oxadiazole-5-carboxamide 6. Yield: 1.0 g, 66%.

$^1$H-NMR (300 Hz, CDCl$_3$) δ (ppm): 9.98 (s, 0.5 H), 9.38 (s, 0.5 H), 8.52-8.43 (m, 1 H), 7.48-7.38 (dd, 1 H), 7.40-7.32 (m, 1 H), 7.22-7.13 (m, 1 H), 2.56 (s, 3 H).

(d) Preparation of N-amino-N'-(2-chlorophenyl)-3-methyl-1,2,4-oxadiazole-5-carboxamidine 8

A mixture of N-(2-chlorophenyl)-3-methyl-1,2,4-oxadiazole-5-carboxamide 6 (1.0 g, 4.21 mmol) and PCl$_5$ (2 g, 9.6 mmol) in benzene (40 mL) was stirred under reflux for 16 hours. The solvent was removed and further dried under high vacuum. The residue (Z)-2-chloro-N-(chloro(3-methyl-1,2,4-oxadiazol-5-yl)methylene)benzenamine 7 was cooled down by ice water bath and anhydrous THF added (20 mL) followed hydrazine monohydrate (5.0 mL). The reaction mixture was further stirred at ambient temperature for 3 hours. After the solvent was removed the residue was mixed with ether:hexane (1:1, 30 mL), the solid was filtered and further washed with ether:hexane mixture to yield a pure solid as N-amino-N'-(2-chlorophenyl)-3-methyl-1,2,4-oxadiazole-5-carboxamidine 8. Yield: 0.5 g, 47%.

$^1$H-NMR (300 Hz, CDCl$_3$) δ (ppm): 7.40 (t, 1 H), 7.20 (t, 1 H), 6.92-6.82 (m, 1 H), 6.76 (s, 0.5H), 6.52-6.43 (m, 1 H), 6.28 (s, 0.5 H), 6.12 (s, 1 H), 5.25 (s, 1 H), 2.43 (s, 3 H).

(e) Preparation of 4-(5-((E)-2-(5-(2,4-dichlorophenyl)-4-(2-chlorophenyl)-4H-1,2,4-triazol-3-yl)vinyl)-1,3,4-oxadiazol-2-yl)-2-methoxypyridine (Compound (5))

To a suspension of (Z)-4-(2-methoxypyridine-4-carboamido)-4-oxobut-2-enoic acid 4 (0.2 g, 0.75 mmol) in CH$_3$CN was added POCl$_3$ (0.37 g, 2.4 mmol). The mixture was stirred under reflux for 16 hours, cooled to ambient temperature and concentrated under reduced pressure. The residue was dissolved in CH$_3$CN, treated with a solution of N-amino-N'-(2-chlorophenyl)-3-methyl-1,2,4-oxadiazole-5-carboxamidine 8 (0.5 g, 1.99 mmol) in CH$_3$CN and K$_2$CO$_3$ (0.38 g, 1.2 mmol). The mixture was stirred at ambient temperature for 1 hour, refluxed for 2 hours, and filtered. The filtrate was concentrated. The residue was subjected to FCC (50-60% EtOAc/hexanes) to afford the title compound 4-(5-((E)-2-(4-(2-chlorophenyl)-5-(3-methyl-1,2,4-oxadiazol-5-yl)-4H-1,2,4-triazol-3-yl)vinyl)-1,3,4-oxadiazol-2-yl)-2-methoxypyridine as a white solid. Yield: 0.1 g, 28%.

$^1$H-NMR (300 Hz, CDCl$_3$) δ (ppm): 8.32 (d, 1 H), 7.75-7.69 (m, 2 H), 7.60-7.55 (m, 1 H), 7.50-7.45 (m, 1 H), 7.30 (s, 1 H), 7.08 (d, 1 H), 3.98 (s, 3H), 2.35 (s, 3 H).

MS (M+1) 462.5578.

HPLC (Waters 625 LC System): 98%.

EXAMPLE 6

Tablets Containing 100 mg of Active Substance

Each tablet contains:

| | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |

The active substance, lactose and corn starch are mixed together and uniformly moistened with an aqueous solution of the polyvinylpyrrolidone. The moist composition is screened (2.0 mm mesh size) and dried at 50° C. The lubricant is added and the final mixture is compressed to form tablets. Final weight of each tablet is 220 mg.

EXAMPLE 7

Tablets Containing 150 mg of Active Substance

Each tablet contains:

| | |
|---|---|
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |

The active substance is mixed with lactose, corn starch and silica and moistened with an aqueous polyvinylpyrrolidone solution. The moist composition is passed through a screen with a mesh size of 1.5 mm. The resulting granules are dried at 45° C., then mixed with the magnesium stearate. Tablets are pressed from the mixture. Each tablet weighs 300 mg.

EXAMPLE 8

Ampoules Containing 10 mg Active Substance

Each ampoule contains:

| | |
|---|---|
| active substance | 10.0 mg |
| 0.01N hydrochloric acid | q.s. |
| double-distilled water | ad 2.0 ml |

The active substance is dissolved in the necessary amount of 0.01 N HCl, made isotonic with common salt, sterile filtered and transferred into 2 ml ampoules.

EXAMPLE 9

Ampoules Containing 50 mg of Active Substance

Each ampoule contains:

| | |
|---|---|
| active substance | 50.0 mg |
| 0.01N hydrochloric acid | q.s. |
| double-distilled water | ad 10.0 ml |

The active substance is dissolved in the necessary amount of 0.01 N HCl, made isotonic with common salt, sterile filtered and transferred into 10 ml ampoules.

EXAMPLE 10

Preparation of 2-(4-(2-chlorophenyl)-5-((E)-2-(5-(2-methoxypyridin-4-yl)-1,3,4-oxadiazol-2-yl)vinyl)-4H-1,2,4-triazol-3-yl)-5-ethoxypyridine (Compound (13))

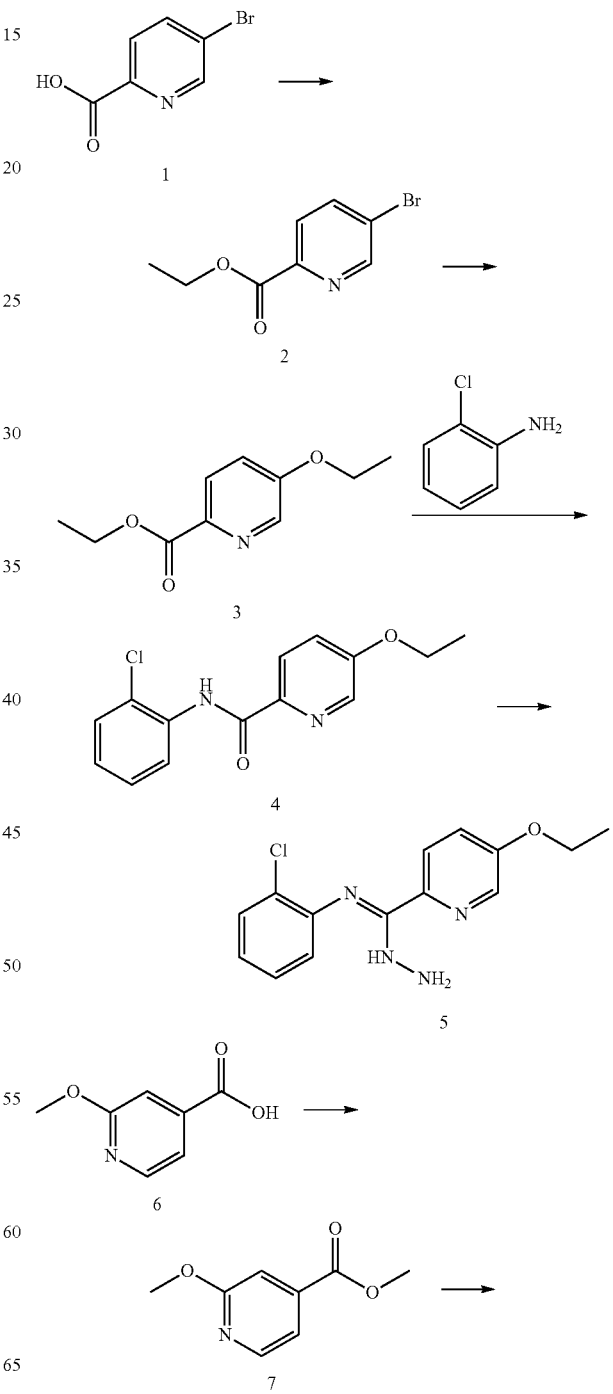

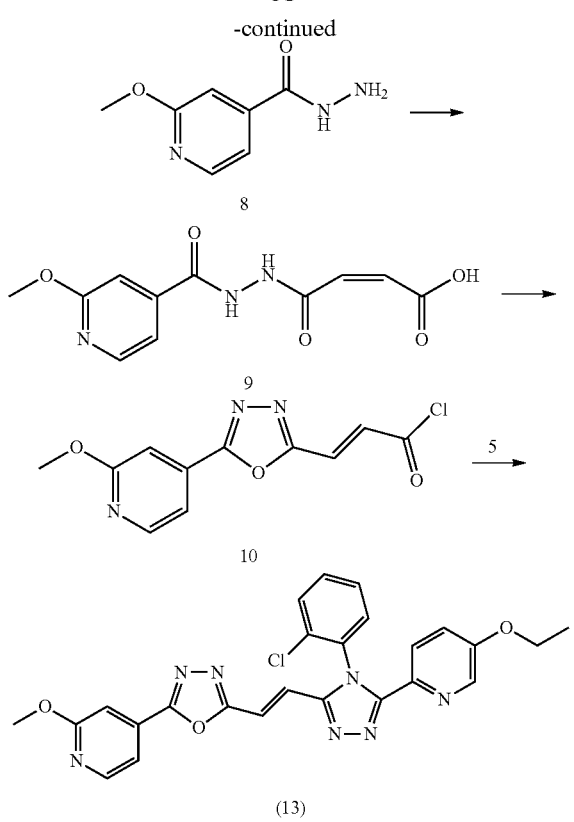

(a) Preparation of ethyl 5-bromopyridine-2-carboxylate 2

To a suspension of 5-bromopyridine-2-carboxylic acid 1 (2.02 g, 10 mmol) in 50 mL of EtOH was added thionyl chloride (5 mL). The mixture was stirred at ambient temperature for 18 h. After removal of all solvent, the residue was purified by column (2:1 of hexane/ethyl acetate) to give 2.3 g of ethyl 5-bromopyridine-2-carboxylate 2 as an oil. Yield: 2.3 g, quantitative yield.
$^1$HNMR (CDCl$_3$) δ (ppm): 8.80 (d, 1 H), 8.00 (m, 2 H), 4.50 (m, 2 H), 1.44 (t, 3 H).

(b) Preparation of ethyl 5-ethoxypyridine-2-carboxylate 3

To a solution of ethyl 5-bromopyridine-2-carboxylate 2 (1.5 g, 6.5 mmol) in 20 mL of EtOH was added a solution of sodium (0.18 g, 7.8 mmol) in 20 mL of EtOH. The mixture was stirred at reflux for 3 h. After removal of all solvent, the residue was purified by column (2:1 of hexane/ethyl acetate) to give ethyl 5-ethoxypyridine-2-carboxylate 3 as an oil. Yield: 0.26 g, 20%. $^1$HNMR (CDCl$_3$) δ (ppm): 8.38 (d, 1 H), 8.10 (d, 1 H), 8.23 (d, 1 H), 7.22 (dd, 1 H), 4.45 (m, 2 H), 4.25 (m, 1 H), 1.40 (m, 6 H).

(c) Preparation of N-(2-chlorophenyl)-5-ethoxypyridine-2-carboxamide 4

To a solution of o-chloroaniline (0.68 g, 5.3 mmol) in 20 mL of PhMe was added 3 mL of AlMe$_3$. The mixture was stirred at ambient temperature for 0.5 h and added into a solution of ethyl 5-ethoxypyridine-2-carboxylate 3 (0.26 g, 1.33 mmol) in 10 mL of PhMe. The mixture was stirred at ambient temperature for 15 h and quenched with 20 mL of 1N HCl. The mixture was extracted with ethyl acetate. The organic layer was separated and concentrated. The residue was purified by column (2:1 of hexane/ethyl acetate) to give N-(2-chlorophenyl)-5-ethoxypyridine-2-carboxamide 4 as a solid. Yield: 310 mg, 96%.
$^1$HNMR (CDCl$_3$) δ (ppm): 10.55 (s, 1 H), 8.65 (d, 1 H), 8.30 (d, 1 H), 8.23 (d, 1 H), 7.42 (d, 1 H), 7.30 (m, 2 H), 7.05 (dd, 1 H), 4.20 (m, 2 H), 1.50 (t, 3 H).

(d) Preparation of N-amino-N'-(2-chlorophenyl)-5-ethoxy-pyridine-2-carboxamidine 5

To a solution of N-(2-chlorophenyl)-5-ethoxypyridine-2-carboxamide 4 (0.15 g, 0.64 mmol) in 20 mL of benzene was added 650 mg of PCl$_5$. The mixture was stirred at reflux for 2 h. After removal of the solvent, the residue was dissolved in 30 mL of THF and added to 3 mL of H$_2$NNH$_2$.H$_2$O. The mixture was heated at reflux for 0.5 h. After removal of solvent, the residue was purified by column (5-10% of methanol in dichloromethane) to give N-amino-N'-(2-chlorophenyl)-5-ethoxy-pyridine-2-carboxamidine 5 as a solid. Yield: 140 mg, 95%.
$^1$HNMR (CDCl$_3$) δ (ppm): 8.20 (d, 1 H), 7.95 (d, 1 H), 7.50 (s, 1 H), 7.35 (d, 1 H), 7.20 (m, 2 H), 6.85 (dd, 1 H), 6.55 (d, 1 H), 5.20 (s, 2 H), 4.10 (m, 2 H), 1.40 (t, 3 H).

(e) Preparation of 2-methoxypyridine-4-carbohydrazide 8

To a solution of 2-methoxypyridine-4-carboxylic acid 6 (2.0 g, 13 mmol) in 30 mL of MeOH was added 3 mL of thionyl chloride. The mixture was stirred at reflux for 2 h. After removal of the solvent, the residue was dissolved in 30 mL of THF and added to 3 mL of H$_2$NNH$_2$.H$_2$O. The mixture was heated at reflux for 0.5 h. After removal of solvent, the residue was purified by column (5-10% of methanol in dichloromethane) to give 2-methoxypyridine-4-carbohydrazide 8 as a solid. Yield: 1.76 g, 81%.
$^1$HNMR (DMSO-d$_6$) δ (ppm): 9.98 (s, 1 H), 8.25 (d, 1 H), 7.30 (d, 1 H), 7.13 (s, 1 H), 4.57 (s, 2 H), 3.86 (s, 3 H).

(f) Preparation of (Z)-4-(2-methoxypyridine-4-carboamido)-4-oxobut-2-enoic acid 9

To a solution of 2-methoxypyridine-4-carbohydrazide 8 (167 mg, 1.0 mmol) in 10 mL of THF was added maleic anhydride (110 mg, 1.1 mmol). The mixture was stirred at ambient temperature for 2 h. After removal of the solvent, the residue was diluted with 10 mL of dichloromethane. The solid was collected by filtration to give (Z)-4-(2-methoxypyridine-4-carboamido)-4-oxobut-2-enoic acid 9 as a solid. Yield: 190 mg, 71%.
$^1$HNMR (DMSO-d$_6$) δ (ppm): 10.80 (s, 2 H), 8.32 (d, 1 H), 7.36 (d, 1 H), 7.20 (s, 1 H), 6.41 (d, 1 H), 6.29 (d, 1 H), 3.90 (s, 3 H).

(g) Preparation of 2-(4-(2-chlorophenyl)-5-((E)-2-(5-(2-methoxypyridin-4-yl)-1,3,4-oxadiazol-2-yl)vinyl)-4H-1,2,4-triazol-3-yl)-5-ethoxypyridine (Compound (13))

To a suspension of (Z)-4-(2-methoxypyridine-4-carboamido)-4-oxobut-2-enoic acid 9 (0.30 g, mmol) in 20 mL of PhMe was added 0.5 mL of POCl$_3$. The mixture was stirred at reflux for 2 h. After removal of solvent, the residue was dissolved in 20 mL of dichloromethane and added to 240 mg (0.68 mmol) of N-amino-N'-(2-chlorophenyl)-5-ethoxy-pyridine-2-carboxamidine 5. The mixture was stirred at ambient temperature for 2 h. After removal of solvent, the residue was suspended in 20 mL of PhMe and refluxed for 3 h. After removal of solvent, the residue was purified by column (0-5% of methanol in dichloromethane) to give 2-(4-(2-chlorophenyl)-5-((E)-2-(5-(2-methoxypyridin-4-yl)-1,3,4-oxadiazol-2-yl)vinyl)-4H-1,2,4-triazol-3-yl)-5-ethoxypyridine as a solid. Yield: 20 mg, 3.5%.

¹HNMR (CDCl₃) δ (ppm): 8.33 (d, 1 H), 8.24 (d, 1 H), 7.89 (d, 1 H), 7.60-7.20 (m, 8 H), 7.14 (d, 1 H), 4.10 (m, 5 H), 1.40 (t, 3 H).

MS: 502.3 (MH⁺).

HPLC: 99%

EXAMPLE 11

Preparation of 4-(4-(2-chlorophenyl)-5-((E)-2-(5-(2-methoxypyridin-4-yl)-1,3,4-oxadiazol-2-yl)vinyl)-4H-1,2,4-triazol-3-yl)pyrimidine (Compound (11))

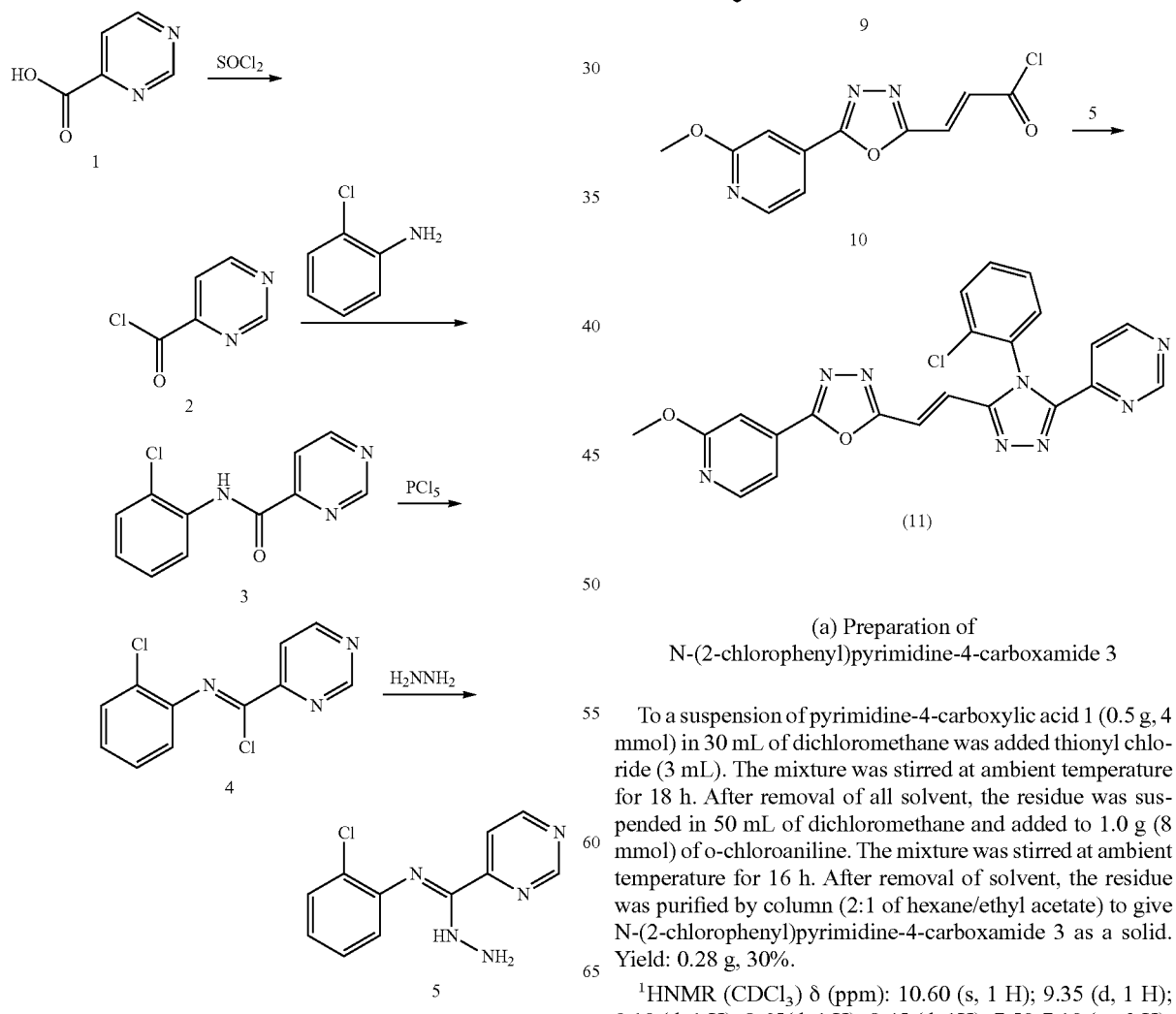

(a) Preparation of N-(2-chlorophenyl)pyrimidine-4-carboxamide 3

To a suspension of pyrimidine-4-carboxylic acid 1 (0.5 g, 4 mmol) in 30 mL of dichloromethane was added thionyl chloride (3 mL). The mixture was stirred at ambient temperature for 18 h. After removal of all solvent, the residue was suspended in 50 mL of dichloromethane and added to 1.0 g (8 mmol) of o-chloroaniline. The mixture was stirred at ambient temperature for 16 h. After removal of solvent, the residue was purified by column (2:1 of hexane/ethyl acetate) to give N-(2-chlorophenyl)pyrimidine-4-carboxamide 3 as a solid. Yield: 0.28 g, 30%.

¹HNMR (CDCl₃) δ (ppm): 10.60 (s, 1 H); 9.35 (d, 1 H); 9.10 (d, 1 H); 8.65(d, 1 H); 8.45 (d, 1H); 7.50-7.10 (m, 3 H).

(b) Preparation of N-amino-N'-(2-chlorophenyl)pyrimidine-4-carboxamidine 5

To a suspension of N-(2-chlorophenyl)pyrimidine-4-carboxamide 3 (0.2 g, 0.86 mmol) in 20 mL of PhMe was added 0.65 g of $PCl_5$. The mixture was stirred at reflux for 3 h. To this solution was added 3 mL of $NH_2NH_2 \cdot H_2O$. The mixture was stirred at ambient temperature for 2 h. After removal of all solvent, the residue was purified by column (2:1 of hexane/ethyl acetate) to give N-amino-N'-(2-chlorophenyl)pyrimidine-4-carboxamidine 5 as a solid. Yield: 0.15 g, 70%.

$^1$HNMR (DMSO-$d_6$) δ (ppm): 9.15 (s, 1 H); 8.70 (d, 1 H); 7.98 (d, 1 H); 7.35 (m, 1 H); 7.15 (m, 1 H); 6.80 (m, 1 H); 6.45 (d, 1 H); 5.60 (s, 2 H).

(c) Preparation of 2-methoxypyridine-4-carbohydrazide 8

To a solution of 2-methoxypyridine-4-carboxylic acid 6 (2.0 g, 13 mmol) in 30 mL of MeOH was added 3 mL of thionyl chloride. The mixture was stirred at reflux for 2 h. After removal of the solvent, the residue was dissolved in 30 mL of THF and added to 3 mL of $H_2NNH_2 \cdot H_2O$. The mixture was heated at reflux for 0.5 h. After removal of solvent, the residue was purified by column (5-10% of methanol in dichloromethane) to give 2-methoxypyridine-4-carbohydrazide 8 as a solid. Yield: 1.76 g, 81%.

$^1$HNMR (DMSO-$d_6$) δ (ppm): 9.98 (s, 1 H); 8.25 (d, 1 H); 7.30 (d, 1 H); 7.13 (s, 1 H); 4.57 (s, 2H); 3.86 (s, 3 H).

(d) Preparation of (Z)-4-(2-methoxypyridine-4-carboamido)-4-oxobut-2-enoic acid 9

To a solution of 2-methoxypyridine-4-carbohydrazide 8 (167 mg, 1.0 mmol) in 10 mL of THF was added maleic anhydride (110 mg, 1.1 mmol 1). The mixture was stirred at ambient temperature for 2 h. After removal of the solvent, the residue was diluted with 10 mL of dichloromethane. The solid was collected by filtration to give (Z)-4-(2-methoxypyridine-4-carboamido)-4-oxobut-2-enoic acid 9 as a solid. Yield: 190 mg, 71%.

$^1$HNMR (DMSO-$d_6$) δ (ppm): 10.45 (s, 2 H); 8.32 (d, 1 H); 7.36 (d, 1 H); 7.20 (s, 1 H); 6.41 (d, 1 H); 6.29 (d, 1 H); 3.90 (s, 3 H).

(e) Preparation of 4-(4-(2-chlorophenyl)-5-((E)-2-(5-(2-methoxypyridin-4-yl)-1,3,4-oxadiazol-2-yl)vinyl)-4H-1,2,4-triazol-3-yl)pyrimidine (Compound (11))

To a suspension of (Z)-4-(2-methoxypyridine-4-carboamido)-4-oxobut-2-enoic acid 9 (200 mg, 0.75 mmol) in 20 mL of PhMe was added 0.5 mL of $POCl_3$. The mixture was stirred at reflux for 2 h. After removal of solvent, the residue was dissolved in 20 mL of dichloromethane and added to 150 mg (0.6 mmol) of N-amino-N'-(2-chlorophenyl)pyrimidine-4-carboxamidine 5. The mixture was stirred at ambient temperature for 2 h. After removal of solvent, the residue was suspended in 20 mL of PhMe and refluxed for 3 h. After removal of solvent, the residue was purified by column (0-5% of methanol in dichloromethane) to give 4-(4-(2-chlorophenyl)-5-((E)-2-(5-(2-methoxypyridin-4-yl)-1,3,4-oxadiazol-2-yl)vinyl)-4H-1,2,4-triazol-3-yl)pyrimidine as a solid. Yield: 30 mg.

$^1$HNMR (CDCl$_3$) δ (ppm): 8.83 (m, 2H); 8.32 (m, 2 H); 7.70-7.30 (m, 7 H); 7.10 (d, 1 H); 4.00 (s, 3 H).

MS: 459.3 (MH$^+$).

HPLC: 99%

EXAMPLE 12

Preparation of 2-(4-(2-chlorophenyl)-5-((E)-2-(5-(2-methoxypyridin-4-yl)-1,3,4-oxadiazol-2-yl)vinyl)-4H-1,2,4-triazol-3-yl)-5-(methylsulfonyl)pyridine (Compound (12))

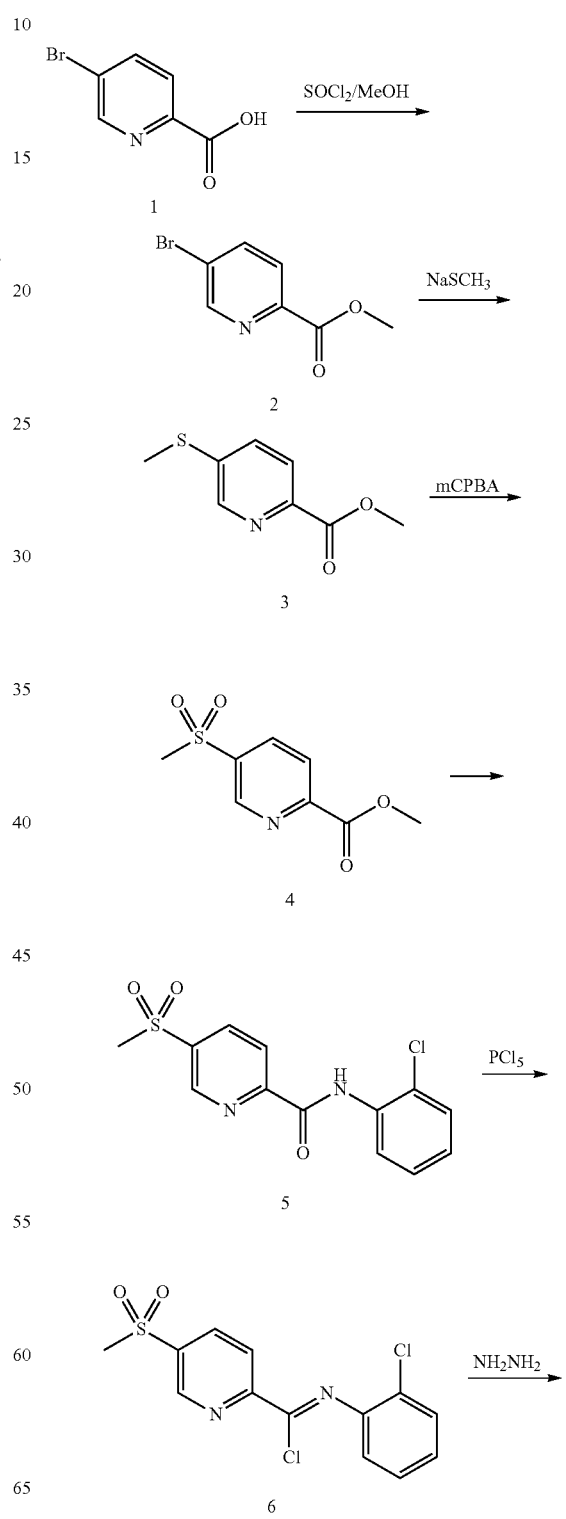

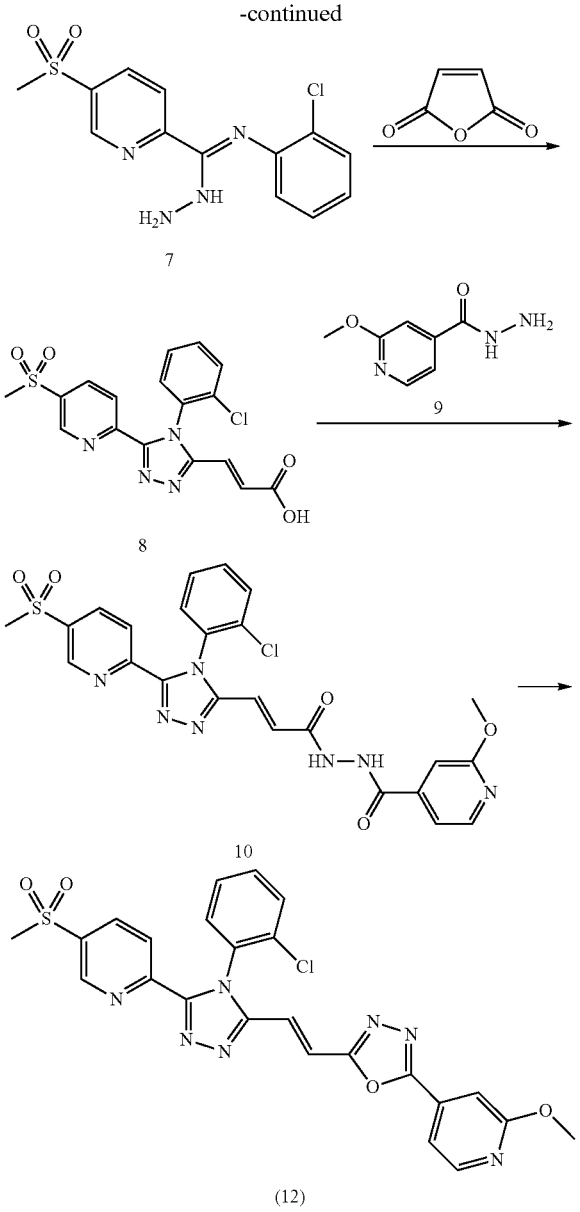

heated to reflux overnight. The solvent was removed and the residue was purified by column chromatography (eluting with hexane and ethyl acetate 1:1). Methyl 5-(methylthio)picolinate 3 as a white solid was isolated. Yield: 3.0 g, 57.1%.

$^1$H-NMR (300 Hz, CDCl$_3$) δ (ppm): 8.58 (d, 1 H), 8.02 (d, 1 H), 7.60 (dd, 1 H), 3.99 (s, 3 H), 2.58 (s, 3 H).

(c) Preparation of methyl 5-(methylsulfonyl)picolinate 4

To a 100 mL round bottle flask with methyl 5-(methylthio)picolinate 3 (1.50 g, 8.2 mmol) in 30 mL of DCM was added mCPBA (5.51 g, 77%, 25.0 mmol). The reaction was kept at ambient temperature overnight. After solvent was removed, the residue was purified by column chromatography (eluting with hexane and ethyl acetate 1:1) to give methyl 5-(methylsulfonyl)picolinate 4 as a white solid. Yield: 1.35 g, 76.5%.

$^1$H-NMR (300 Hz, CDCl$_3$) δ (ppm): 9.22 (d, 1H), 8.40 (dd, 1H), 8.36 (d, 1H), 4.02 (s, 3H), 3.10 (s, 3H).

(d) Preparation of N-(2-chlorophenyl)-5-(methylsulfonyl)picolinamide 5

2-Chloroaniline (1.20 g, 0.0093 mol) in toluene (20 mL) was added to trimethylaluminum (2.0 M 4.6 mL) then methyl 5-(methylsulfonyl)picolinate 4 (1.0 g, 4.65 mol) was added and the mixture was heated to 80-90° C. for 2 h. The reaction mixture was cooled down and 1N HCl solution (10 mL) was added to be acidic. Dichloromethane (100 mL) was then added and the organic phase was further washed with water (100 mL) and dried over sodium sulfate. The solvent was removed and the residue was mixed with ether (50 mL) and stirred for 0.5 h. The solid was filtered and dried to give N-(2-chlorophenyl)-5-(methylsulfonyl)picolinamide 5 as a light yellow solid. Yield: 1.26 g, 87.2%.

$^1$H-NMR (300 Hz, CDCl$_3$) δ (ppm): 10.6 (s, 1H), 9.21 (m, 1H), 8.62 (dd, 1H), 8.51 (dd, 1H), 8.46 (dd, 1H), 7.45 (dd, 1H), 7.34 (td, 1H), 7.12 (td, 1H), 3.20 (s, 3H).

(e) Preparation of N'-(2-chlorophenyl)-5-(methylsulfonyl)picolinimidohydrazide 7

N-(2-chlorophenyl)-5-(methylsulfonyl)picolinamide 5 (1.26 g, 0.0040 mol) in anhydrous benzene (20 mL) was added to PCl$_5$ (1.26 g, 6.0 mmol) and the mixture was heated to reflux overnight. The solvent was removed and the residue was further dried under high vacuum. Crude N-(2-chlorophenyl)-5-(methylsulfonyl)picolinimidoyl chloride 6 was obtained as a yellow solid (1.60 g). The N-(2-chlorophenyl)-5-(methylsulfonyl)picolinimidoyl chloride 6 was dissolved into THF anhydrous (30 mL) and the reaction was cooled down to 0° C. and hydrazine monohydrate (9.0 mL) was added. The reaction was kept at 0° C. for 10 min and warmed to ambient temperature in 0.5 h. The solvent was removed and the residue was purified by column chromatography (eluting with hexane and ethyl acetate 1:1) to give N'-(2-chlorophenyl)-5-(methylsulfonyl) picolinimidohydrazide 7 as a yellow solid. Yield: 1.22 g, 92.0%.

$^1$H-NMR (300 Hz, CDCl$_3$) δ (ppm): 9.02 (dd, 1H), 8.25 (dd, 1H), 8.17 (dd, 1H) 7.44 (s, 1H), 7.37 (dd, 1H), 7.16 (td, 1H), 6.89 (td, 1H), 6.45 (dd, 1H), 5.62 (s, 2H), 3.06 (s, 3H).

(f) Preparation of 3-(4-(2-chlorophenyl)-5-(5-(methylsulfonyl)pyridin-2-yl)-4H-1,2,4-triazol-3-yl)acrylic acid 8

To a 100 mL flask with N'-(2-chlorophenyl)-5-(methylsulfonyl) picolinimidohydrazide 7 (0.63 g, 1.94 mol) in anhy-

---

(a) Preparation of methyl 5-bromopicolinate 2

To a 100 mL round bottle flask with 5-bromopicolinic acid (7.0 g, 35 mmol) in methanol (80 mL) was added dropwise thionyl chloride (3.0 mL) at ambient temperature. After addition the reaction mixture was heated to reflux for 3 h. Methanol was removed and ethyl acetate (100 mL) was added to the residue and was adjusted pH to 7.0 by addition of sodium bicarbonate solution. The organic phase was separated and dried over sodium sulfate. The organic solvent was removed and methyl 5-bromopicolinate 2 was obtained as white solid which was used for the next step of the reaction without further purification. Yield: 6.57 g, 86.9%

(b) Preparation of methyl 5-(methylthio)picolinate 3

A solution of methyl 5-bromopicolinate 2 (6.20 g, 28.7 mmol) in anhydrous THF (150 mL) was added to sodium methylhionide (2.51 g, 35.9 mmol) and the reaction was drous toluene (20 mL) was added maleic anhydride (0.20 g, 2.04 mol) and the reaction was kept at ambient temperature for 1 h and then heated to reflux for 3 h. After solvent was removed, the residue was dried under high vacuum to give 3-(4-(2-chlorophenyl)-5-(5-(methylsulfonyl)pyridin-2-yl)-4H-1,2,4-triazol-3-yl)acrylic acid 8 as a yellow solid. Yield: 0.75 g, 95.6%.

(g) Preparation of 2-methoxypyridine-4-carbohydrazide 9

To a solution of 2-methoxypyridine-4-carboxylic acid (2.0 g, 13 mmol) in 30 mL of MeOH was added 3 mL of thionyl chloride. The mixture was stirred at reflux for 2 h. After removal of the solvent, the residue was dissolved in 30 mL of THF and added to 3 mL of $H_2NNH_2.H_2O$. The mixture was heated at reflux for 0.5 h. After removal of solvent, the residue was purified by column (5-10% of methanol in dichloromethane) to give 2-methoxypyridine-4-carbohydrazide 9 as a solid. Yield: 1.76 g, 81%.

$^1$HNMR (DMSO-$d_6$) δ (ppm): 9.98 (s, 1 H); 8.25 (d, 1 H); 7.30 (d, 1 H); 7.13 (s, 1 H); 4.57 (s, 2H); 3.86 (s, 3 H).

(h) Preparation of 2-(4-(2-chlorophenyl)-5-((E)-2-(5-(2-methoxypyridin-4-yl)-1,3,4-oxadiazol-2-yl)vinyl)-4H-1,2,4-triazol-3-yl)-5-(methylsulfonyl)pyridine (Compound (12))

To a 100 mL flask with 3-(4-(2-chlorophenyl)-5-(5-(methylsulfonyl)pyridin-2-yl)-4H-1,2,4-triazol-3-yl)acrylic acid 8 (0.21 g, 0.52 mmol) in dichloromethane (20 mL) was added oxalyl chloride (0.20 g, 1.55 mmol) and a drop of DMF. The reaction was kept at ambient temperature for 3 h. The solvent was removed and the residue was further dried under high vacuum and cooled to −20° C. Dichloromethane (10 mL) was added, followed by 2-methoxyisonicotinohydrazide 9 (0.10 g, 0.6 mmol) and triethylamine (0.5 mL). The reaction mixture was kept at this temperature for 0.5 h and then warmed to ambient temperature for 1 h. The solvent was removed and the crude N'-[(E)-3-[4-(2-chlorophenyl)-5-(5-methylsulfonyl-2-pyridyl)-1,2,4-triazol-3-yl]prop-2-enoyl]-2-methoxy-pyridine-4-carbohydrazide 10 was used for the next step.

N'-[(E)-3-[4-(2-chlorophenyl)-5-(5-methylsulfonyl-2-pyridyl)-1,2,4-triazol-3-yl]prop-2-enoyl]-2-methoxy-pyridine-4-carbohydrazide 10 was dissolved into dichloromethane (10 mL), and triphenyl phosphine (0.27 g, 1.0 mmol), carbon tetrabromide (0.34 g, 1.04 mmol) and triethylamine (0.18 mL, 1.30 mmol) were added. The reaction mixture was kept at ambient temperature for 2 h. The final compound was purified by column chromatography (eluting with hexane and ethyl acetate 1:3) to give 2-(4-(2-chlorophenyl)-5-((E)-2-(5-(2-methoxypyridin-4-yl)-1,3,4-oxadiazol-2-yl)vinyl)-4H-1,2,4-triazol-3-yl)-5-(methylsulfonyl)pyridine as a yellow solid.

Yield: 0.031 g, 11%.

$^1$H-NMR (300 Hz, CDCl$_3$) δ (ppm): 8.75 (d, 1 H), 8.62 (d, 1 H), 8.35-8.29 (m, 2 H), 7.70-7.60 (m, 2 H), 7.55-7.48 (m, 2 H), 7.45-7.39 (m, 1 H), 7.33-7.32 (m, 1 H), 7.12 (d, 1 H), 4.01 (s, 3 H), 3.09 (s, 3 H).

MS: 536.3 (MH$^+$).

HPLC: 96%

EXAMPLE 13

Preparation of (E)-4-(5-(2-(4-(2-chlorophenyl)-5-(5-(methylsulfonyl)pyridin-2-yl)-4H-1,2,4-triazol-3-yl)vinyl)-1,3,4-oxadiazol-2-yl)benzonitrile (Compound (10))

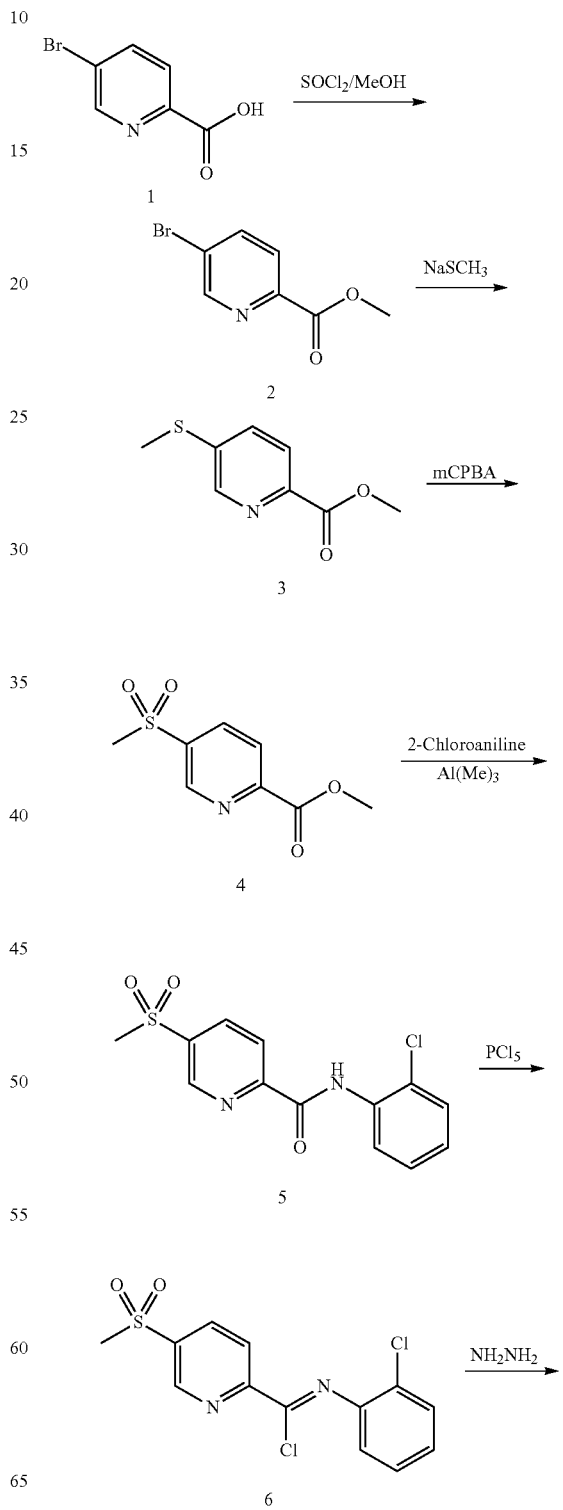

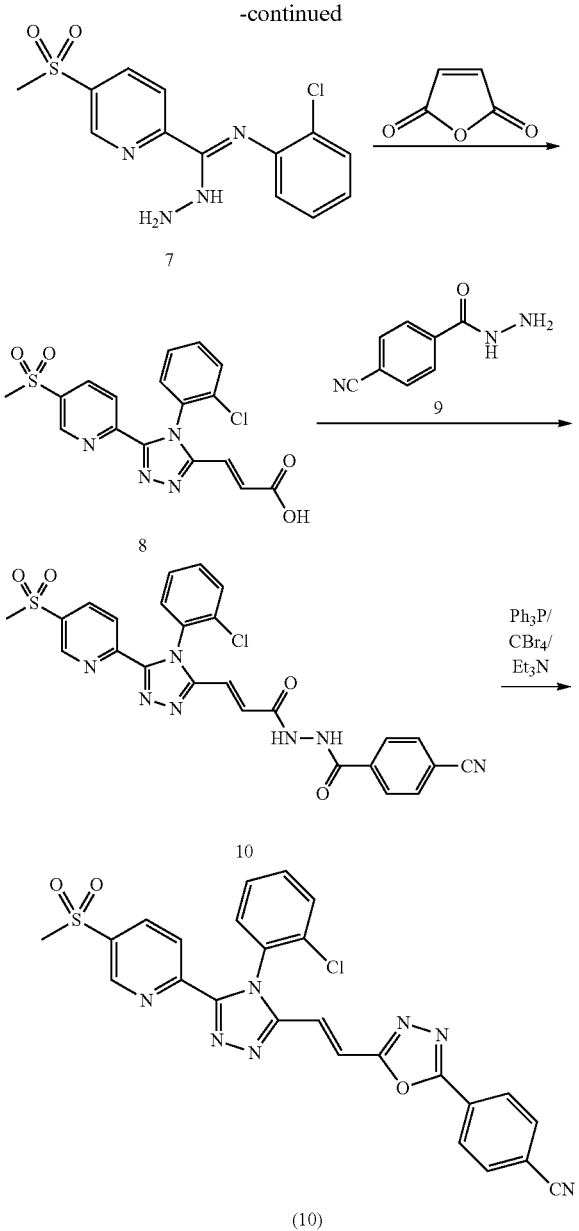

(a) Preparation of methyl 5-bromopicolinate 2

To a 100 mL round bottle flask with 5-bromopicolinic acid (7.0 g, 35 mmol) in methanol (80 mL) was added dropwise thionyl chloride (3.0 mL) at ambient temperature. After addition the reaction mixture was heated to reflux for 3 h. Methanol was removed and ethyl acetate (100 mL) was added to the residue and was adjusted pH to 7.0 by addition of sodium bicarbonate solution. The organic phase was separated and dried over sodium sulfate. The organic solvent was removed and methyl 5-bromopicolinate 2 was obtained as a white solid which was used for the next step reaction without further purification. Yield: 6.57 g, 86.9%.

(b) Preparation of methyl 5-(methylthio)picolinate 3

A solution of methyl 5-bromopicolinate 2 (6.20 g, 28.7 mmol) in anhydrous THF (150 mL) was added to sodium methylhionide (2.51 g, 35.9 mmol) and the reaction was heated to reflux overnight. The solvent was removed and the residue was purified by column chromatography (eluting with hexane and ethyl acetate 1:1). Methyl 5-(methylthio) picolinate 3 as a white solid was isolated. Yield: 3.0 g, 57.1%.

$^1$H-NMR (300 Hz, CDCl$_3$) δ (ppm): 8.58 (d, 1H), 8.02 (d, 1H), 7.60 (dd, 1H), 3.99 (s, 3H), 2.58 (s, 3H).

(c) Preparation of methyl 5-(methylsulfonyl)picolinate 4

To a 100 mL round bottle flask with methyl 5-(methylthio) picolinate 3 (1.50 g, 8.2 mmol) in 30 mL of DCM was added mCPBA (5.51 g, 77%, 25.0 mmol). The reaction was kept at ambient temperature overnight. After the solvent was removed, the residue was purified by column chromatography (eluting with hexane and ethyl acetate 1:1) to give methyl 5-(methylsulfonyl)picolinate 4 as a white solid. Yield: 1.35 g, 76.5%.

$^1$H-NMR (300 Hz, CDCl$_3$) δ ppm 9.22 (d, 1H), 8.40 (dd, 1H), 8.36 (d, 1H), 4.02 (s, 3H), 3.10 (s, 3H).

(d) Preparation of N-(2-chlorophenyl)-5-(methylsulfonyl)picolinamide 5

To 2-Chloroaniline (1.20 g, 0.0093 mol) in toluene (20 mL) was added trimethylaluminum (2.0 M 4.6 mL) then methyl 5-(methylsulfonyl)picolinate 4 (1.0 g, 4.65 mol) was added and the mixture was heated to 80-90° C. for 2 h. The reaction was cooled down and 1N HCl solution (10 mL) was added to be acidic. Dichloromethane (100 mL) was then added and the organic phase was further washed with water (100 mL) and dried over sodium sulfate. The solvent was removed and the residue was mixed with ether (50 mL) and stirred for 0.5 h. The solid was filtered and dried to give N-(2-chlorophenyl)-5-(methylsulfonyl)picolinamide 5 as a light yellow solid. Yield: 1.26 g, 87.2%.

$^1$H-NMR (300 Hz, CDCl$_3$) δ (ppm): 10.6 (s, 1H), 9.21 (m, 1H), 8.62 (dd, 1H), 8.51 (dd, 1H), 8.46 (dd, 1H), 7.45 (dd, 1H), 7.34 (td, 1H), 7.12 (td, 1H), 3.20 (s, 3H).

(e) Preparation of N'-(2-chlorophenyl)-5-(methylsulfonyl)picolinimidohydrazide 7

N-(2-chlorophenyl)-5-(methylsulfonyl)picolinamide 5 (1.26 g, 0.0040 mol) in anhydrous benzene (20 mL) was added to PCl$_5$ (1.26 g, 6.0 mmol) and the mixture was heated to reflux overnight. The solvent was removed and the residue was further dried under high vacuum. Crude N-(2-chlorophenyl)-5-(methylsulfonyl)picolinimidoyl chloride 6 was obtained as a yellow solid (1.60 g). The N-(2-chlorophenyl)-5-(methylsulfonyl)picolinimidoyl chloride 6 was dissolved into anhydrous THF (30 mL) and the reaction was cooled down to 0° C. and hydrazine monohydrate (9.0 mL) was added. The reaction was kept at 0° C. for 10 min and warmed to ambient temperature in 0.5 h. The solvent was removed and the residue was purified by column chromatography (eluting with hexane and ethyl acetate 1:1) to give N'-(2-chlorophenyl)-5-(methylsulfonyl) picolinimidohydrazide 7 as a yellow solid. Yield: 1.22 g, 92.0%.

$^1$H-NMR (300 Hz, CDCl$_3$) δ (ppm): 9.02 (dd, 1H), 8.25 (dd, 1H), 8.17 (dd, 1H) 7.44 (s, 1H), 7.37 (dd, 1H), 7.16 (td, 1H), 6.89 (td, 1H), 6.45 (dd, 1H), 5.62 (s, 2H), 3.06 (s, 3H).

(f) Preparation of 3-(4-(2-chlorophenyl)-5-(5-(methylsulfonyl)pyridin-2-yl)-4H-1,2,4-triazol-3-yl)acrylic acid 8

To a 100 mL flask with N'-(2-chlorophenyl)-5-(methylsulfonyl) picolinimidohydrazide 7 (0.63 g, 1.94 mol) in anhydrous toluene (20 mL) was added maleic anhydride (0.20 g, 2.04 mol) and the reaction was kept at ambient temperature for 1 h and then heated to reflux for 3 h. After solvent was removed and the residue was dried under high vacuum to give 3-(4-(2-chlorophenyl)-5-(5-(methylsulfonyl)pyridin-2-yl)-4H-1,2,4-triazol-3-yl)acrylic acid 8 as a yellow solid. Yield: 0.75 g, 95.6%.

(g) Preparation of 4-cyano-benzoic acid hydrazide 9

To a solution of 4-cyano-benzoic acid methyl ester (1.0 g, 13 mmol) in 30 mL of MeOH was added 3 mL of $H_2NNH_2 \cdot H_2O$. The mixture was stirred at ambient temperature for 16 h. The solid was collected and washed with $CH_3OH$ to give 4-cyano-benzoic acid hydrazide 9 as a solid. Yield: 0.8 g, 80%.

$^1$HNMR (DMSO-$d_6$) δ (ppm): 7.93 (d, 4 H); 4.70 (s, 1 H); 3.30 (s, 2 H).

(h) Preparation of (E)-4-(5-(2-(4-(2-chlorophenyl)-5-(5-(methylsulfonyl)pyridin-2-yl)-4H-1,2,4-triazol-3-yl)vinyl)-1,3,4-oxadiazol-2-yl)benzonitrile (Compound (10))

To a 100 mL flask with compound 8 (0.21 g, 0.52 mmol) in dichlormethane (20 mL) was added oxalyl chloride (0.20 g, 1.55 mmol) and a drop of DMF. The reaction was kept at ambient temperature for 3 h. The solvent was removed and the residue was further dried under high vacuum and cooled to −20° C. Dichloromethane (10 mL) was added, followed by 4-cyanobenzohydrazide 9 (0.10 mg, 0.62 mmol) and triethylamine (0.5 mL). The reaction was kept at this temperature for 0.5 h and then room temperature for 1 h. The solvent was removed and the crude (E)-N'-(3-(4-(2-chlorophenyl)-5-(5-(methylsulfonyl)pyridin-2-yl)-4H-1,2,4-triazol-3-yl)acryloyl)-4-cyanobenzohydrazide 10 was used for the next step.

(E)-N'-(3-(4-(2-chlorophenyl)-5-(5-(methylsulfonyl)pyridin-2-yl)-4H-1,2,4-triazol-3-yl)acryloyl)-4-cyanobenzohydrazide 10 was dissolved into dichloromethane (10 mL) and triphenyl phosphine (0.27 g, 1.0 mmol), carbon tetrabromide (0.34 g, 1.04 mmol) and triethylamine (0.18 mL, 1.30 mmol) was added. The reaction was kept at ambient temperature for 2 h. The final compound was purified by column chromatography (eluting with hexane and ethyl acetate 1:3) to give (E)-4-(5-(2-(4-(2-chlorophenyl)-5-(5-(methylsulfonyl)pyridin-2-yl)-4H-1,2,4-triazol-3-yl)vinyl)-1,3,4-oxadiazol-2-yl)benzonitrile as a yellow solid. Yield: 0.035 g, 12.7%.

$^1$H-NMR (300 Hz, CDCl$_3$) δ ppm 8.74 (d, 1 H), 8.60 (d, 1 H), 8.32 (dd, 1 H), 8.17 (d, 2 H), 7.82 (d, 2 H), 7.63 (d, 1 H), 7.62 (m, 2 H), 7.49 (td, 1 H), 7.41 (dd, 1 H), 7.13 (d, 1 H), 3.06 (s, 3 H).

MS: 530.3 (M+H), 552.20 (M+Na).

HPLC: 98%.

EXAMPLE 14

Preparation of 2-(4-(2-chlorophenyl)-5-((E)-2-(5-(4-chlorophenyl)-1,3,4-oxadiazol-2-yl)vinyl)-4H-1,2,4-triazol-3-yl)-5-(methylsulfonyl)pyridine (Compound (14))

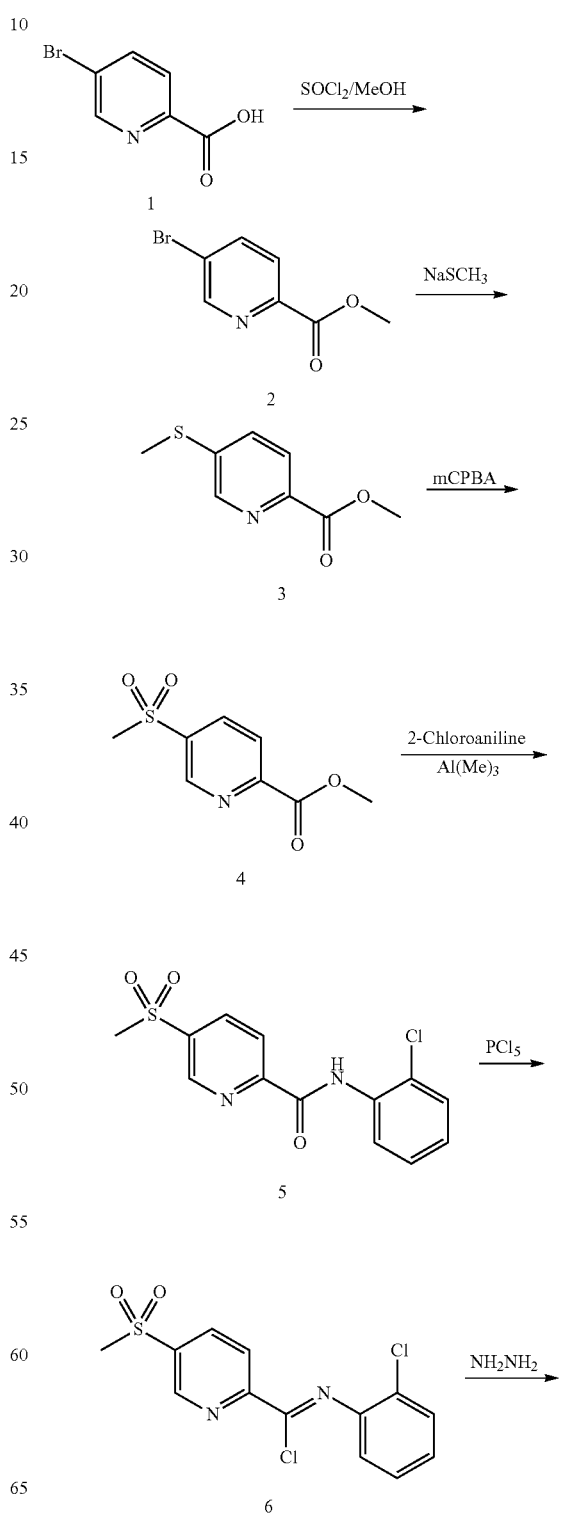

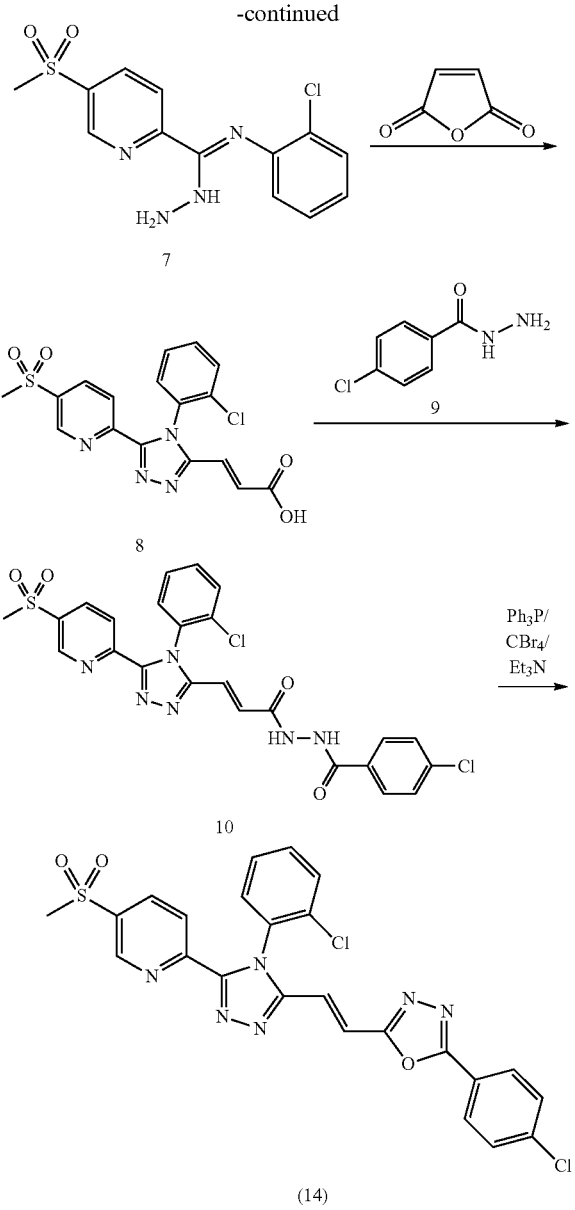

(a) Preparation of methyl 5-bromopicolinate 2

To a 100 mL round bottle flask with 5-bromopicolinic acid (7.0 g, 0.035 mol) in methanol (80 mL) was added thionyl chloride (3.0 mL) dropwise at ambient temperature. After the addition the reaction mixture was heated to reflux for 3 h. Methanol was removed and ethyl acetate (100 mL) was added to the residue and was adjusted pH to 7.0 by addition of sodium bicarbonate solution. The organic phase was separated and dried over sodium sulfate. The organic solvent was removed and methyl 5-bromopicolinate 2 was obtained as white solid which was used for the next step reaction without further purification. Yield: 6.57 g, 86.9%.

(b) Preparation of methyl 5-(methylthio)picolinate 3

A solution of methyl 5-bromopicolinate 2 (6.20 g, 0.0287 mol) in anhydrous THF (150 mL) was added to sodium methylthionide (2.51 g, 0.0359 mol), and the reaction was heated to reflux overnight. The solvent was removed and the residue was purified by column chromatography (eluting with hexane and ethyl acetate 1:1). Methyl 5-(methylthio)picolinate 3 as a white solid was isolated. Yield: 3.0 g, 57.1%.

$^1$H-NMR (300 Hz, CDCl$_3$) δ (ppm): 8.58 (d, 1H), 8.02 (d, 1H), 7.60 (dd, 1H), 3.99 (s, 3H), 2.58 (s, 3H).

(c) Preparation of methyl 5-(methylsulfonyl)picolinate 4

To a 100 mL round bottle flask with methyl 5-(methylthio) picolinate 3 (1.50 g, 0.0082 mol) in 30 mL of DCM was added mCPBA (5.51 g, 77%, 0.025 mol). The reaction was kept at ambient temperature overnight. After solvent was removed, the residue was purified by column chromatography (eluting with hexane and ethyl acetate 1:1) to give methyl 5-(methylsulfonyl)picolinate 4 as a white solid. Yield: 1.35 g, 76.5%.

$^1$H-NMR (300 Hz, CDCl$_3$) δ (ppm): 9.22 (d, 1H), 8.40 (dd, 1H), 8.36 (d, 1H), 4.02 (s, 3H), 3.10 (s, 3H).

(d) Preparation of N-(2-chlorophenyl)-5-(methylsulfonyl)picolinamide 5

2-Chloroaniline (1.20 g, 0.0093 mol) in toluene (20 mL) was added to trimethylaluminum (2.0 M 4.6 mL) then methyl 5-(methylsulfonyl)picolinate 4 (1.0 g, 0.00465 mol) was added and the mixture was heated to 80-90° C. for 2 h. The reaction was cooled down and 1N HCl solution (10 mL) was added to be acidic. Dichloromethane (100 mL) was then added and the organic phase was further washed with water (100 mL) and dried over sodium sulfate. The solvent was removed and the residue was mixed with ether (50 mL) and stirred for 0.5 h. The solid was filtered and dried to give N-(2-chlorophenyl)-5-(methylsulfonyl)picolinamide 5 as a light yellow solid. Yield: 1.26 g, 87.2%.

$^1$H-NMR (300 Hz, CDCl$_3$) δ (ppm): 10.6 (s, 1H), 9.21 (m, 1H), 8.62 (dd, 1H), 8.51 (dd, 1H), 8.46 (dd, 1H), 7.45 (dd, 1H), 7.34 (td, 1H), 7.12 (td, 1H), 3.20 (s, 3H).

(e) Preparation of N'-(2-chlorophenyl)-5-(methylsulfonyl)picolinimidohydrazide 7

N-(2-chlorophenyl)-5-(methylsulfonyl)picolinamide 5 (1.26 g, 0.0040 mol) in anhydrous benzene (20 mL) was added to PCl$_5$ (1.26 g, 0.0060 mol) and the mixture was heated to reflux overnight. The solvent was removed and the residue was further dried under high vacuum. Crude N-(2-chlorophenyl)-5-(methylsulfonyl)picolinimidoyl chloride 6 was obtained as a yellow solid (1.60 g). The compound 6 was dissolved into anhydrous THF (30 mL) and the reaction was cooled down to 0° C. and hydrazine hydrate (9.0 mL) was added. The reaction was kept at 0° C. for 10 min and warmed to ambient temperature in 0.5 h. The solvent was removed and the residue was purified by column chromatography (eluting with hexane and ethyl acetate 1:1) to give N'-(2-chlorophenyl)-5-(methylsulfonyl) picolinimidohydrazide 7 as a yellow solid. Yield: 1.22 g, 92.0%.

$^1$H-NMR (300 Hz, CDCl$_3$) δ (ppm): 9.02 (dd, 1H), 8.25 (dd, 1H), 8.17 (dd, 1H) 7.44 (s, 1H), 7.37 (dd, 1H), 7.16 (td, 1H), 6.89 (td, 1H), 6.45 (dd, 1H), 5.62 (s, 2H), 3.06 (s, 3H).

(f) Preparation of 3-(4-(2-chlorophenyl)-5-(5-(methylsulfonyl)pyridin-2-yl)-4H-1,2,4-triazol-3-yl)acrylic acid 8

To a 100 mL flask with N'-(2-chlorophenyl)-5-(methylsulfonyl) picolinimidohydrazide 7 (0.63 g, 0.00194 mol) in anhydrous toluene (20 ml) was added maleic anhydride (0.20 g, 0.00204 mol) and the reaction was kept at ambient temperature for 1 h and then heated to reflux for 3 h. After solvent was removed and the residue was dried under high vacuum to give 3-(4-(2-chlorophenyl)-5-(5-(methylsulfonyl)pyridin-2-yl)-4H-1,2,4-triazol-3-yl)acrylic acid 8 as a yellow solid. Yield: 0.75 g, 95.6%.

(g) Preparation of 2-(4-(2-chlorophenyl)-5-((E)-2-(5-(4-chlorophenyl)-1,3,4-oxadiazol-2-yl)vinyl)-4H-1,2,4-triazol-3-yl)-5-(methylsulfonyl)pyridine (Compound (14))

To a 100 mL flask with 3-(4-(2-chlorophenyl)-5-(5-(methylsulfonyl)pyridin-2-yl)-4H-1,2,4-triazol-3-yl)acrylic acid 8 (0.21 g, 0.52 mmol) in dichlormethane (20 mL) was added oxalyl chloride (0.20 g, 1.55 mmol) and a drop of DMF. The reaction was kept at ambient temperature for 3 h. The solvent was removed and the residue was further dried under high vacuum. Dichloromethane (10 mL) was added, followed by 4-chlorobenzohydrazide 9 (0.10 g, 0.6 mmol) and triethylamine (0.5 mL). The reaction was kept at this temperature for 0.5 h and then ambient temperature for 1 h. The solvent was removed and the crude 4-chloro-N'-[(E)-3-[4-(2-chlorophenyl)-5-(5-methylsulfonyl-2-pyridyl)-1,2,4-triazol-3-yl]prop-2-enoyl]benzohydrazide 10 was used for the next step.

4-chloro-N'-[(E)-3-[4-(2-chlorophenyl)-5-(5-methylsulfonyl-2-pyridyl)-1,2,4-triazol-3-yl]prop-2-enoyl]benzohydrazide 10 was dissolved into dichloromethane (10 mL) and triphenyl phosphine (0.27 g, 1.0 mmol), carbon tetrabromide (0.34 g, 1.04 mmol) and triethylamine (0.18 mL, 1.30 mmol) was added. The reaction was kept at room temperature for 2 h. The final compound was purified by column chromatography (eluting with hexane and ethyl acetate 1:3) to give 2-(4-(2-chlorophenyl)-5-((E)-2-(5-(4-chlorophenyl)-1,3,4-oxadiazol-2-yl)vinyl)-4H-1,2,4-triazol-3-yl)-5-(methylsulfonyl)pyridine as a yellow solid. Yield: 0.03 g, 11%.

¹H-NMR (300 Hz, CDCl₃) δ (ppm): 8.74 (d, 1H), 8.60 (d, 1H), 8.32 (dd, 1H), 8.17 (d, 2H),7.82 (d,2H), 7.63 (d,1H), 7.62 (m,2H), 7.49 (d, 1H), 7.41 (dd, 1H), 7.13 (d, 1H), 3.06 (s, 3H).

MS: 539.2 (MH⁺).

HPLC: 98%

EXAMPLE 15

Preparation of 4-{5-[4-(2-Chloro-phenyl)-5-(5-methanesulfonyl-pyridin-2-yl)-4H-[1,2,4]triazol-3-ylethynyl]-[1,3,4]oxadiazol-2-yl}-benzonitrile (Compound (33))

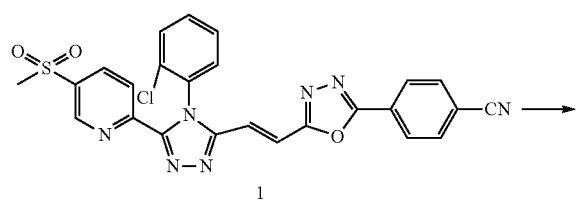

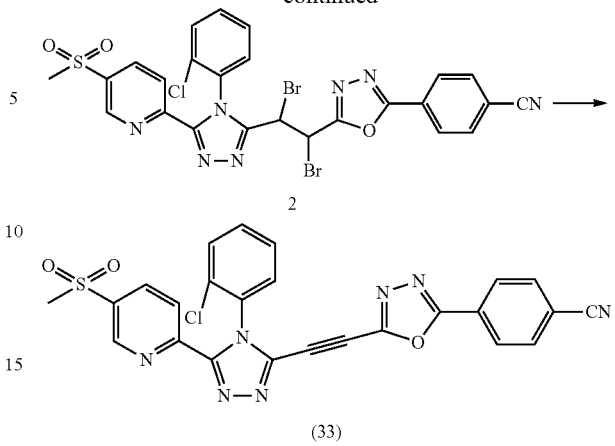

(a) Preparation of 4-(5-{1,2-Dibromo-2-[4-(2-chloro-phenyl)-5-(5-methanesulfonyl-pyridin-2-yl)-4H-[1,2,4]triazol-3-yl]-ethyl}-[1,3,4]oxadiazol-2-yl)-benzonitrile 2

To a solution of 4-(5-{2-[4-(2-Chloro-phenyl)-5-(5-methanesulfonyl-pyridin-2-yl)-4H-[1,2,4]triazol-3-yl]-vinyl}-[1,3,4]oxadiazol-2-yl)-benzonitrile 1 (0.1 g, 0.19 mmol) in DCM (10 mL) was added a solution of Br₂ (0.05 g, 0.28 mmol) in DCM (10 mL) dropwise at 0° C. The mixture was stirred at ambient temperature for 4 h, washed with NaHSO₃ (aq) and H₂O, dried over Na₂SO₄ and concentrated. The residue was subjected to FCC (50-100% ethyl acetate/hexanes) to afford 4-(5-{1,2-Dibromo-2-[4-(2-chloro-phenyl)-5-(5-methanesulfonyl-pyridin-2-yl)-4H-[1,2,4]triazol-3-yl]-ethyl}-[1,3,4]oxadiazol-2-yl)-benzonitrile 2. Yield: 0.1 g, 77%.

¹H-NMR (300 Hz, CDCl₃) δ (ppm): 8.78 (d, 1 H), 8.62 (d, 1 H), 8.38 (d, 1 H), 8.20 (d, 2 H), 7.80 (d, 2 H), 7.72-7.38 (m, 4 H), 6.62 (d, 1 H), 5.30 (d, 1 H), 3.09 (s, 3 H).

(b) Preparation of 4-{5-[4-(2-Chloro-phenyl)-5-(5-methanesulfonyl-pyridin-2-yl)-4H-[1,2,4]triazol-3-ylethynyl]-[1,3,4]oxadiazol-2-yl}-benzonitrile (Compound (33))

To a solution of 4-(5-{1,2-Dibromo-2-[4-(2-chloro-phenyl)-5-(5-methanesulfonyl-pyridin-2-yl)-4H-[1,2,4]triazol-3-yl]-ethyl}-[1,3,4]oxadiazol-2-yl)-benzonitrile 2 (0.1 g, 0.19 mmol) in benzene (10 mL) was added tBuOK (0.05 g, 0.28 mmol) portionwise at 0° C. The mixture was stirred at 0° C. for 1 h, treated with diluted acetic acid and ethyl acetate, washed with H₂O, dried over Na₂SO₄ and concentrated. The residue was subjected to FCC (50-100% ethyl acetate/hexanes) to afford 4-{5-[4-(2-Chloro-phenyl)-5-(5-methanesulfonyl-pyridin-2-yl)-4H-[1,2,4]triazol-3-ylethynyl]-[1,3,4]oxadiazol-2-yl}-benzonitrile. Yield: 0.03 g, 39%.

¹H-NMR (300 Hz, CDCl₃) δ (ppm): 8.78 (s, 1 H), 8.62 (d, 1 H), 8.38 (d, 1 H), 8.20 (d, 2 H), 7.82 (d, 2 H), 7.62-7.48 (m, 4 H), 3.09 (s, 3 H).

MS: 528.2 (MH⁺).

HPLC: 94%

EXAMPLE 16

Preparation of 2-(4-(2-chloro-4-trifluoromethoxyphenyl)-5-((E)-2-(5-(2-methoxypyridin-4-yl)-1,3,4-oxadiazol-2-yl)vinyl)-4H-1,2,4-triazol-3-yl)-5-(methylsulfonyl)pyridine (Compound (56))

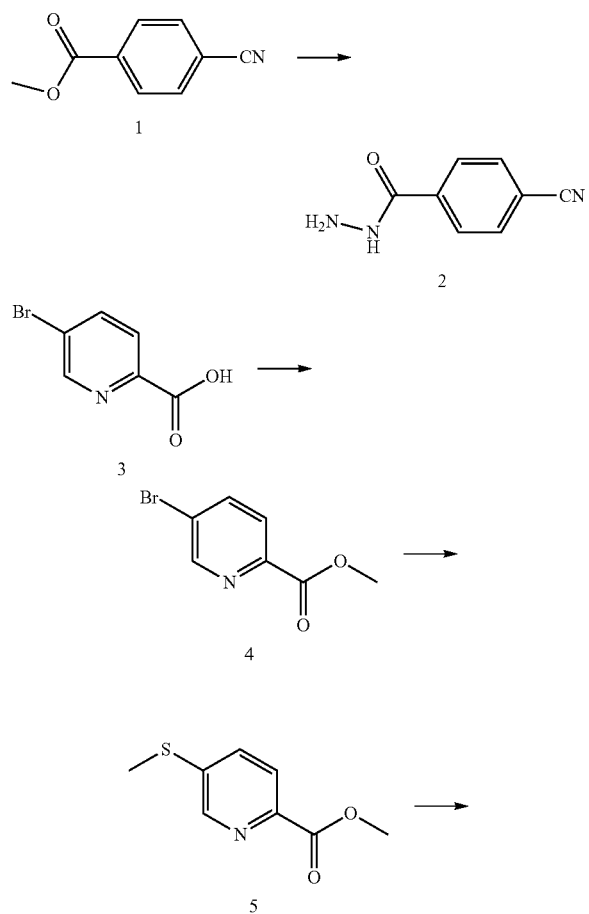

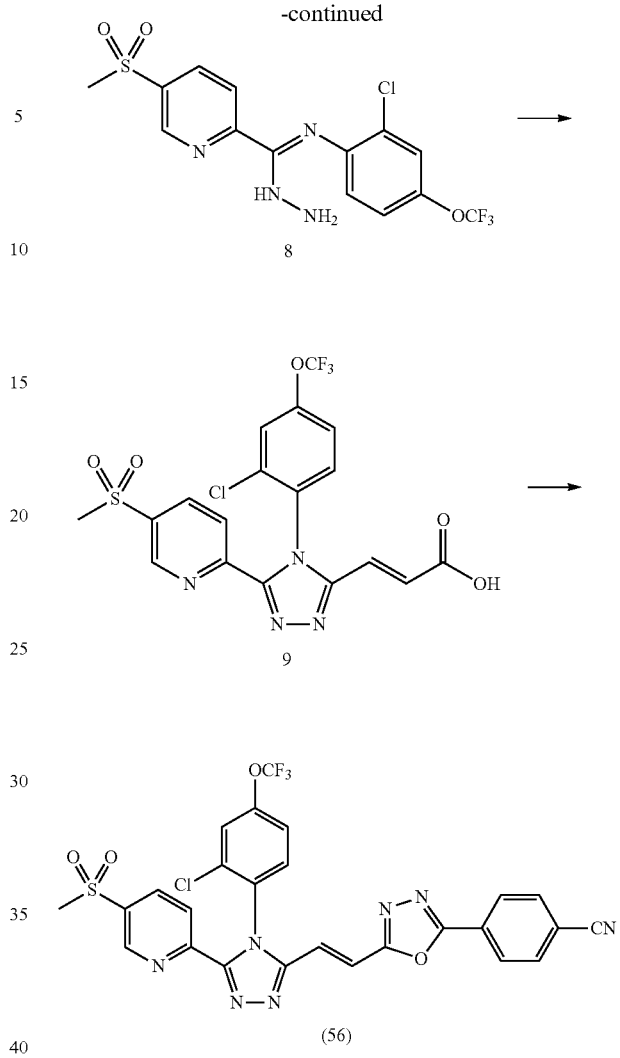

(a) Preparation of 4-Cyano-benzoic acid hydrazide 2

To a solution of 4-Cyano-benzoic acid methyl ester 1 (1.0 g, 13 mmol) in 30 mL of MeOH was added 3 mL of $H_2NNH_2.H_2O$. The mixture was stirred at ambient temperature for 16 h. The solid was collected and washed with $CH_3OH$ to give 4-Cyano-benzoic acid hydrazide 2 as a solid. Yield: 0.8 g, 80%.

$^1$HNMR (DMSO-$d_6$) δ (ppm): 7.93 (d, 4 H); 4.70 (s, 1 H); 3.30 (s, 2 H).

(b) Preparation of methyl 5-bromopicolinate 4

To a 100 mL round bottle flask with 5-bromopicolinic acid 3 (7.0 g, 35 mmol) in methanol (80 mL) was added dropwise thionyl chloride (3.0 mL) at ambient temperature. After addition the reaction mixture was heated to reflux for 3 h. Methanol was removed and ethyl acetate (100 mL) was added to the residue and was adjusted pH to 7.0 by addition of sodium bicarbonate solution. The organic phase was separated and dried over sodium sulfate. The organic solvent was removed and methyl 5-bromopicolinate 4 was obtained as a white solid which was used for next step without further purification. Yield: 6.57 g, 86.9%.

(c) Preparation of methyl 5-(methylthio)picolinate 5

A solution of methyl 5-bromopicolinate 4 (6.20 g, 28.7 mmol) in anhydrous THF (150 mL) was added to sodium methylhionide (2.51 g, 35.9 mmol) and the reaction was heated to reflux overnight. The solvent was removed and the residue was purified by column chromatography (eluting with hexane and ethyl acetate 1:1). Methyl 5-(methylthio) picolinate 5 as a white solid was isolated. Yield: 3.0 g, 57.1%.

$^1$H-NMR (300 Hz, CDCl$_3$) δ ppm 8.58 (d, 1 H), 8.02 (d, 1 H), 7.60 (dd, 1 H), 3.99 (s, 3 H), 2.58 (s, 3 H).

(d) Preparation of methyl 5-(methylsulfonyl)picolinate 6

To a 100 mL round bottle flask with methyl 5-(methylthio) picolinate 5 (1.50 g, 8.2 mmol) in 30 mL of DCM was added mCPBA (5.51 g, 77%, 25.0 mmol). The reaction was kept at ambient temperature overnight. After solvent was removed, the residue was purified by column chromatography (eluting with hexane and ethyl acetate 1:1) to give methyl 5-(methylsulfonyl)picolinate 6 as a white solid. Yield: 1.35 g, 76.5%.

$^1$H-NMR (300 Hz, CDCl$_3$) δ (ppm): 9.22 (d, 1H), 8.40 (dd, 1H), 8.36 (d, 1H), 4.02 (s, 3H), 3.10 (s, 3H).

(e) Preparation of 5-Methanesulfonyl-pyridine-2-carboxylic acid (2-chloro-4-trifluoromethoxy-phenyl)-amide 7

2-Chloro-4-trifluoromethoxy-phenylamine (2.0 g, 9.29 mmol) in toluene (50 mL) was added to trimethylaluminum (2.0 M 4.65 mL) then methyl 5-(methylsulfonyl)picolinate 6 (1.0 g, 4.65 mol) was added and the mixture was heated to 80-90° C. for 2 h. The reaction was cooled down and 1N HCl solution (10 mL) was added to be acidic. Dichloromethane (100 mL) was then added and the organic phase was further washed with water (100 mL) and dried over sodium sulfate. The solvent was removed and the residue was mixed with ether (50 mL) and stirred for 0.5 h. The solid was filtered and dried to give 5-methanesulfonyl-pyridine-2-carboxylic acid (2-chloro-4-trifluoromethoxy-phenyl)-amide 7 as a light yellow solid. Yield: 1.26 g, 65%.

$^1$H-NMR (300 Hz, CDCl$_3$) δ (ppm): 10.6 (s, 1H), 9.21 (m, 1H), 8.68 (dd, 1H), 8.52 (dd, 1H), 7.40 (dd, 1H), 7.22 (m, 2H), 3.20 (s, 3H).

(f) Preparation of N'-(2-chloro-4-trifluoromethoxyphenyl)-5-(methylsulfonyl)picolinimidohydrazide 8

5-Methanesulfonyl-pyridine-2-carboxylic acid (2-chloro-4-trifluoromethoxy-phenyl)-amide 7 (1.1 g, 2.79 mmol) in benzene (20 mL) was added to PCl$_5$ (1.26 g, 6.0 mmol) and the mixture was heated to reflux overnight. The solvent was removed and the residue was further dried under high vacuum. Crude N-(2-chloro-4-trifluoromethoxyphenyl)-5-(methylsulfonyl)picolinimidoyl chloride was obtained as a yellow solid (1.60 g). The N-(2-chlor-4-trifluoromethoxyophenyl)-5-(methylsulfonyl)picolinimidoyl chloride was dissolved into anhydrous THF (30 mL) and the reaction was cooled down to 0° C. and hydrazine monohydrate (9.0 mL) was added. The reaction was kept at 0° C. for 10 min and warmed to ambient temperature in 0.5 h. The solvent was removed and the residue was purified by column chromatography (eluting with hexane and ethyl acetate 1:1) to give N'-(2-chloro-4-trifluoromethoxyphenyl)-5-(methylsulfonyl) picolinimidohydrazide 8 as a yellow solid. Yield: 0.56 g, 50%.

$^1$H-NMR (300 Hz, CDCl$_3$) δ (ppm): 9.02 (dd, 1H), 8.25 (dd, 2H), 7.44 (s, 1H), 7.32 (dd, 1H), 7.06 (td, 1H), 6.41 (td, 1H), 5.62 (s, 2H), 3.08 (s, 3H).

(g) Preparation of 3-(4-(2-chlorophenyl)-5-(5-(methylsulfonyl)pyridin-2-yl)-4H-1,2,4-triazol-3-yl)acrylic acid 9

To a 100 mL flask with N'-(2-chloro-4-trifluoromethoxyphenyl)-5-(methylsulfonyl)picolinimidohydrazide 8 (0.45 g, 1.1 mmol) in anhydrous toluene (20 mL) was added maleic anhydride (0.20 g, 2.04 mol) and the reaction was kept at ambient temperature for 1 h and then heated to reflux for 3 h. After solvent was removed, the residue was dried under high vacuum to give 3-(4-(2-chloro-4-trifluoromethoxyphenyl)-5-(5-(methylsulfonyl)pyridin-2-yl)-4H-1,2,4-triazol-3-yl) acrylic acid 9 as a yellow solid which was used for the next step without further purification. Yield: 0.75 g, 95.6%.

(h) Preparation of 2-(4-(2-chloro-4-trifluoromethoxyphenyl)-5-((E)-2-(5-(2-methoxypyridin-4-yl)-1,3,4-oxadiazol-2-yl)vinyl)-4H-1,2,4-triazol-3-yl)-5-(methylsulfonyl)pyridine (Compound (56))

To a 100 mL flask with 3-(4-(2-chloro-4-trifluoromethoxyphenyl)-5-(5-(methylsulfonyl)pyridin-2-yl)-4H-1,2,4-triazol-3-yl)acrylic acid 9 (0.18 g, 0.368 mmol) in dichlormethane (20 mL) was added oxalyl chloride (0.20 g, 1.55 mmol) and a drop of DMF. The reaction was kept at ambient temperature for 3 h. The solvent was removed and the residue was further dried under high vacuum and cooled to −20° C. Dichloromethane (10 mL) was added, followed by 4-Cyanobenzoic acid hydrazide 2 (0.18 g, 1.1 mmol) and triethylamine (0.5 mL). The reaction mixture was kept at this temperature for 0.5 h and then ambient temperature for 1 h. The solvent was removed and the crude N'-[(E)-3-[4-(2-chloro-4-trifluoromethoxyphenyl)-5-(5-methylsulfonyl-2-pyridyl)-1, 2,4-triazol-3-yl]prop-2-enoyl]-2-methoxy-pyridine-4-carbohydrazide was used for the next step.

N'-[(E)-3-[4-(2-chloro-4-trifluoromethoxyphenyl)-5-(5-methylsulfonyl-2-pyridyl)-1,2,4-triazol-3-yl]prop-2-enoyl]-2-methoxy-pyridine-4-carbohydrazide was dissolved into dichloromethane (10 mL), and triphenylphosphine (0.19 g, 0.736 mmol), carbon tetrabromide (0.24 g, 0.736 mmol) and triethylamine (0.18 mL, 1.30 mmol) was added. The reaction mixture was kept at ambient temperature for 2 h. The final compound was purified by column chromatography (eluting with hexane and ethyl acetate 1:3) to give 2-(4-(2-chloro-4-trifluoromethoxyphenyl)-5-((E)-2-(5-(2-methoxypyridin-4-yl)-1,3,4-oxadiazol-2-yl)vinyl)-4H-1,2,4-triazol-3-yl)-5-(methylsulfonyl)pyridine as a yellow solid. Yield: 0.07 g, 30%.

$^1$H-NMR (300 Hz, CDCl$_3$) δ (ppm): 8.78 (d, 1 H), 8.62 (d, 1 H), 8.20 (d, 2 H), 7.78-7.62 (m, 3H), 7.58-7.32 (m, 4 H), 7.12 (d, 1 H), 3.09 (s, 3 H).

MS: 614.2 (MH$^+$).

HPLC: 96%

EXAMPLE 17
Preparation of 4-[5-(2-{4-(2-Chloro-phenyl)-5-[5-(2,2,2-trifluoro-ethoxy)-pyridin-2-yl]-4H-[1,2,4]triazol-3-yl}-vinyl)-[1,3,4]oxadiazol-2-yl]-benzonitrile (Compound (57))
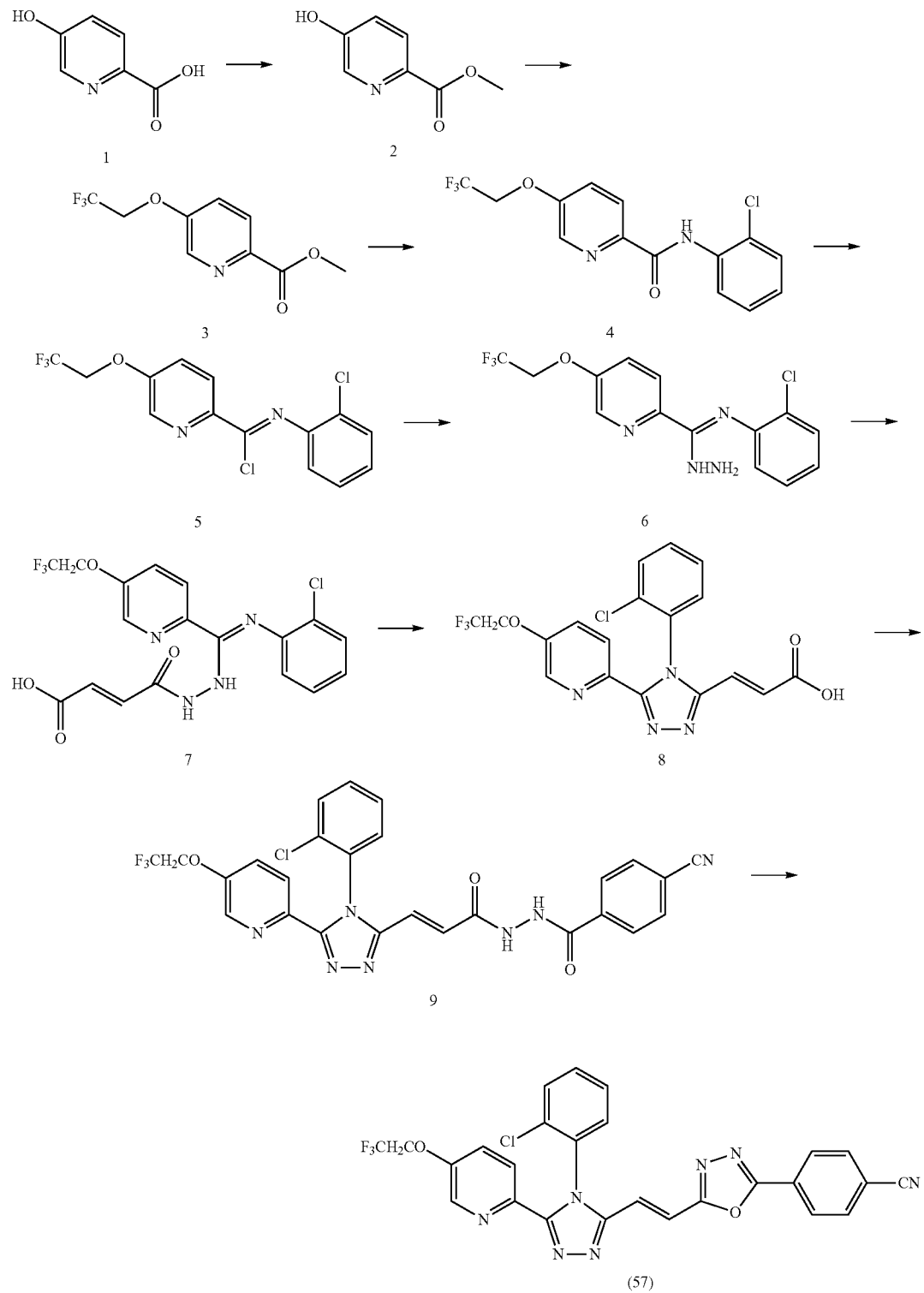

(a) Preparation of 5-Hydroxy-pyridine-2-carboxylic acid methyl ester 2

To a 100 mL round bottle flask with 5-Hydroxy-pyridine-2-carboxylic acid 1 (1.0 g, 7.2 mmol) in methanol (50 mL) was added dropwise thionyl chloride (3.0 mL) at ambient temperature. After addition the reaction mixture was heated to reflux for 3 h. Methanol was removed to give 5-Hydroxy-pyridine-2-carboxylic acid methyl ester 2 as a white solid which was used for the next step without further purification. Yield: 0.957 g, 86.9%.

(b) Preparation of 5-(2,2,2-Trifluoro-ethoxy)-pyridine-2-carboxylic acid methyl ester 3

A mixture of 5-Hydroxy-pyridine-2-carboxylic acid methyl ester 2 (0.5 g, 3.26 mmol), methanesulfonic acid 2,2,2-trifluoro-ethyl ester (1.0 g, 5.34 mmol) and $K_2CO_3$ (1.4 g, 9.8 mmol) in acetonitrile (50 mL) was stirred overnight. The solid was filtered off and the filtrate was concentrated. The residue was purified by column chromatography (eluting with hexane and ethyl acetate 1:1) to afford 5-(2,2,2-Trifluoro-ethoxy)-pyridine-2-carboxylic acid methyl ester 3 as a white solid. Yield: 0.437 g, 57.1%.

$^1$H-NMR (300 Hz, $CDCl_3$) δ (ppm): 8.48 (d, 1 H), 8.16 (d, 1 H), 7.38 (dd, 1 H), 4.48 (q, 2 H), 3.99 (s, 3 H).

(c) Preparation of 5-(2,2,2-Trifluoro-ethoxy)-pyridine-2-carboxylic acid (2-chloro-phenyl)-amide 4

2-Chloro-4-trifluoromethoxy-phenylamine (2.0 g, 9.29 mmol) in toluene (50 mL) was added to trimethylaluminum (2.0 M 4.65 mL) then 5-(2,2,2-Trifluoro-ethoxy)-pyridine-2-carboxylic acid methyl ester 3 (1.1 g, 4.65 mol) was added and the mixture was heated to 80-90° C. for 2 h. The reaction was cooled down and 1N HCl solution (10 mL) was added to be acidic. Dichloromethane (100 mL) was then added and the organic phase was further washed with water (100 mL) and dried over sodium sulfate. The solvent was removed and the residue was mixed with ether (50 mL) and stirred for 0.5 h. The solid was filtered and dried to give 5-(2,2,2-Trifluoro-ethoxy)-pyridine-2-carboxylic acid (2-chloro-phenyl)-amide 4 as a solid. Yield: 1.0 g, 71%.

$^1$H-NMR (300 Hz, $CDCl_3$) δ (ppm): 10.6 (s, 1H), 8.62 (dd, 1H), 8.40 (dd, 1H), 7.32 (dd, 1H), 7.46-7.30 (m, 3H), 7.12-7.08 (m, 1 H).

(d) Preparation of N'-(2-chlorophenyl)-5-(2,2,2-Trifluoro-ethoxy)picolinimidohydrazide 6

To a solution of 5-(2,2,2-Trifluoro-ethoxy)-pyridine-2-carboxylic acid (2-chloro-phenyl)-amide 4 (1.0 g, 3 mmol) in benzene (20 mL) was added $PCl_5$ (1.26 g, 6.0 mmol) and the mixture was heated to reflux overnight. The solvent was removed and the residue was further dried under high vacuum. The crude N-(2-Chloro-phenyl)-5-(2,2,2-trifluoro-ethoxy)-pyridine-2-carboximidoyl chloride was dissolved into anhydrous THF (20 mL) and the reaction was cooled down to 0° C. and hydrazine monohydrate (5.0 mL) was added. The reaction was kept at 0° C. for 10 min and warmed to ambient temperature in 0.5 h. The solvent was removed and the residue was purified by column chromatography (eluting with hexane and ethyl acetate 1:1) to give N'-(2-chloro-phenyl)-5-(2,2,2-Trifluoro-ethoxy)picolinimidohydrazide 6 as a yellow solid. Yield: 0.56 g, 50%.

$^1$H-NMR (300 Hz, $CDCl_3$) δ (ppm): 8.25 (dd, 1H), 8.02 (dd, 1H), 7.44 (s, 1H), 7.38 (dd, 1H), 7.30 (dd, 1H), 7.18 (td, 1H), 6.82 (td, 1H), 6.52 (d, 1H), 5.32 (s, 2H), 4.40 (q, 2H).

(e) Preparation of 3-{4-(2-Chloro-phenyl)-5-[5-(2,2,2-trifluoro-ethoxy)-pyridin-2-yl]-4H-[1,2,4]triazol-3-yl}-acrylic acid 8

To a 100 mL flask with N'-(2-chloro-4-phenyl)-5-(2,2,2-Trifluoro-ethoxy)picolinimidohydrazide 6 (0.45 g, 1.1 mmol) in anhydrous toluene (20 mL) was added maleic anhydride (0.20 g, 2.04 mol) and the reaction was kept at ambient temperature for 1 h and then heated to reflux for 3 h. After solvent was removed and the residue was dried under high vacuum to give 3-{4-(2-Chloro-phenyl)-5-[5-(2,2,2-trifluoro-ethoxy)-pyridin-2-yl]-4H-[1,2,4]triazol-3-yl}-acrylic acid 8 as a yellow solid which was used for the next step without further purification. Yield: 0.75 g, 95.6%.

(f) Preparation of 4-[5-(2-{4-(2-Chloro-phenyl)-5-[5-(2,2,2-trifluoro-ethoxy)-pyridin-2-yl]-4H-[1,2,4]triazol-3-yl}-vinyl)-[1,3,4]oxadiazol-2-yl]-benzonitrile (Compound (57))

To a 100 mL flask with 3-{4-(2-Chloro-phenyl)-5-[5-(2,2,2-trifluoro-ethoxy)-pyridin-2-yl]-4H-[1,2,4]triazol-3-yl}-acrylic acid 8 (0.18 g, 0.368 mmol) in dichloromethane (20 mL) was added oxalyl chloride (0.20 g, 1.55 mmol) and a drop of DMF. The reaction was kept at ambient temperature for 3 h. The solvent was removed and the residue was further dried under high vacuum and cooled to −20° C. Dichloromethane (10 mL) was added, followed by 4-Cyano-benzoic acid hydrazide (0.18 g, 1.1 mmol) and triethylamine (0.5 mL). The reaction mixture was kept at this temperature for 0.5 h and then ambient temperature for 1 h. The solvent was removed and the crude 4-Cyano-benzoic acid N'-(3-{4-(2-chloro-phenyl)-5-[5-(2,2,2-trifluoro-ethoxy)-pyridin-2-yl]-4H-[1,2,4]triazol-3-yl}-acryloyl)-hydrazide was used for the next step. 4-Cyano-benzoic acid N'-(3-{4-(2-chloro-phenyl)-5-[5-(2,2,2-trifluoro-ethoxy)-pyridin-2-yl]-4H-[1,2,4]triazol-3-yl}-acryloyl)-hydrazide was dissolved in dichloromethane (10 mL) and triphenylphosphine (0.19 g, 0.736 mmol), carbon tetrabromide (0.24 g, 0.736 mmol) and triethylamine (0.18 mL, 1.30 mmol) were added. The reaction mixture was kept at ambient temperature for 2 h. The final compound was purified by column chromatography (eluting with hexane and ethyl acetate 1:3) to give 4-[5-(2-{4-(2-Chloro-phenyl)-5-[5-(2,2,2-trifluoro-ethoxy)-pyridin-2-yl]-4H-[1,2,4]triazol-3-yl}-vinyl)-[1,3,4]oxadiazol-2-yl]-benzonitrile as a yellow solid. Yield: 0.07 g, 30%.

$^1$H-NMR (300 Hz, $CDCl_3$) δ (ppm): 8.38 (dd, 1 H), 8.20 (d, 2 H), 8.00 (dd, 1H), 7.80 (d, 2 H), 7.58-7.32 (m, 6 H), 7.18 (d, 1 H), 4.40 (q, 2 H). MS: 550.3 ($MH^+$). HPLC: 96%

EXAMPLE 18
Preparation of 4-(5-{2-[4-(2-Chloro-phenyl)-5-(5-methanesulfonyl-pyridin-2-yl)-4H-[1,2,4]triazol-3-yl]-1,2-difluoro-vinyl}-[1,3,4]oxadiazol-2-yl)-benzonitrile (Compound (58))
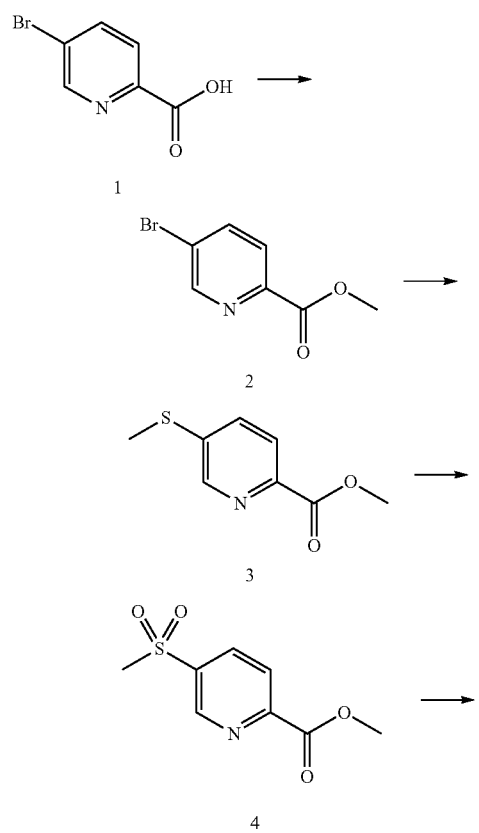
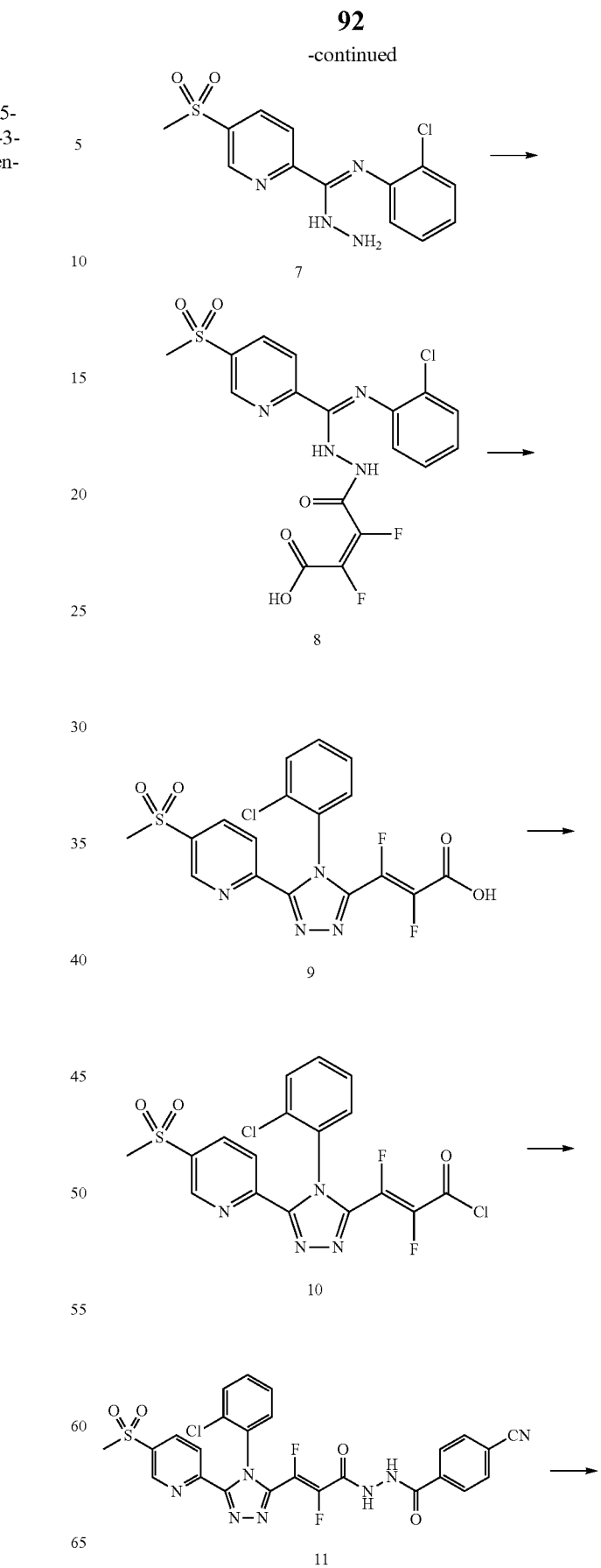

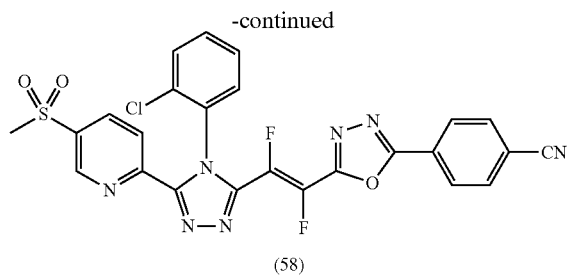

(58)

(a) Preparation of Methyl 5-bromopicolinate 2

To a 100 mL round bottle flask with 5-bromopicolinic acid (7.0 g, 35 mmol) in methanol (60 mL) was added dropwise thionyl chloride (3.0 mL) at ambient temperature. After addition the reaction mixture was heated to reflux for 3 h. Methanol was removed and ethyl acetate (80 mL) was added to the residue and was adjusted pH to 7.0 by addition of sodium bicarbonate solution. The organic phase was separated and dried over sodium sulfate. The organic solvent was removed and methyl 5-bromopicolinate 2 was obtained as a white solid which was used for the next step of the reaction without further purification. Yield: 6.57 g, 86.9%.

(b) Preparation of Methyl 5-(methylthio)picolinate 3

A solution of methyl 5-bromopicolinate 2 (6.20 g, 28.7 mmol) in anhydrous THF (150 mL) was added to sodium methylhionide (2.51 g, 35.9 mmol), the reaction was heated to reflux overnight. The solvent was removed and the residue was purified by column chromatography (eluting with hexane and ethyl acetate 1:1). Methyl 5-(methylthio)picolinate 3 as a white solid was isolated. Yield: 3.0 g, 57.1%.

$^1$H-NMR (300 Hz, CDCl$_3$) δ ppm 8.58 (d, 1 H), 8.02 (d, 1 H), 7.60 (dd, 1 H), 3.99 (s, 3 H), 2.58 (s, 3 H).

(c) Preparation of Methyl 5-(methylsulfonyl)picolinate 4

To a 100 mL round bottle flask with methyl 5-(methylthio) picolinate 3 (1.50 g, 8.2 mmol) in 30 mL of DCM was added mCPBA (5.51 g, 77%, 25.0 mmol). The reaction was kept at ambient temperature overnight. After solvent was removed, the residue was purified by column chromatography (eluting with hexane and ethyl acetate 1:1) to give methyl 5-(methylsulfonyl)picolinate 4 as a white solid. Yield: 1.35 g, 76.5%.

$^1$H-NMR (300 Hz, CDCl$_3$) δ (ppm): 9.22 (d, 1H), 8.40 (dd, 1H), 8.36 (d, 1H), 4.02 (s, 3H), 3.10 (s, 3H).

(d) Preparation of N-(2-chlorophenyl)-5-(methylsulfonyl)picolinamide 5

2-Chloroaniline (1.20 g, 0.0093 mol) in toluene (20 mL) was added to trimethylaluminum (2.0 M 4.6 mL) then methyl 5-(methylsulfonyl)picolinate 4 (1.0 g, 4.65 mol) was added and the mixture was heated to 80-90° C. for 2 h. The reaction was cooled down and 1N HCl solution (10 mL) was added to be acidic. Dichloromethane (100 mL) was then added and the organic phase was further washed with water (100 mL) and dried over sodium sulfate. The solvent was removed and the residue was mixed with ether (50 mL) and stirred for 0.5 h. The solid was filtered and dried to give N-(2-chlorophenyl)-5-(methylsulfonyl)picolinamide 5 as a light yellow solid. Yield: 1.26 g, 87.2%.

$^1$H-NMR (300 Hz, CDCl$_3$) δ (ppm): 10.6 (s, 1H), 9.21 (m, 1H), 8.62 (dd, 1H), 8.51 (dd, 1H), 8.46 (dd, 1H), 7.45 (dd, 1H), 7.34 (td, 1H), 7.12 (td, 1H), 3.20 (s, 3H).

(e) Preparation of N'-(2-chlorophenyl)-5-(methylsulfonyl)picolinimidohydrazide 7

N-(2-chlorophenyl)-5-(methylsulfonyl)picolinamide 5 (1.26 g, 0.0040 mol) in anhydrous benzene (20 mL) was added to PCl$_5$ (1.26 g, 6.0 mmol) and the mixture was heated to reflux overnight. The solvent was removed and the residue was further dried under high vacuum. Crude N-(2-chlorophenyl)-5-(methylsulfonyl)picolinimidoyl chloride 6 was obtained as a yellow solid (1.60 g). The N-(2-chlorophenyl)-5-(methylsulfonyl)picolinimidoyl chloride 6 was dissolved into anhydrous THF (30 mL) and the reaction was cooled down to 0° C. and hydrazine monohydrate (9.0 mL) was added. The reaction was kept at 0° C. for 10 min and warmed to ambient temperature in 0.5 h. The solvent was removed and the residue was purified by column chromatography (eluting with hexane and ethyl acetate 1:1) to give N'-(2-chlorophenyl)-5-(methylsulfonyl) picolinimidohydrazide 7 as a yellow solid. Yield: 1.22 g, 92.0%.

$^1$H-NMR (300 Hz, CDCl$_3$) δ (ppm): 9.02 (dd, 1H), 8.25 (dd, 1H), 8.17 (dd, 1H) 7.44 (s, 1H), 7.37 (dd, 1H), 7.16 (td, 1H), 6.89 (td, 1H), 6.45 (dd, 1H), 5.62 (s, 2H), 3.06 (s, 3H).

(f) Preparation of 3-[4-(2-Chloro-phenyl)-5-(5-methanesulfonyl-pyridin-2-yl)-4H-[1,2,4]triazol-3-yl]-2,3-difluoro-acrylic acid 9

To a 100 mL flask with N'-(2-chlorophenyl)-5-(methylsulfonyl)picolinimidohydrazide 7 (0.84 g, 2.59 mmol) in anhydrous toluene (20 mL) was added 3,4-difluoro-furan-2,5-dione (0.36 g, 2.59 mmol) and the reaction was kept at ambient temperature for 1 h to give (2Z)-3-((Z)—N'-(2-chlorophenyl)-5-(methylsulfonyl)pyridine-2-carboxamidocarbamoyl)-2,3-difluoroacrylic acid 8 and then heated to reflux for 3 h. After solvent was removed the residue was dried under high vacuum to give 3-[4-(2-chloro-phenyl)-5-(5-methanesulfonyl-pyridin-2-yl)-4H-[1,2,4]triazol-3-yl]-2,3-difluoro-acrylic acid 9 as a yellow solid (1.15 g, 96%) which was used for the next step without further purification.

(g) Preparation of 4-(5-{2-[4-(2-Chloro-phenyl)-5-(5-methanesulfonyl-pyridin-2-yl)-4H-[1,2,4]triazol-3-yl]-1,2-difluoro-vinyl}-[1,3,4]oxadiazol-2-yl)-benzonitrile (Compound (58))

To a 100 mL flask with 3-[4-(2-chloro-phenyl)-5-(5-methanesulfonyl-pyridin-2-yl)-4H-[1,2,4]triazol-3-yl]-2,3-difluoro-acrylic acid 9 (0.3 g, 0.68 mmol) in dichloromethane (20 mL) was added oxalyl chloride (0.40 g, 3.1 mmol) and a drop of DMF. The reaction was kept at ambient temperature for 3 h. The solvent was removed and the residue was further dried under high vacuum and cooled to −20° C. Dichloromethane (10 mL) was added, followed by 4-cyano-benzoic acid hydrazide 9 (0.33 g, 2.04 mmol) and triethylamine (0.5 mL). The reaction mixture was kept at this temperature for 0.5 h and then ambient temperature for 1 h. The solvent was removed and the crude 4-cyano-benzoic acid N'-{3-[4-(2-chloro-phenyl)-5-(5-methanesulfonyl-pyridin-2-yl)-4H-[1,2,4]triazol-3-yl]-2,3-difluoro-acryloyl}-hydrazide 11 was used for the next step.

4-Cyano-benzoic acid N'-{3-[4-(2-chloro-phenyl)-5-(5-methanesulfonyl-pyridin-2-yl)-4H-[1,2,4]triazol-3-yl]-2,3-difluoro-acryloyl}-hydrazide 11 was dissolved into dichloromethane (10 mL) and triphenylphosphine (0.27 g, 1.02 mmol), carbon tetrabromide (0.34 g, 1.02 mmol) and triethylamine (0.18 mL, 1.30 mmol) were added. The reaction mixture was kept at ambient temperature for 2 h. The final compound was purified by column chromatography (eluting with methanol/DCM 1/99-5/95) to give 4-(5-{2-[4-(2-chloro-phenyl)-5-(5-methanesulfonyl-pyridin-2-yl)-4H-[1,2,4]triazol-3-yl]-1,2-difluoro-vinyl}-[1,3,4]oxadiazol-2-yl)-benzonitrile as a solid. Yield: 0.05 g, 13%.

$^1$H-NMR (300 Hz, CDCl$_3$) δ (ppm): 8.77 (s, 1 H), 8.61 (d, 1 H), 8.38 (d, 1 H), 8.10 (d, 2 H), 7.80 (d, 2 H), 7.58-7.51 (m, 3 H), 7.46-7.41 (m, 1 H), 3.10 (s, 3 H).

MS: 566.2 (MH$^+$).

HPLC: 95%

EXAMPLE 19

IC$_{50}$ Values of Compounds

IC$_{50}$ values were calculated using STF/REN HEK293 cells (stably transfected with ST-Luc (7×TCF binding sites) and Renilla (Promega) plasmids). HEK293 cells (80,000 cells per well) were seeded in 96-well plates coated with poly-L lysine. 24 hours after seeding, the cells were incubated for an additional 24 hours with various compound concentrations in 50% Wnt3a containing conditioned media (from L Wnt3a-expressing cells (ATCC)). A minimum of three replicates was used for each sample. After compound exposure, the cells were lysed and the firefly luciferase and Renilla activities were measured on a GloMax® 96 Microplate Luminometer with Dual Injectors (Promega).

XLfit (idbs) was used to determine the IC$_{50}$ values in inhibition experiments. The data were fit to the following formula:

IC$_{50}$: Langmuir Binding Isotherm:

$$\text{fit}=((A+(B*x))+(((C-B)*(1-\exp((-1*D)*x)))/D))$$

$$\text{res}=(y-\text{fit})$$

Table 1 shows the IC$_{50}$ values of certain compounds. All values shown are average values from multiple experiments.

TABLE 1

| Compound No. | IC$_{50}$ μM | ±Standard Deviation |
| --- | --- | --- |
| (1) | 0.94 | 0.01 |
| (2) | 0.28 | 0.01 |
| (3) | 0.19 | 0.01 |
| (4) | 0.24 | 0.00 |
| (5) | >10 | |
| (6) | 1.2 | 0.23 |
| (7) | >10 | |
| (8) | 6.3 | 0.11 |
| (10) | 0.05 | 0.02 |
| (11) | 0.08 | 0.05 |
| (12) | 0.07 | 0.02 |
| (13) | 0.11 | 0.04 |
| (14) | 0.04 | 0.01 |
| (33) | 3.6 | 0.84 |
| (56) | 0.39 | 0.14 |
| (57) | 0.10 | 0.13 |
| (58) | >10 | |

EXAMPLE 20

Stability of Compounds

Experimental Procedure

Pooled human or rat liver microsomes (pooled male and female) were prepared and stored at −80° C. prior to use. Microsomes (final protein concentration 0.5 mg/mL), 0.1M phosphate buffer (pH 7.4) and the test compound (final substrate concentration=3 μM; final DMSO concentration=0.25%) were pre-incubated at 37° C. prior to the addition of NADPH (final concentration=1 mM) to initiate the reaction. The final incubation volume was 25 μL. A control incubation was included for each compound tested in which 0.1M phosphate buffer (pH 7.4) was added instead of NADPH (minus NADPH). Two control compounds were included with each species. All incubations were performed singularly for each test compound.

Each compound was incubated for 0, 5, 15, 30 and 45 mins. The control (minus NADPH) was incubated for 45 mins only. The reactions were stopped by the addition of 50 μL methanol containing internal standard at the appropriate time points. The incubation plates were centrifuged at 2,500 rpm for 20 mins at 4° C. to precipitate the protein.

Quantitative Analysis

Following protein precipitation, the sample supernatants were combined in cassettes of up to 4 compounds and analysed using Cyprotex generic LC-MS/MS conditions. Optionally, if metabolite profiling was requested following the stability assay a second assay was performed in which the compound was incubated four times and the four resulting incubations were pooled to yield a higher sample concentration for analysis. The time point at which 30-50% of parent had degraded could then be investigated at 3 different levels of metabolite profiling and/or identification.

Data Analysis

From a plot of ln peak area ratio (compound peak area/internal standard peak area) against time, the gradient of the line is determined. Subsequently, half-life and intrinsic clearance are calculated using the equations below:

Elimination rate constant $(k) = (-\text{gradient})$

Half life $(t_{1/2})(\text{mins}) = \dfrac{0.693}{k}$

Intrinsic Clearance $(CL_{int})(\mu L/\min/\text{mg protein}) = \dfrac{V \times 0.693}{t_{1/2}}$ where $V$ = Incubation volume ($\mu L$/mg microsomal protein).

Two control compounds were included in the assay and if the values for these compounds were not within the specified limits the results were rejected and the experiment repeated.

Results

| Compound No. | T ½ human liver microsomes (mins) |
| --- | --- |
| (1) | 162 |
| (2) | 224 |
| (3) | 37.6 |
| (4) | 44.9 |
| (5) | 5.41 |
| (6) | 48 |

-continued

| Compound No. | T ½ human liver microsomes (mins) |
| --- | --- |
| (8) | 128 |
| (10) | 101 |
| (11) | 59.6 |
| (12) | 37.1 |
| (13) | 212 |
| (14) | 371 |

EXAMPLE 21

Inhibition of Cell Growth

The growth of cells was assessed in the presence and absence of compound (10) using a proliferation assay in an InuCyte™ live cell imager.

Experimental Procedure

All cells were purchased from ATCC (American Type Culture Collection) and maintained according to the supplier's recommendations. Cells used were RKO, HCT-15, WiDr, HT29, DLD-1, COLO320DM and COL0205 cells. 1,000 cells were seeded in 96-well plates with the recommended media. The day after seeding, the cell culture medium was exchanged to solutions that contained 0.05% DMSO and 5, 1 or 0.1 µmol/L compound (10). All samples were assessed in a minimum of six replicates. Plates were incubated in an IncuCyte™ (Essen BioScience) inside a cell culture incubator. Images were captured every second hour to monitor cell proliferation.

Results

Mutations in the Adenomatouse Polyposis Coli (APC) gene, which occur in most colorectal cancers (CRC), lead to ineffective degradation of β-catenin and aberrant up-regulation of Wnt signaling. As a result, CRC cells may undergo cell cycle arrest as a result of antagonized canonical Wnt. Therefore, the kinetics of cell proliferation was monitored in selected Wnt responsive CRC cell lines by using an IncuCyte life tracking system. In parallel, the colorectal cancer cell line RKO, which contains wild type APC and β-catenin and exhibits Wnt-independent cell growth was used as a control. The cell growth profiles for the cell lines RKO, HCT-15, WiDr, HT29, DLD-1, COLO320DM and COL0205, after treatment with DMSO (control), 0.1 µmol/L, 1 µmol/L and 5 µmol/L compound (10) are shown in FIGS. 1A to 1G, respectively.

Inhibition of canonical Wnt signaling by compound (10) promotes cell cycle arrest and specifically reduces proliferation in APC mutant CRC cells. Cell growth curves, as measured by IncuCyte™, show a concentration-dependent decrease of proliferation in various APC mutant CRC cells compared to the Wnt-independent CRC control cell line RKO that contains wild type APC. Plots show representative values from a minimum of two independent experiments and all relative standard deviations are below 20%. The cell lines HCT-15, WiDr, HT29, DLD-1, COLO320DM and COL0205 showed dose-dependent growth inhibition, while the control cell line RKO did not. In each case, apart from the control, the curve for DMSO (black line) reaches confluency in a shorter time than the other samples, which show dose-dependent inhibition of cell growth (i.e. greater inhibition of growth at increasing concentration of compound (10)-0.1 µM, light grey line; 1 µM, mid-grey line; and 5 µM, dark grey line).

EXAMPLE 22

Inhibition of the Wnt Pathway

Experimental Procedure

The inhibitory activities of compound (10) and XAV939 (Novartis; Huang et al., Nature (2009), 461, pp. 614-20), which is used as a positive control, were tested at various doses (in duplicate) using Chemiluminescent Assay Kits (BPS Bioscience, Nordic Biosite) against TNKS1 (Cat No. 80564), TNSK2 (Cat No. 80566) and PARP1 (Cat No. 80551). The procedures were performed according to the manufacturer's protocols.

Results

Figure 2:
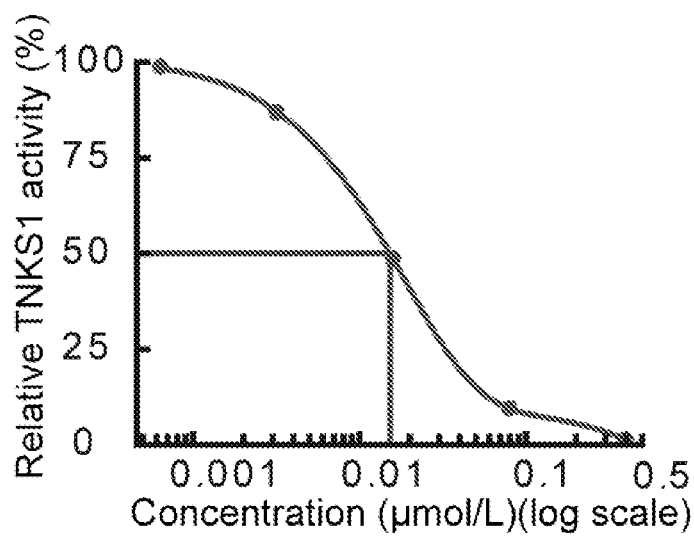
FIG. 2 shows the effect of XAV939 (FIG. 2A) and a compound of the invention (FIG. 2B) on the inhibition of TNKS1 in vitro.
Figure 2:
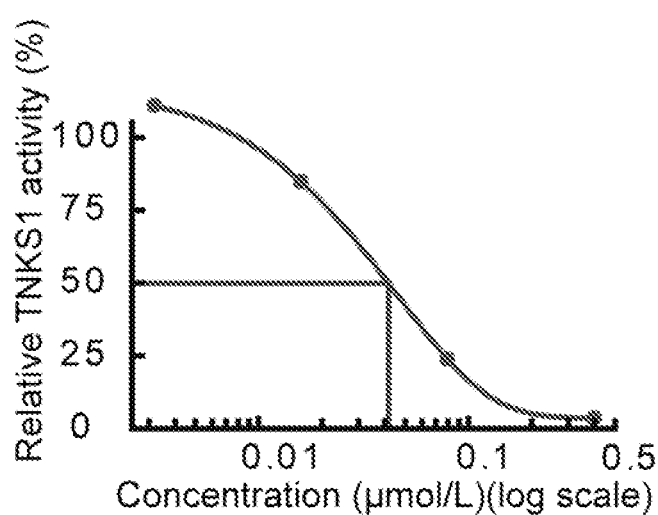
Figure 3:
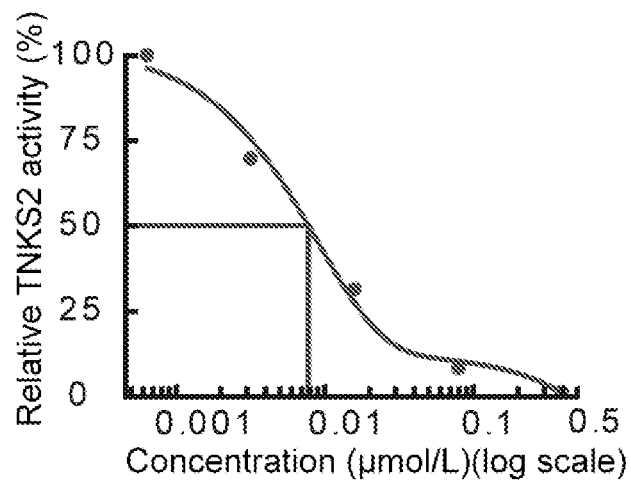
FIG. 3 shows the effect of XAV939 (FIG. 3A) and a compound of the invention (FIG. 3B) on the inhibition of TNKS2 in vitro.
Figure 3:
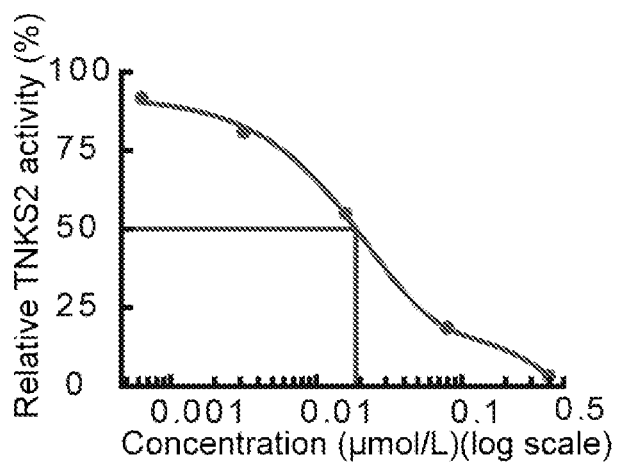
Figure 4:
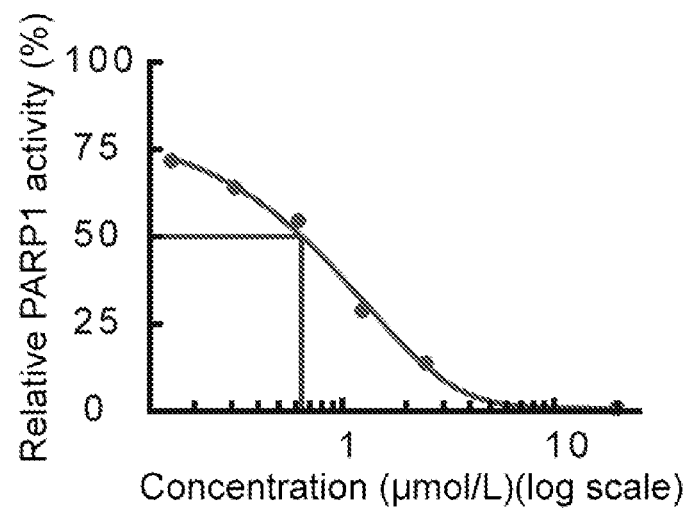
FIG. 4 shows the effect of XAV939 (FIG. 4A) and a compound of the invention (FIG. 4B) on the inhibition of PARP in vitro.
Figure 4:
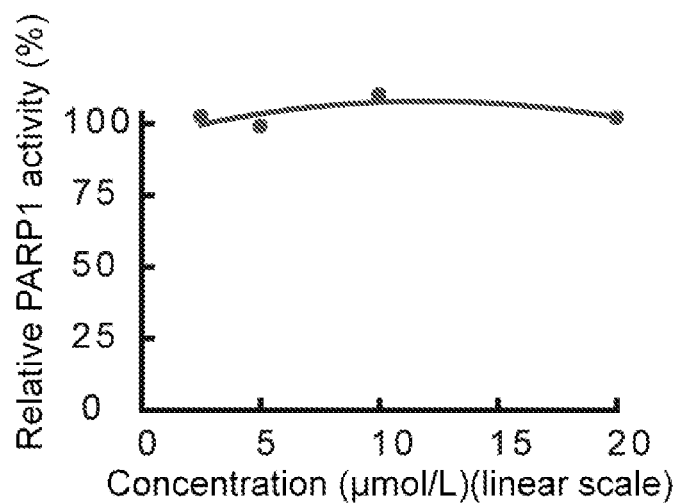

To test whether compound (10) decreased canonical Wnt signaling by inhibiting the PARP domain of TNKS1/2, biochemical assays for monitoring the activity of TNKS1/2 and PARP were performed. Compound (10) decreased auto-PARsylation of TNKS1 and TNKS2 in vitro with $IC_{50}$-values of 46 nmol/L and 19 nmol/L, respectively. However, in contrast to XAV939, compound (10) exhibited no inhibition of PARP1 at doses up to 20 µmol/L. The results of the Experiments are shown in FIGS. 2 (TNKS1), 3 (TNKS2) and 4 (PARP). In each case, the figure A shows the results obtained with XAV939 and figure B shows the results obtained with compound (10).

The $IC_{50}$ values calculated from the results of this experiment are as follows:

| Assay | $IC_{50}$ value for XAV939 | $IC_{50}$ value for compound (10) |
| --- | --- | --- |
| TNKS1 | 15 nM | 46 nM |
| TNKS2 | 7.8 nM | 19 nM |
| PARP | 0.64 µM | >20 µM |

The results of this experiment indicate that compound (10) blocks canonical Wnt signaling by specifically inhibiting auto-PARsylation of TNKS1/2 while leaving PARP1 activity unaffected.

EXAMPLE 23

Immunohistochemical Analysis

Experimental Procedure 50,000 SW480 cells (ATCC—maintained according to the supplier's recommendations) were seeded in 24-well plates on glass slides and exposed to DMSO (control) or 0.5 µmol/L of compound (10) for 18 hours. After incubation, the cells were fixed in 4% PFA in PBS for 10 minutes.

Figure 5:
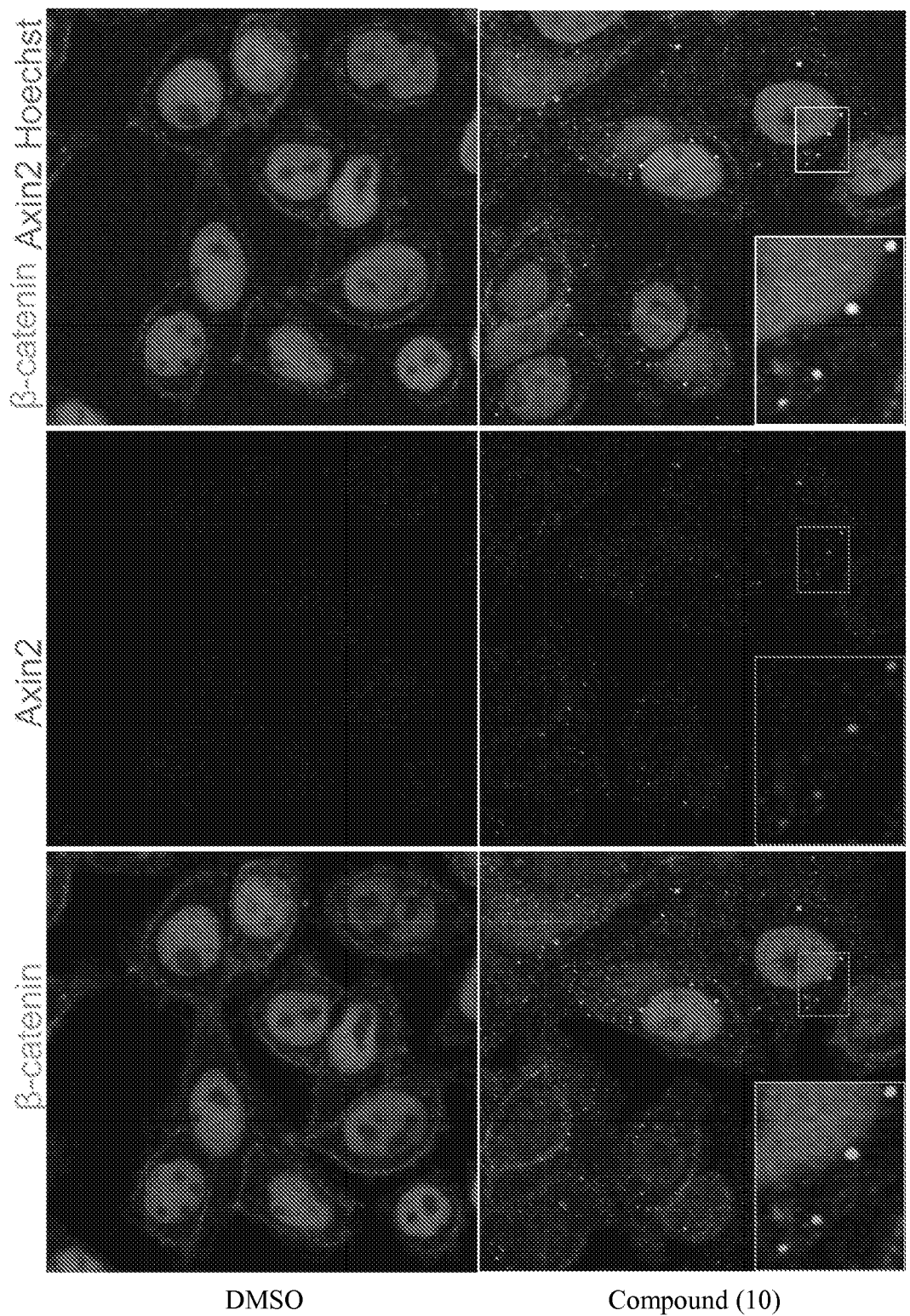
FIG. 5 shows the results of immunostaining of SW480 cells treated with DMSO (negative control, left-hand panels) and a compound of the invention (right-hand panels).

Immunostaining was performed as described in standard protocols. Primary antibodies used were β-catenin (610153, BD Transduction Laboratories™) or AXIN2 (76G6, Cell Signaling Technology). Secondary antibodies used were DyLight549 (555) donkey-anti-mouse and Cy2-donkey-anti-rabbit (both Jackson ImmunoResearch, 1:1000). The samples were imaged using a Zeiss Axiovert 200M Fluorescence/Live cell Imaging Microscope at 40 times magnification. A Zeiss LSM780 at 63 times magnification was used for confocal microscopy Results To gain an insight into the changes in cellular distribution of AXIN2 and β-catenin, SW480 cells treated with compound (10) were analyzed by immunofluorescence. A general reduction of total β-catenin, accompanied with a strong reduction of nuclear β-catenin, was detected at a dose of 500 nmol/L in most, but not all, compound (10) treated SW480 cells. Confocal microscopy (equal shutter speeds) revealed that the levels of cytoplasmic AXIN2 were significantly increased and large protein foci, apparently representing accumulated destruction complexes, were observed (magnified insert in FIG. 5). Degradation of β-catenin after compound (10) exposure appeared to be orchestrated by stabilization of AXIN2 in the destruction complex. Images of cells treated with DMSO and compound (10) are shown in FIG. 5.

The invention claimed is:
1. A compound of general formula I:

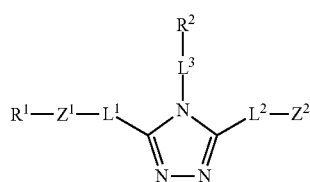

(wherein
$Z^1$ represents

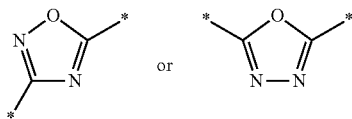

$Z^2$ represents phenyl, pyridyl, pyrimidinyl or oxadiazolyl optionally substituted by one or more groups $R_a$;
where each $R_a$ may be identical or different and may be selected from F, Cl, Br, I, $C_{1-6}$ alkyl, $C_{2-4}$ alkenyl, $C_{2-4}$ alkynyl, $C_{1-4}$ haloalkyl, —CN, —NO$_2$, —OR, —SR, —C(O)R, —C(O)OR, —OC(O)R, —OC(O)NR$_2$, —NR$_2$, —NR—C(O)R, —NR—C(O)OR, —S(O)R, —S(O)$_2$R, —S(O)OR or —S(O)$_2$NR$_2$ group (where each R is independently H, $C_{1-6}$ alkyl, $C_{1-6}$ haloalkyl, $C_{2-6}$ alkenyl or $C_{2-6}$ alkynyl);
$R^1$ represents a phenyl or pyridyl group optionally substituted by one or more groups $R_b$;
where each $R_b$ may be identical or different and may be selected from F, Cl, Br, I, $C_{1-6}$ alkyl optionally interrupted by one or more —O—, —S— or —NR— groups, $C_{2-4}$ alkenyl, $C_{2-4}$ alkynyl, $C_{1-4}$ haloalkyl, —CN, —NO$_2$, —OR, —SR, —C(O)R, —C(O)OR, —OC(O)R, —OC(O)NR$_2$, —C(O)NR$_2$, —NR$_2$, —NR—C(O)R, —NR—C(O)OR, —S(O)R, —S(O)$_2$R, —S(O)OR or —S(O)$_2$NR$_2$ group (where each R is independently H, $C_{1-6}$ alkyl, $C_{1-6}$ haloalkyl, $C_{2-6}$ alkenyl or $C_{2-6}$ alkynyl);
$R^2$ represents a phenyl group optionally substituted by one or more groups $R_c$;
where each $R_c$ may be identical or different and may be selected from halogen F, Cl, Br, I, $C_{1-6}$ alkyl, $C_{2-4}$ alkenyl, $C_{2-4}$ alkynyl, $C_{1-4}$ haloalkyl, —CN, —NO$_2$, —OR, —SR, —C(O)R, —C(O)OR, —OC(O)R, —OC(O)NR$_2$, —NR$_2$, —NR—C(O)R, —NR—C(O)OR, —S(O)R, —S(O)$_2$R, or —S(O)OR or group (where each R is independently H, $C_{1-6}$ alkyl, $C_{1-6}$ haloalkyl, $C_{2-6}$ alkenyl or $C_{2-6}$ alkynyl);
$L^1$ represents a $C_{1-4}$ alkylene group optionally substituted by one or more groups $R_d$, wherein one or more methylene groups are each replaced by a group selected from —CR$_e$=CR$_f$—, —C≡C— and —C=C=C—; and
wherein one or more methylene groups may each additionally be replaced by a group $Y^1$;
where each $Y^1$ is independently selected from —O—, —S—, —NH—, —NR'''—, —NR'''—C(O)—, —C(O)—NR'''—, —C(O)—, —S(O$_2$)—, —S(O)— and —CR'''=N— (where each R''' is independently hydrogen or $C_{1-6}$ alkyl);
where each $R_d$ may be identical or different and may be selected from $C_{1-6}$ alkyl, hydroxy, $C_{1-6}$ alkoxy, F, Cl, Br and I; and
where $R_e$ and $R_f$ are independently selected from H, $C_{1-3}$ alkyl, halogen, $C_{1-3}$ haloalkyl, —CN, —NO$_2$, —OR, —SR, —C(O)R, —C(O)OR, —OC(O)R, —OPO$_3$R, —OSO$_2$R and —OSiR$_4$ (where each R is independently H, $C_{1-6}$ alkyl or $C_{1-6}$ haloalkyl);
$L^2$ represents a bond; and
$L^3$ represents a bond)
or a stereoisomers or pharmaceutically acceptable salt thereof, wherein said compound is other than

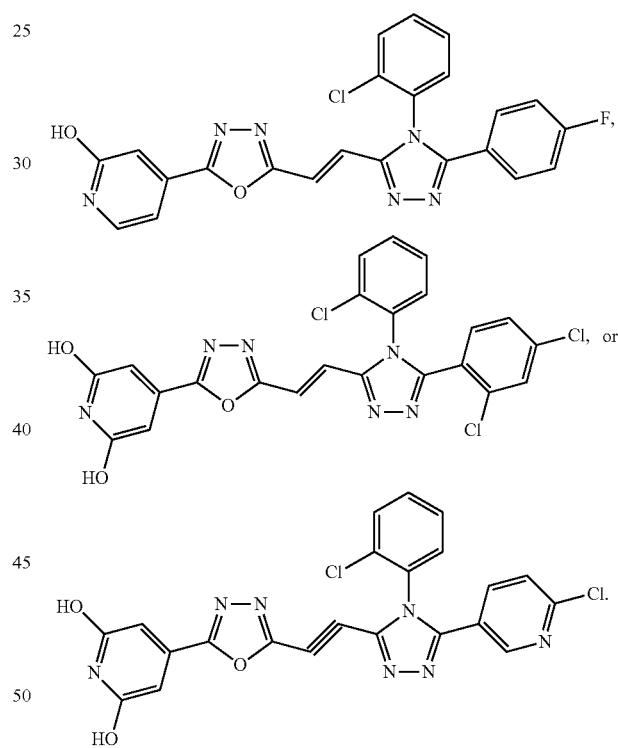

2. A compound as claimed in claim 1, wherein $L^1$ is a $C_{1-4}$ alkylene group optionally substituted by one or more groups $R_d$, wherein one or more methylene groups are each replaced by a group —CR$_e$=CR$_f$— or by a group —C≡C—;
where each $R_d$ may be identical or different and may be selected from $C_{1-6}$ alkyl, hydroxy, $C_{1-6}$ alkoxy, F, Cl, Br and I; and
where $R_e$ and $R_f$ are independently selected from H, $C_{1-3}$ alkyl, halogen, and —CN.

3. A compound as claimed in claim 1, wherein:
$Z^2$ represents phenyl, pyridyl or pyrimidinyl optionally mono- or di-substituted by a group $R_a$;
where $R_a$ may be selected from F, Cl, Br, I, hydroxy, $C_{1-6}$ alkoxy, and —S(O)$_2$R (where R is H or $C_{1-3}$ alkyl);

R¹ represents a phenyl or pyridyl group optionally mono-substituted by group $R_b$;

where $R_b$ is selected from F, Cl, Br, I, $C_{1-6}$ alkyl, $C_{1-6}$ alkoxy, hydroxy and —CN;

R² represents a phenyl group optionally mono- or di-substituted by a group $R_c$;

where each $R_c$ may be identical or different and may be selected from F, Cl, Br, I, $C_{1-6}$ alkyl, and $C_{1-6}$ alkoxy;

L¹ represents a $C_{1-4}$ alkylene group optionally substituted by one or more groups $R_d$, wherein one or two methylene groups are each replaced by a group —$CR_e$=$CR_f$— or by a group —C≡C—;

where each $R_d$ may be identical or different and may be selected from $C_{1-6}$ alkyl, hydroxy and $C_{1-6}$ alkoxy;

where $R_e$ and $R_f$ are independently selected from H, $C_{1-3}$ alkyl and halogen or a stereoisomer or pharmaceutically acceptable salt thereof.

4. A compound as claimed in claim 1, wherein L¹ is a group —$CR_e$=$CR_f$—, —C≡C— or —C=C=C— in which $R_e$ and $R_f$ are as defined in claim 1.

5. A compound as claimed in claim 1, wherein L¹ is a group —$CR_e$=$CR_f$— in which $R_e$ and $R_f$ are independently selected from H and methyl.

6. A compound as claimed in claim 1 having the formula IIc or IId:

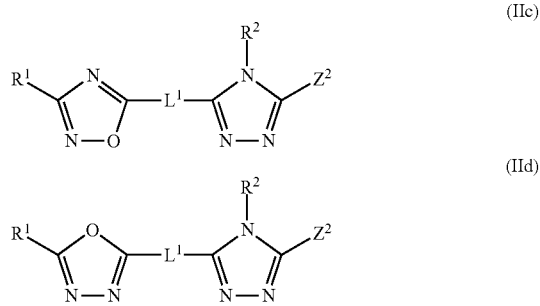

(wherein
Z² is an optionally substituted pyridyl, phenyl or pyrimidinyl ring;
R¹ is a substituted phenyl or pyridyl ring;
R² is an optionally substituted phenyl ring; and
L¹ is cis or trans —CH=CH—) or a stereoisomer or pharmaceutically acceptable salt or thereof.

7. A compound as claimed in claim 1 selected from the following:

| Compound No. | Structure |
|---|---|
| (1) | ![structure 1] |
| (2) | ![structure 2] |
| (3) | ![structure 3] |

| Compound No. | Structure |
|---|---|
| (4) | 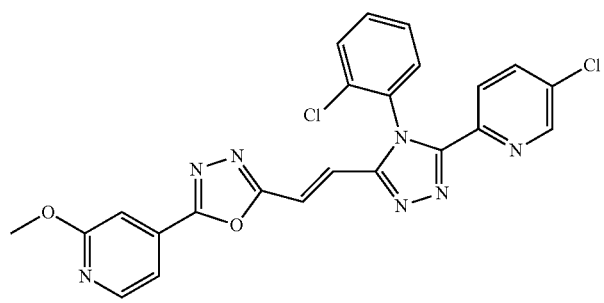 [SMILES: COc1cc(-c2nnc(/C=C/c3nnc(-c4ccc(Cl)cn4)n3-c3ccccc3Cl)o2)ccn1] |
| (5) | 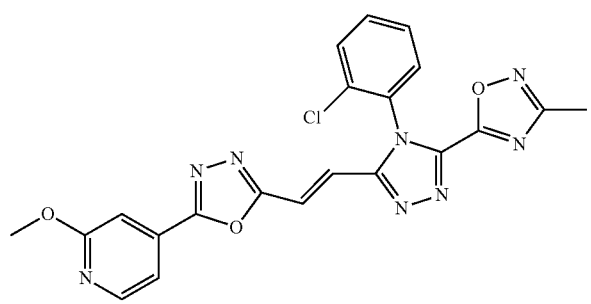 |
| (6) | 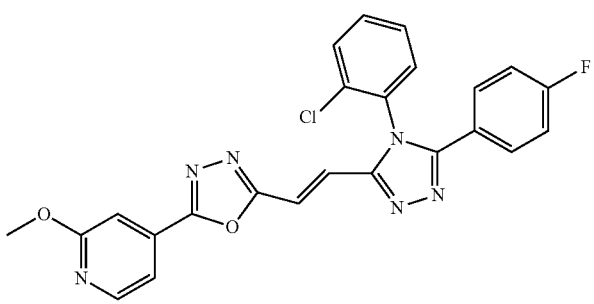 [SMILES: COc1cc(-c2nnc(/C=C/c3nnc(-c4ccc(F)cc4)n3-c3ccccc3Cl)o2)ccn1] |
| (9) | 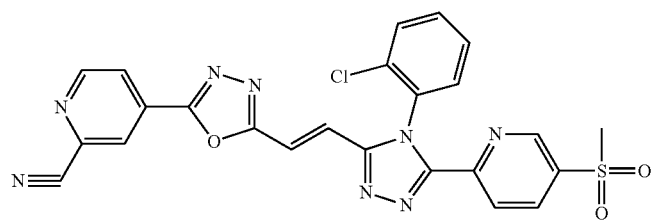 [SMILES: CS(=O)(=O)c1ccc(-c2nnc(/C=C/c3nnc(-c4ccnc(C#N)c4)o3)n2-c2ccccc2Cl)nc1] |
| (10) | 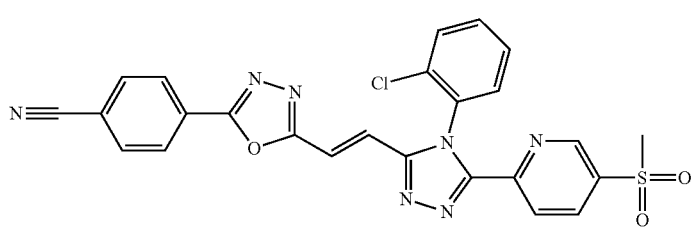 |

| Compound No. | Structure |
|---|---|
| (11) | 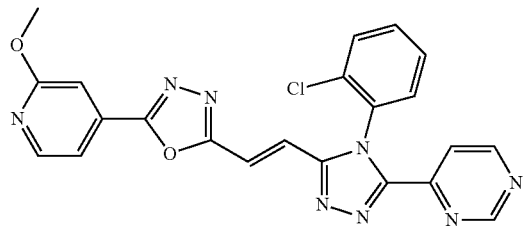 [SMILES: COc1cc(-c2nnc(/C=C/c3nnc(-c4ccncn4)n3-c3ccccc3Cl)o2)ccn1] |
| (12) | 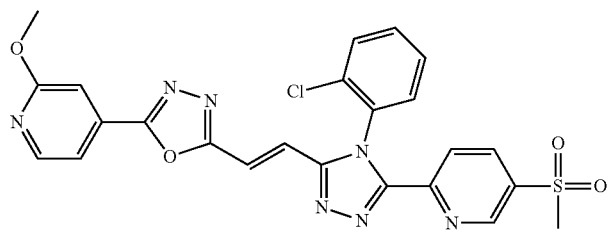 [SMILES: COc1cc(-c2nnc(/C=C/c3nnc(-c4ccc(S(C)(=O)=O)cn4)n3-c3ccccc3Cl)o2)ccn1] |
| (13) | 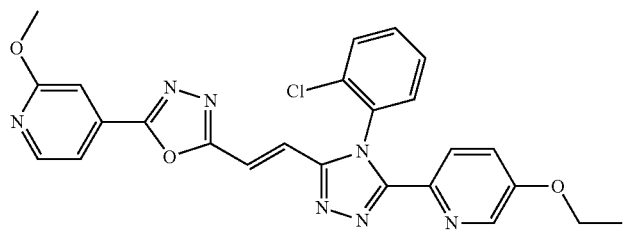 [SMILES: CCOc1ccc(-c2nnc(/C=C/c3nnc(-c4ccnc(OC)c4)o3)n2-c2ccccc2Cl)nc1] |
| (14) | 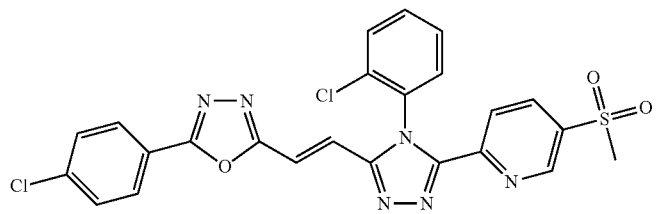 [SMILES: CS(=O)(=O)c1ccc(-c2nnc(/C=C/c3nnc(-c4ccc(Cl)cc4)o3)n2-c2ccccc2Cl)nc1] |
| (15) | 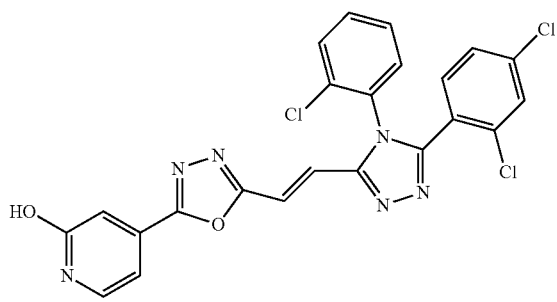 [SMILES: Oc1cc(-c2nnc(/C=C/c3nnc(-c4ccc(Cl)cc4Cl)n3-c3ccccc3Cl)o2)ccn1] |

-continued
| Compound No. | Structure |
|---|---|
| (16) | 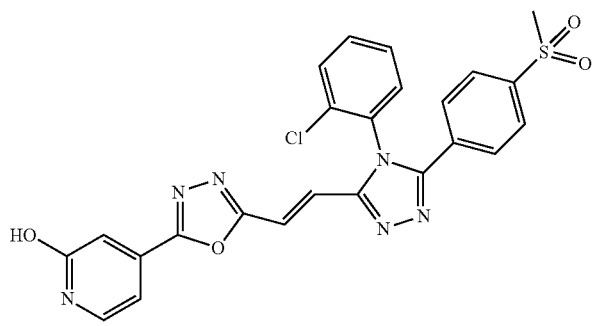 [SMILES: CS(=O)(=O)c1ccc(-c2nnc(/C=C/c3nnc(-c4ccnc(O)c4)o3)n2-c2ccccc2Cl)cc1] |
| (17) | 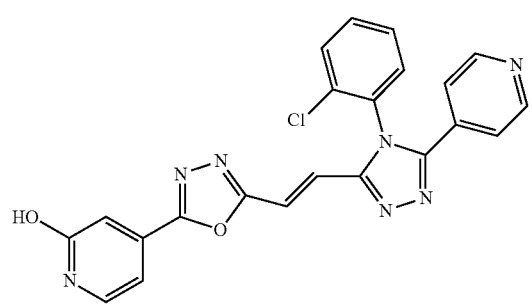 [SMILES: Oc1cc(-c2nnc(/C=C/c3nnc(-c4ccncc4)n3-c3ccccc3Cl)o2)ccn1] |
| (18) | 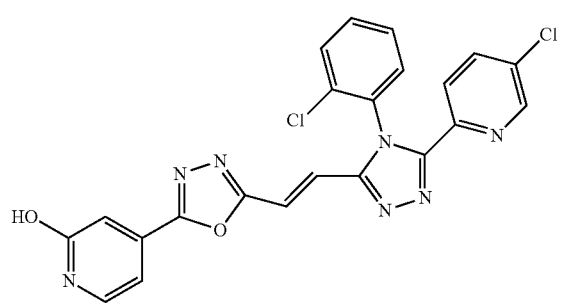 [SMILES: Oc1cc(-c2nnc(/C=C/c3nnc(-c4ccc(Cl)cn4)n3-c3ccccc3Cl)o2)ccn1] |
| (19) | 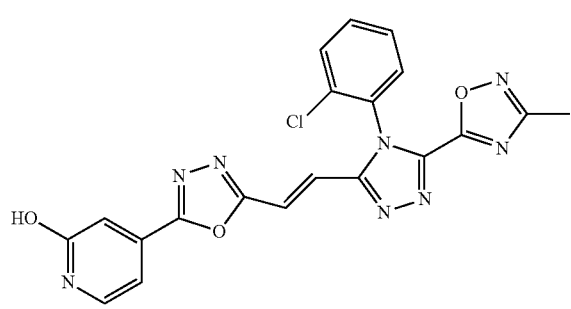 [SMILES: Cc1noc(-c2nnc(/C=C/c3nnc(-c4ccnc(O)c4)o3)n2-c2ccccc2Cl)n1] |
| (21) | 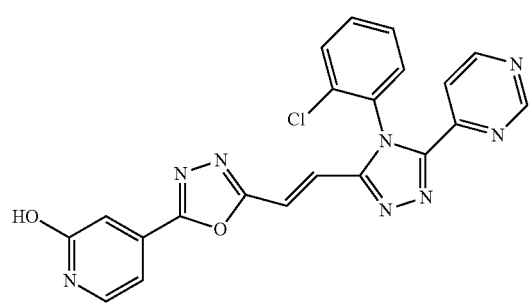 |

| Compound No. | Structure |
|---|---|
| (22) | 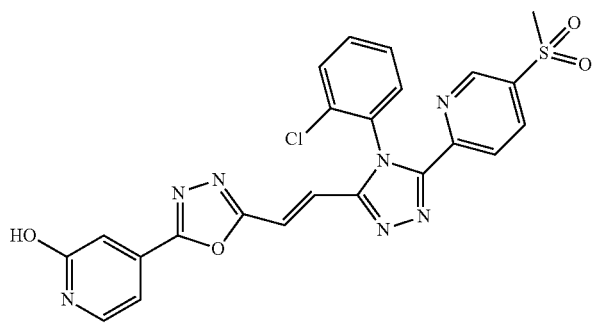 |
| (23) | 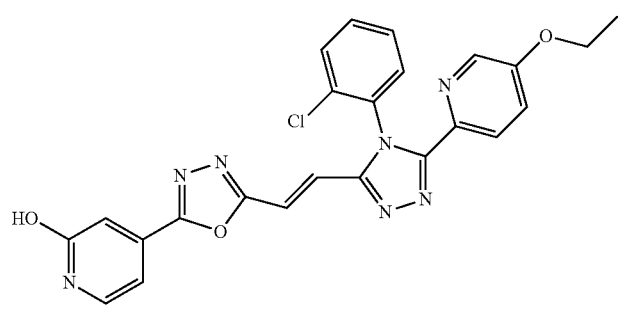 [SMILES: CCOc1ccc(-c2nnc(/C=C/c3nnc(-c4ccnc(O)c4)o3)n2-c2ccccc2Cl)nc1] |
| (24) | 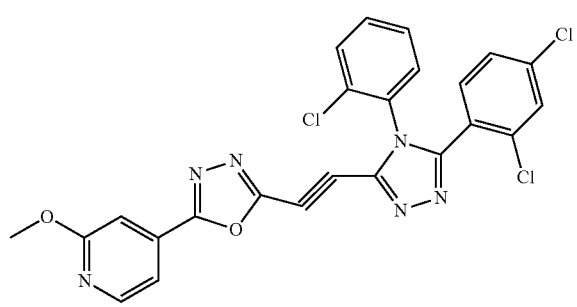 [SMILES: COc1cc(-c2nnc(C#Cc3nnc(-c4ccc(Cl)cc4Cl)n3-c3ccccc3Cl)o2)ccn1] |
| (25) | 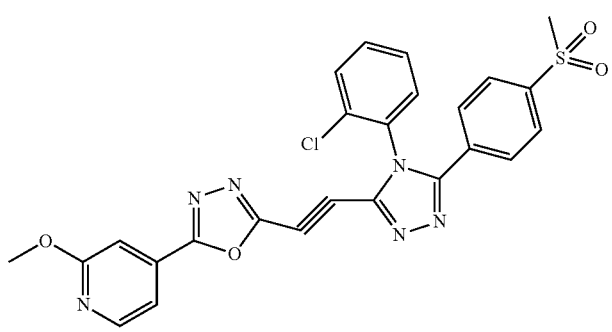 [SMILES: COc1cc(-c2nnc(C#Cc3nnc(-c4ccc(S(C)(=O)=O)cc4)n3-c3ccccc3Cl)o2)ccn1] |
| (26) | 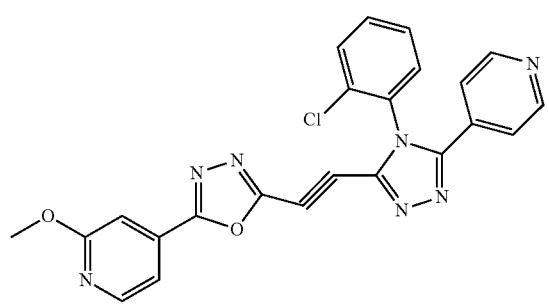 |

| Compound No. | Structure |
|---|---|
| (27) | 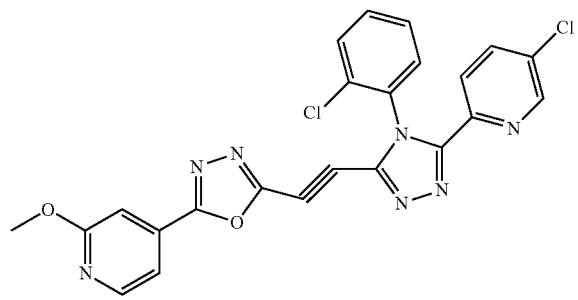 [SMILES: COc1cc(-c2nnc(C#Cc3nnc(-c4ccc(Cl)cn4)n3-c3ccccc3Cl)o2)ccn1] |
| (28) | 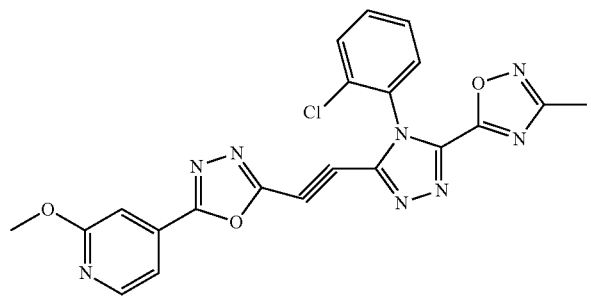 |
| (29) | 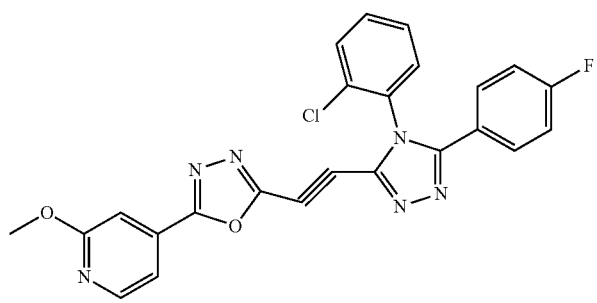 [SMILES: COc1cc(-c2nnc(C#Cc3nnc(-c4ccc(F)cc4)n3-c3ccccc3Cl)o2)ccn1] |
| (31) | 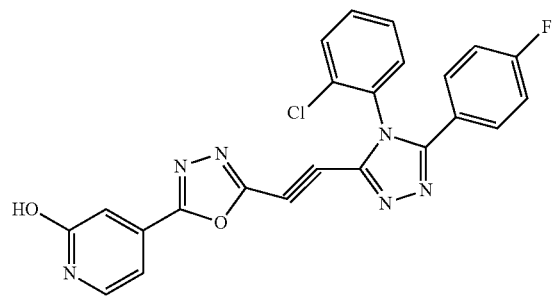 [SMILES: Oc1cc(-c2nnc(C#Cc3nnc(-c4ccc(F)cc4)n3-c3ccccc3Cl)o2)ccn1] |
| (32) | 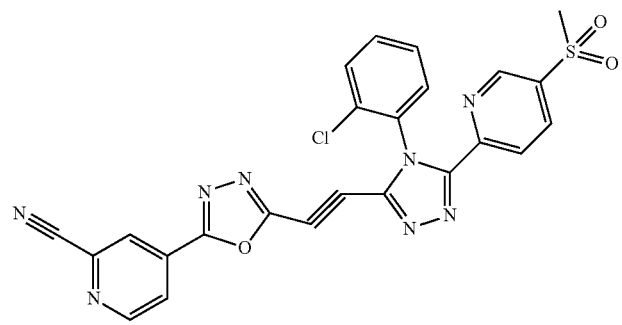 [SMILES: CS(=O)(=O)c1ccc(-c2nnc(C#Cc3nnc(-c4ccnc(C#N)c4)o3)n2-c2ccccc2Cl)nc1] |

| Compound No. | Structure |
|---|---|
| (33) | 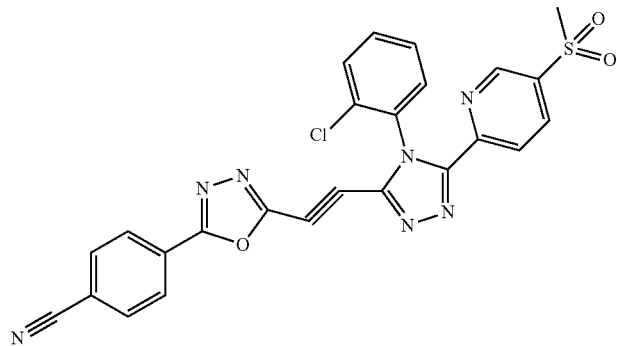 [SMILES: CS(=O)(=O)c1ccc(-c2nnc(C#Cc3nnc(-c4ccc(C#N)cc4)o3)n2-c2ccccc2Cl)nc1] |
| (34) | 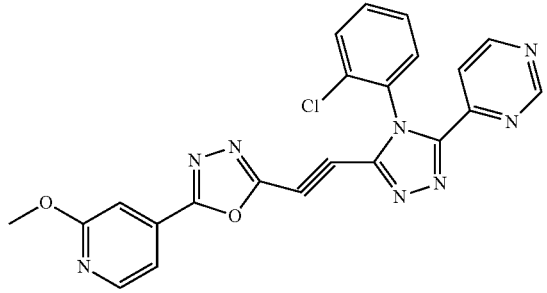 |
| (35) | 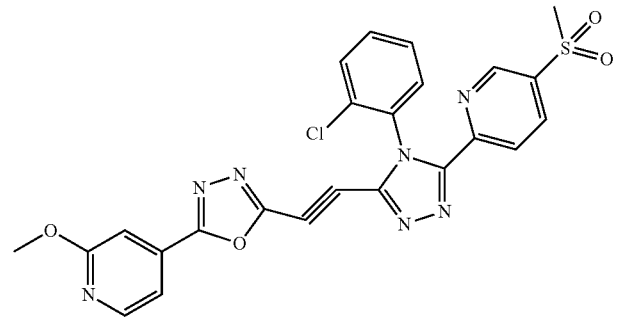 [SMILES: COc1cc(-c2nnc(C#Cc3nnc(-c4ccc(S(C)(=O)=O)cn4)n3-c3ccccc3Cl)o2)ccn1] |
| (36) | 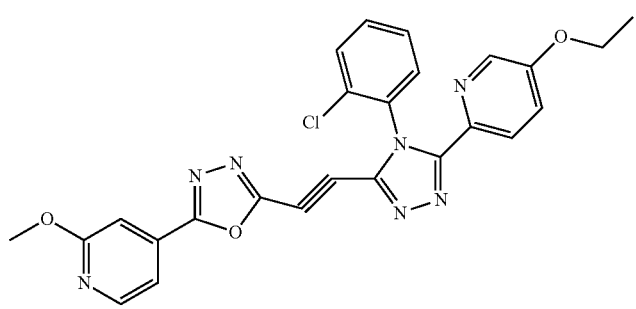 [SMILES: CCOc1ccc(-c2nnc(C#Cc3nnc(-c4ccnc(OC)c4)o3)n2-c2ccccc2Cl)nc1] |

| Compound No. | Structure |
|---|---|
| (37) | 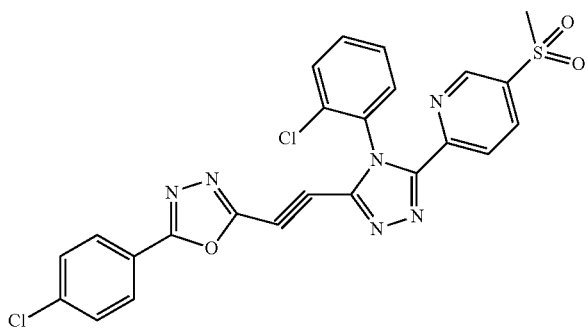 [SMILES: CS(=O)(=O)c1ccc(-c2nnc(C#Cc3nnc(-c4ccc(Cl)cc4)o3)n2-c2ccccc2Cl)nc1] |
| (38) | 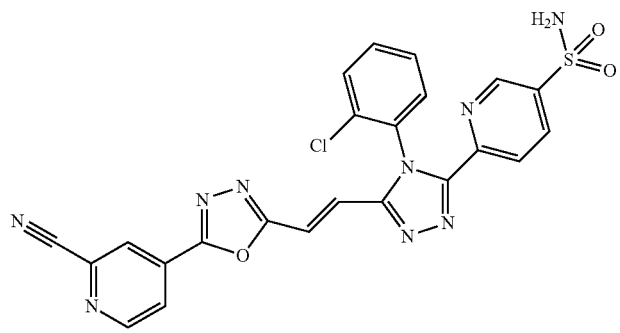 [SMILES: N#Cc1cc(-c2nnc(/C=C/c3nnc(-c4ccc(S(N)(=O)=O)cn4)n3-c3ccccc3Cl)o2)ccn1] |
| (39) | 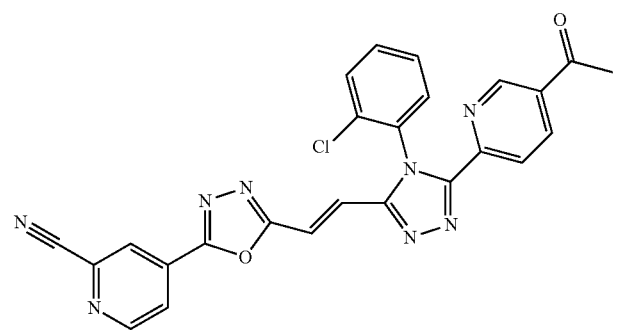 [SMILES: CC(=O)c1ccc(-c2nnc(/C=C/c3nnc(-c4ccnc(C#N)c4)o3)n2-c2ccccc2Cl)nc1] |
| (40) | 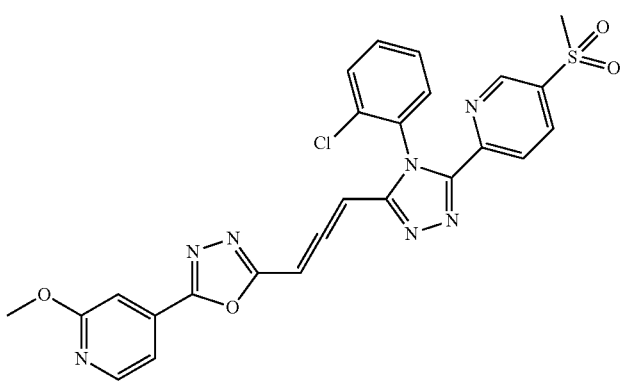 [SMILES: COc1cc(-c2nnc(C=C=Cc3nnc(-c4ccc(S(C)(=O)=O)cn4)n3-c3ccccc3Cl)o2)ccn1] |

| Compound No. | Structure |
|---|---|
| (41) | 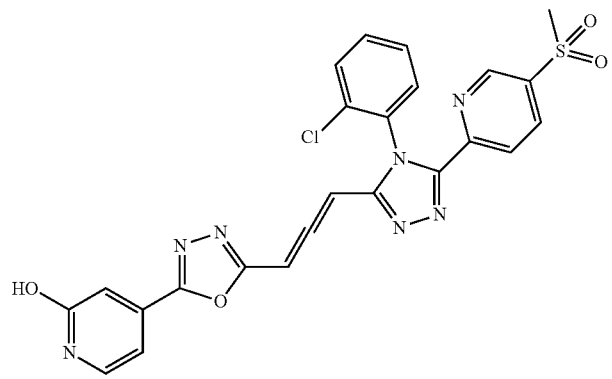 [SMILES: CS(=O)(=O)c1ccc(-c2nnc(C=C=Cc3nnc(-c4ccnc(O)c4)o3)n2-c2ccccc2Cl)nc1] |
| (42) | 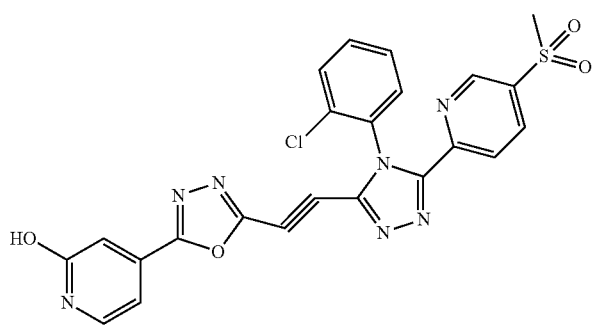 [SMILES: CS(=O)(=O)c1ccc(-c2nnc(C#Cc3nnc(-c4ccnc(O)c4)o3)n2-c2ccccc2Cl)nc1] |
| (43) | 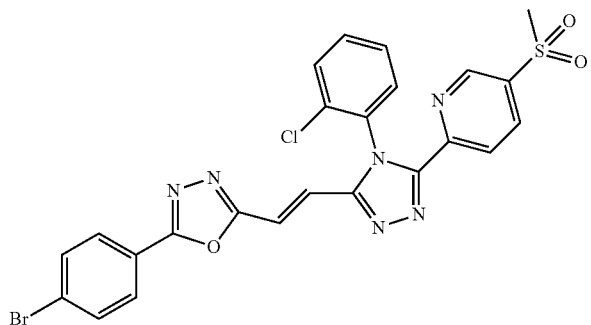 [SMILES: CS(=O)(=O)c1ccc(-c2nnc(/C=C/c3nnc(-c4ccc(Br)cc4)o3)n2-c2ccccc2Cl)nc1] |
| (44) | 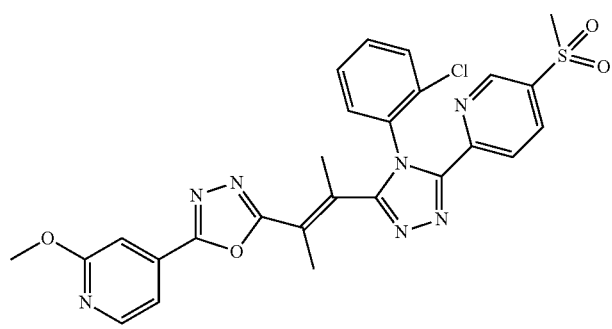 [SMILES: COc1cc(-c2nnc(/C(C)=C(\C)c3nnc(-c4ccc(S(C)(=O)=O)cn4)n3-c3ccccc3Cl)o2)ccn1] |

| Compound No. | Structure |
|---|---|
| (45) | 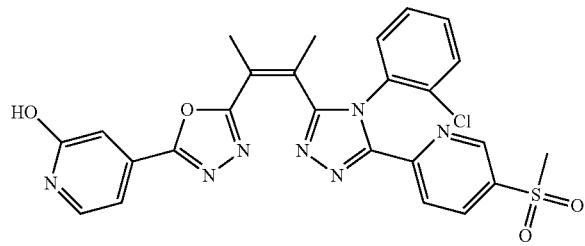 [SMILES: C/C(=C(\C)c1nnc(-c2ccc(S(C)(=O)=O)cn2)n1-c1ccccc1Cl)c1nnc(-c2ccnc(O)c2)o1] |
| (46) | 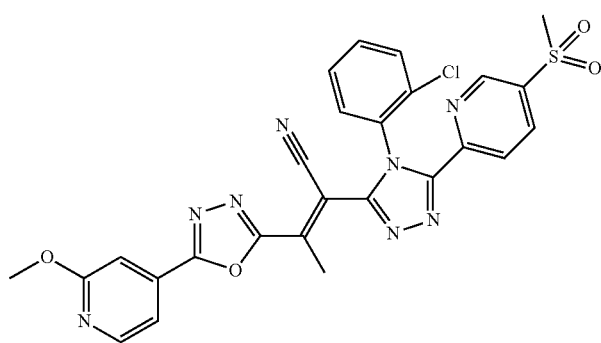 [SMILES: COc1cc(-c2nnc(/C(C)=C(\C#N)c3nnc(-c4ccc(S(C)(=O)=O)cn4)n3-c3ccccc3Cl)o2)ccn1] |
| (47) | 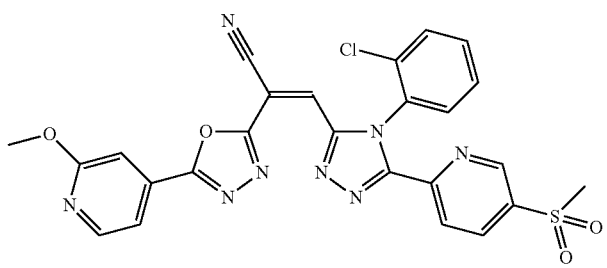 [SMILES: COc1cc(-c2nnc(/C(C#N)=C\c3nnc(-c4ccc(S(C)(=O)=O)cn4)n3-c3ccccc3Cl)o2)ccn1] |
| (48) | 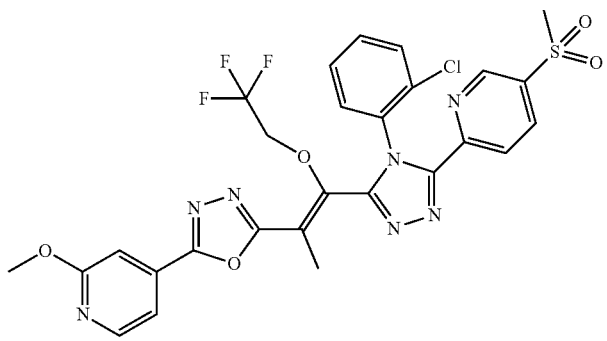 [SMILES: COc1cc(-c2nnc(/C(C)=C(\OCC(F)(F)F)c3nnc(-c4ccc(S(C)(=O)=O)cn4)n3-c3ccccc3Cl)o2)ccn1] |

| Compound No. | Structure |
|---|---|
| (49) | 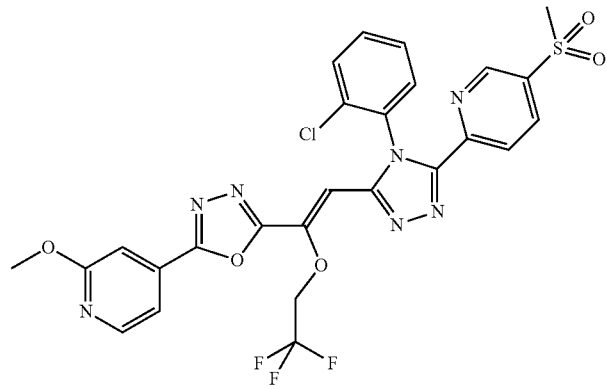 [SMILES: COc1cc(-c2nnc(/C(=C/c3nnc(-c4ccc(S(C)(=O)=O)cn4)n3-c3ccccc3Cl)OCC(F)(F)F)o2)ccn1] |
| (50) | 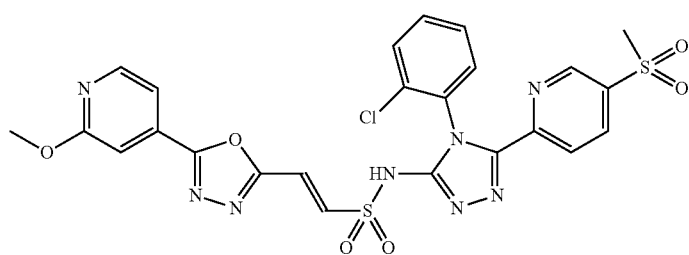 [SMILES: COc1cc(-c2nnc(/C=C/S(=O)(=O)Nc3nnc(-c4ccc(S(C)(=O)=O)cn4)n3-c3ccccc3Cl)o2)ccn1] |
| (51) | 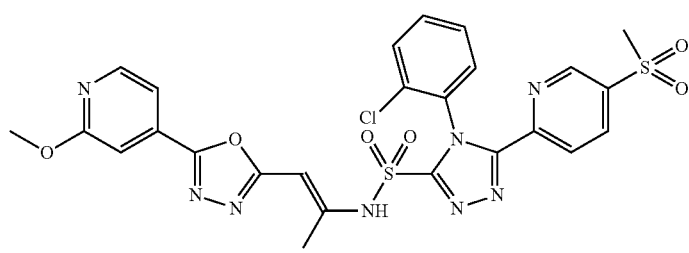 [SMILES: COc1cc(-c2nnc(/C=C(\C)NS(=O)(=O)c3nnc(-c4ccc(S(C)(=O)=O)cn4)n3-c3ccccc3Cl)o2)ccn1] |
| (52) | 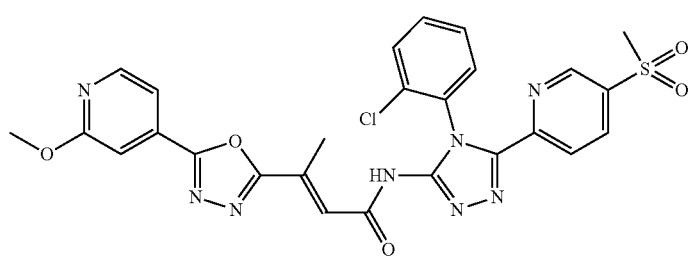 [SMILES: COc1cc(-c2nnc(/C(C)=C/C(=O)Nc3nnc(-c4ccc(S(C)(=O)=O)cn4)n3-c3ccccc3Cl)o2)ccn1] |
| (53) | 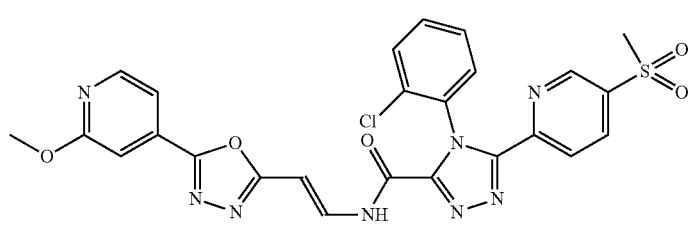 [SMILES: COc1cc(-c2nnc(/C=C/NC(=O)c3nnc(-c4ccc(S(C)(=O)=O)cn4)n3-c3ccccc3Cl)o2)ccn1] |

| Compound No. | Structure |
|---|---|
| (54) | 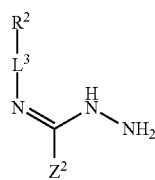 |
| (55) | 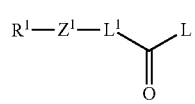 | or a stereoisomer or pharmaceutically acceptable salt thereof.

8. A compound as claimed in claim 7 which is selected from the following: Compound Nos. (1), (2), (3), (4), (5), (6), (10), (11), (12), (14), and (33), their stereoisomers and pharmaceutically acceptable salts thereof.

9. A compound as claimed in claim 7 which is selected from the following: Compound Nos. (2), (3), (4), (10), (11), (12), and (14), their stereoisomers and pharmaceutically acceptable salts thereof.

10. A method for the preparation of a compound of formula I as defined in claim 1, said method comprising at least one of the following steps:

(a) reacting a compound of general formula III:

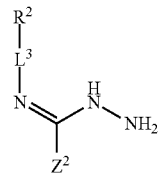

(III)

(wherein $Z^2$, $R^2$ and $L^3$ are as hereinbefore defined) with a compound of general formula IV:

$R^1-Z^1-L^1 \underset{O}{\overset{}{\diagdown}} L$ (IV)

(wherein $R^1$, $Z^1$ and $L^1$ are as hereinbefore defined and L denotes a leaving group such as a halogen atom, e.g. Cl);

(b) reacting a compound of general formula III:

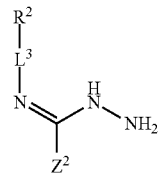

(III)

(wherein $Z^2$, $R^2$ and $L^3$ are as hereinbefore defined) with a compound of general formula V:

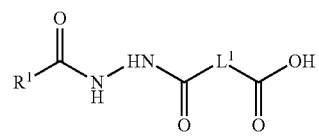

(V)

(wherein $R^1$ and $L^1$ are as hereinbefore defined);

(c) if desired, resolving a compound thus obtained into the stereoisomers thereof; and/or (d) converting a compound thus obtained into a salt thereof, particularly a pharmaceutically acceptable salt thereof.

11. A pharmaceutical formulation comprising a compound as claimed in claim 1, or a pharmaceutically acceptable salt thereof, together with one or more pharmaceutically acceptable carriers or excipients.

* * * * *